United States Patent
Eike et al.

(10) Patent No.: US 12,239,686 B2
(45) Date of Patent: Mar. 4, 2025

(54) IMMUNE CHECKPOINT INHIBITOR COMBINATIONS

(71) Applicant: LYTIX BIOPHARMA AS, Tromsø (NO)

(72) Inventors: Liv Marie Eike, Tromsø (NO); Ketil André Camilio, Tromsø (NO); Baldur Sveinbjörnsson, Tromsø (NO); Laurence Zitvogel, Villejuif (FR); Takahiro Yamazaki, Villejuif (FR); Oystein Rekdal, Billingstad (NO); John Sigurd Mjoen Svendsen, Kvaløysletta (NO)

(73) Assignee: LYTIX BIOPHARMA AS, Tromsø (NO)

( * ) Notice: Subject to any disclaimer, the term of this patent is extended or adjusted under 35 U.S.C. 154(b) by 0 days.

(21) Appl. No.: 18/598,719

(22) Filed: Mar. 7, 2024

(65) Prior Publication Data
US 2024/0293506 A1    Sep. 5, 2024

Related U.S. Application Data

(63) Continuation of application No. 17/366,463, filed on Jul. 2, 2021, now abandoned, which is a continuation
(Continued)

(30) Foreign Application Priority Data

Dec. 11, 2014  (GB) .................................. 1422084
Apr. 10, 2015  (GB) .................................. 1506127
Jun. 11, 2015  (JP) .............................. 2015-118495

(51) Int. Cl.
*A61K 38/08*    (2019.01)
*A61K 38/17*    (2006.01)
(Continued)

(52) U.S. Cl.
CPC .......... *A61K 38/1729* (2013.01); *A61K 38/08* (2013.01); *A61K 39/39533* (2013.01);
(Continued)

(58) Field of Classification Search
CPC .............. A61K 38/08; A61K 39/39533; A61K 39/39558; A61K 2039/585; C07K 7/06;
(Continued)

(56) References Cited

U.S. PATENT DOCUMENTS 6,458,369 B1    10/2002    Berd
11,083,774 B2 *  8/2021    Eike .................. A61K 39/39533
(Continued)

FOREIGN PATENT DOCUMENTS

WO    97/20574 A1    6/1997
WO    2004/004771 A1    1/2004
(Continued)

OTHER PUBLICATIONS

Berge et al: "Abstract 477: Long-term protection against B16F1 melanoma upon vaccination with tumor cell lysate combined with LTX-315 as a novel adjuvant.", Cancer Research, vol. 73, Apr. 15, 2013, p. 477.
(Continued)

*Primary Examiner* — Jeffrey E. Russel
(74) *Attorney, Agent, or Firm* — Fox Rothschild LLP

(57) ABSTRACT

The present invention provides a compound, preferably a peptide, having the following characteristics:
  a) consisting of 9 amino acids in a linear arrangement;
  b) of those 9 amino acids, 5 are cationic and 4 have a lipophilic R group;
  c) at least one of said 9 amino acids is a non-genetically coded amino acid (e.g. a modified derivative of a genetically coded amino acid); and optionally
(Continued)

Figure 1:
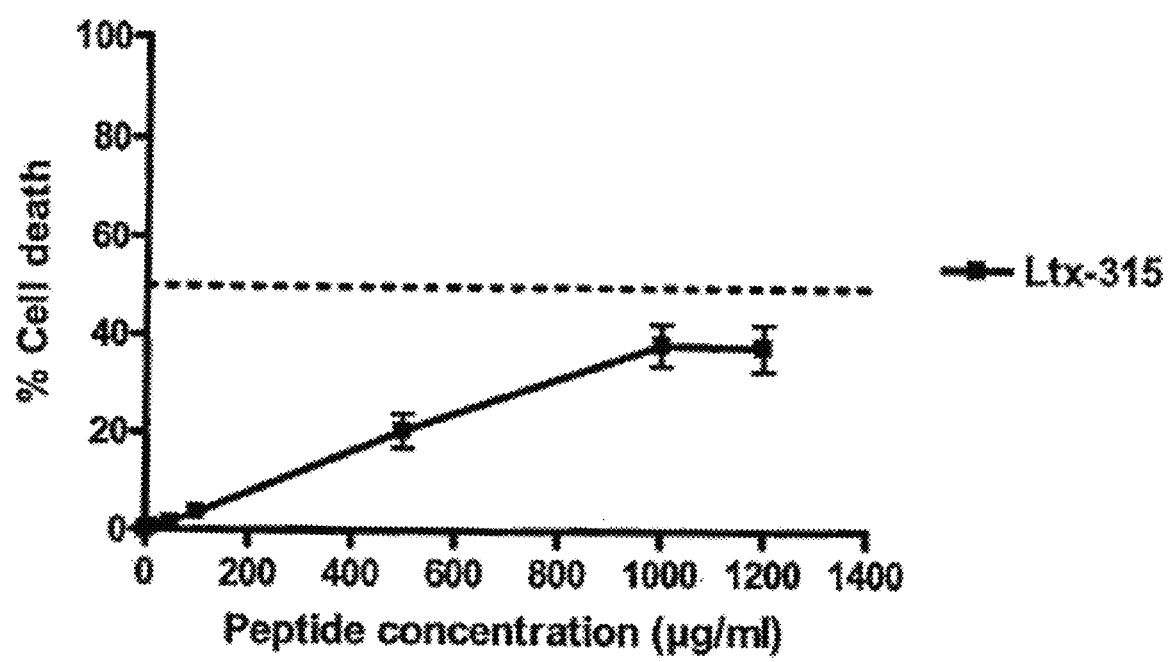

d) the lipophilic and cationic residues are arranged such that there are no more than two of either type of residue adjacent to one another; and further optionally e) the molecule comprises two pairs of adjacent cationic amino acids and one or two pairs of adjacent lipophilic residues;

for use in the treatment of a tumour by combined, sequential or separate administration with an immune checkpoint inhibitor. The present invention further provides pharmaceutical packs or compositions comprising these active agents and methods of treating a tumour comprising administration of these active agents. Also provided are the peptidic compounds as defined above for use in the destabilisation of a mitochondrial membrane, and a peptidic compound as defined above and an immunotherapeutic agent as a combined preparation for separate, simultaneous or sequential use in treating tumours.

14 Claims, 29 Drawing Sheets

Specification includes a Sequence Listing.

Related U.S. Application Data of application No. 15/534,800, filed as application No. PCT/EP2015/075722 on Nov. 4, 2015, now Pat. No. 11,083,774.

(51) Int. Cl.
| | | |
|---|---|---|
| *A61K 39/39* | (2006.01) | |
| *A61K 39/395* | (2006.01) | |
| *A61K 45/06* | (2006.01) | |
| *A61P 35/00* | (2006.01) | |
| *C07K 7/06* | (2006.01) | |
| *C07K 16/28* | (2006.01) | |
| *A61K 38/00* | (2006.01) | |
| *A61K 39/00* | (2006.01) | |

(52) U.S. Cl.
CPC ........ *A61K 39/39558* (2013.01); *A61K 45/06* (2013.01); *A61P 35/00* (2018.01); *C07K 7/06* (2013.01); *C07K 16/2818* (2013.01); *C07K 16/2827* (2013.01); *A61K 38/00* (2013.01); *A61K 2039/585* (2013.01); *A61K 2300/00* (2013.01)

(58) Field of Classification Search
CPC ............ C07K 16/2818; C07K 16/2827; C07K 16/2896
See application file for complete search history.

(56) References Cited

U.S. PATENT DOCUMENTS

| | | | |
|---|---|---|---|
| 11,123,398 B2* | 9/2021 | Eike .................... | A61K 31/513 |
| 2013/0178428 A1 | 7/2013 | Hoon et al. | |
| 2016/0272712 A1* | 9/2016 | Freeman ................ | C07K 16/30 |
| 2017/0137533 A1 | 5/2017 | Williams et al. | |
| 2018/0327848 A1* | 11/2018 | Ayers ...................... | C12Q 1/68 |

FOREIGN PATENT DOCUMENTS

| | | |
|---|---|---|
| WO | 2007/107748 A2 | 9/2007 |
| WO | 2010/060497 A1 | 6/2010 |
| WO | 2011/041613 A2 | 4/2011 |

OTHER PUBLICATIONS

P. A. Ott et al: "CTLA-4 and PD-1/PD-L1 Blockade: New Immunotherapeutic Modalities with Durable Clinical Benefit in Melanoma Patients", Clinical Cancer Research, vol. 19, No. 19, Oct. 1, 2013, pp. 5300-5309.

Berzofsky et al., "Strategies to use immune modulators in therapeutic vaccines against cancer," Semin Oncol. Jun. 2012; 39(3) 348-57.

Bracci et al., "immune-based mechanisms of cytotoxic chemotherapy: implications for the design of novel and rationale-based combined treatments against cancer," Cell Death and Differentiation (2014) 21, 15-25.

Camilio et al., "Complete regression and systemic protective immune responses obtained in B16 melanomas after treatment with LTX-315," Cancer Immunol Immunother. 2014; 63:601-13.

Camilio et al., "LTX-315 (Oncopore™) A short synthetic anticancer peptide and novel immunotherapeutic agent," Oncoimmunology (2014) 3: e29181.

Camilio, K. "Short Lytic Anticancer Peptides as a Novel Therapy against Cancer," Doctoral thesis, Faculty of Health Sciences Dept of Medical Biology Molecular Inflammation Research Group, Jun. 2013.

Eike et al., "The oncolytic peptide LTX-315 induces cell death and DAMP release by mitochondria distortion in human melanoma cells," Oncotarget. Oct. 27, 2015; 6(33): 34910-34923.

Eliassen et al., "Evidence for a Direct Antitumor Mechanism of Action of Bovine Lactoferricin," Anticancer Research (2002), 22(5): pp. 2703-2710.

Eliassen et al., "The antimicrobial peptide, Lactoferricin B, is cytotoxic to neuroblastoma cells in vitro and inhibits xenograft growth in vivo", Int. J. Cancer (2006) 119, 493-450.

Mellman et al., "Cancer immunotherapy comes of age," Nature 2011, vol. 480, 480-489.

Naidoo et al., "Immune modulation for cancer therapy," British Journal of Cancer (2014) 111, 2214-2219.

Pardoll, "The blockade of immune checkpoints in cancer immunotherapy," Nature 2012, vol. 12, 252-264.

Vanneman, M and Dranoff G., "Combining Immunotherapy and Targeted Therapies in Cancer Treatment," Nat Rev Cancer. Mar. 22, 2012;12(4):237-51.

Investor presentation, DNB Markets Healthcare Conference, Lytix Biopharma, Dec. 11, 2014.

Company brochure, DNB Markets Healthcare Conference, Lytix Biopharma, Oct. 2014.

Camilio, Ketil Andre: "Short Lytic Anticancer Peptides as a Novel Therapy against Cancer", Doctoral thesis, Jun. 9, 2013, p. 37, paragraph 5.

Alizadeh et al., "Doxorubicin Eliminates Myeloid-Derived Suppressor Cells and Enhances the Efficacy of Adoptive T-Cell Transfer in Breast Cancer," Cancer Res. (2014) 74(1); 104?118.

Heylmann et al. "Human CD4+CD25+ Regulatory T Cells are Sensitive to Low Dose Cyclophosphamide: Implications for the Immune Response," PLOS one, (2013) vol. 8, Issue 12, e83384.

Michels et al., "Paclitaxel promotes differentiation of myeloid-derived suppressor cells into dendritic cells in vitro in a TLR4-independent manner," J. Immunotoxicol. (2012) 9(3); 292-300.

Zheng et a, "Using chemo-drugs or irradiation to break immune tolerance and facilitate immunotherapy in solid cancer," I (2015) Cell. Immunol., 294, pp. 54-59.

Clinical trial ID 700238936. A Phase I, Open-label, Multi-arm, Multi-centre, Multi-dose, Dose Escalation Study of LTX-315 as Monotherapy or in Combination With Either Ipilimumab or Pembrolizumab in Patients With Transdermally Accessible Tumours. AdisInsight: Trials (Nov. 23, 2013). (Year: 2013).

Office Action issued in Japanese Patent Application No. 2015-118495 mailed Jan. 22, 2019 with English translation.

* cited by examiner

Tumor free 1/7 = 14%

IMMUNE CHECKPOINT INHIBITOR COMBINATIONS

This application is a Continuation of application Ser. No. 17/366,463 filed on Jul. 2, 2021, which is a Continuation of application Ser. No. 15/534,800 filed on Jun. 9, 2017 (now U.S. Pat. No. 11,083,774), which is a 371 National Stage Application of International Application PCT/EP2015/075722 filed on Nov. 4, 2015, which claims priority to Japanese Application 2015-118495 filed on Jun. 11, 2015, and also claims priority to United Kingdom Application 1506127.8 filed on Apr. 10, 2015, and also claims priority to United Kingdom Application 1422084.2 filed on Dec. 11, 2014. The entire contents of these applications are incorporated herein by reference in their entireties.

This application contains a Sequence listing which has been submitted electronically in xml format and is hereby incorporated by reference in its entirety. Said xml copy, created on May 17, 2024, is named SeqList-084283-0030.xml and is 56,801 bytes in size.

The present invention relates to peptides or peptide like molecules and particularly to combined preparations of such peptides with a further agent, and their uses in therapy, in particular as anti-tumour agents.

The prevalence of cancer in human and animal populations and its role in mortality means there is a continuing need for new drugs which are effective against tumours. Elimination of a tumour or a reduction in its size or reducing the number of cancer cells circulating in the blood or lymph systems may be beneficial in a variety of ways; reducing pain or discomfort, preventing metastasis, facilitating operative intervention, prolonging life.

Genetic and epigenetic alterations that are characteristic of cancers result in antigens that the immune system can recognise and use to differentiate between tumour cells and their healthy equivalents. In principle, this means that the immune system could be a powerful weapon in controlling tumours. However, the reality is that the immune system usually does not provide a strong response to tumour cells. It is of great therapeutic interest to manipulate and therefore harness the immune system in the fight against cancer (Mellman et al. Nature 2011, vol. 480, 480-489).

Various attempts have been made to help the immune system to fight tumours. One early approach involved a general stimulation of the immune system, e.g. through the administration of bacteria (live or killed) to elicit a general immune response which would also be directed against the tumour. This is also called nonspecific immunity.

Recent approaches aimed at helping the immune system specifically to recognise tumour-specific antigens involve administration of tumour-specific antigens, typically combined with an adjuvant (a substance which is known to cause or enhance an immune response) to the subject. This approach requires the in vitro isolation and/or synthesis of antigens, which is costly and time consuming. Often not all the tumour-specific antigens have been identified, e.g. in breast cancer the known antigens are found in 20-30% of the total tumours. The use of tumour-specific vaccines have therefore met with limited success.

There remains a strong need for alternative methods for treating tumours and for alternative methods for inhibiting the growth or formation of secondary tumours.

'Cancer Vaccine' is a term used to describe therapeutic agents which are designed to stimulate the patient's immune system against tumour antigens and lead to an attack on tumour cells and improved patient outcome. Despite the name, cancer vaccines are generally intended to generate or enhance an immune response against an existing cancer, rather than to prevent disease. Again, unlike traditional vaccines against infective agents, a cancer or tumour vaccine may not require administration of a tumour antigen, the administered product may utilise tumour antigens already present in the body as a result of tumour development and serve to modify the immune response to the existing tumour associated antigens (TAAs).

It is recognised that the usual lack of a powerful immune response to TAA is due to a combination of factors. T cells have a key role in the immune response, which is initiated through antigen recognition by the T cell receptor (TCR), and they coordinate a balance between co-stimulatory and inhibitory signals known as immune checkpoints (Pardoll, Nature 2012, vol. 12, 252-264). Inhibitory signals suppress the immune system which is important for maintenance of self-tolerance and to protect tissues from damage when the immune system is responding to pathogenic infection. However, immune suppression reduces what could otherwise be a helpful response by the body to the development of tumours.

This T cell mediated balance of immune stimulation and suppression has, in recent years, led to the adoption of a principle of tumour immunotherapy known as a 'push-pull' approach in which combination therapies could be used to simultaneously enhance the stimulatory factors (push) and reduce the inhibitory factors (pull). A helpful analogy is of a combination therapy which both presses on the accelerator (push) and reduces the brakes (pull). (Berzofsky et al. Semin Oncol. 2012 June; 39(3) 348-57).

For example, cytokines, other stimulatory molecules such as CpG (stimulating dendritic cells), Toll-like receptor ligands and other molecular adjuvants enhance the immune response. Co-stimulatory interactions involving T cells directly can be enhanced using agonistic antibodies to receptors including OX40, CD28, CD27 and CD137. These are all push-type approaches to cancer immunotherapy.

Complementary 'pull' therapies may block or deplete inhibitory cells or molecules and include the use of antagonistic antibodies against what are known as immune checkpoints.

Immune checkpoints include cytotoxic T-lymphocyte antigen 4 (CTLA-4) and programmed cell death protein 1 (PD-1) and antibodies against these are known in the art; ipilimumab was the first FDA-approved anti-immune checkpoint antibody licensed for the treatment of metastatic melanoma and this blocks cytotoxic T-lymphocyte antigen 4 (CTLA-4) (Naidoo et al. British Journal of Cancer (2014) 111, 2214-2219). Cytotoxic T-lymphocyte-associated protein 4, also known as CD152, is a member of the immunoglobulin superfamily, which is expressed on the surface of helper T cells and transmits an inhibitory signal to T cells. Its genomic sequence is known, NCBI Reference Sequence: NG_011502.1, as is its protein sequence NCBI Reference Sequence: NP_005205.2.

The present inventors have established that some peptides known to lyse tumour cells through disturbing and permeabilizing the cell membrane, are also highly effective at attacking organelles such as mitochondria and lysosomes and can cause lysis thereof. This may be achieved at low concentrations which do not cause direct lysis of the cell membranes, although loss of cell membrane integrity is seen eventually even on administration of low doses. At higher doses, these molecules can cause lysis of the cell membrane and then of the membranes of organelles.

The peptides of interest are a sub-set of the group of peptides commonly known as Cationic antimicrobial peptides (CAPs). These are positively charged amphipathic peptides and peptides of this type are found in many species and form part of the innate immune system. The CAP Lactoferricin (LfcinB) is a 25 amino acid peptide which has been shown to have an effect on mitochondria (Eliasen et al. Int. J. Cancer (2006) 119, 493-450). It has now surprisingly been found that the much smaller peptide LTX-315, a 9 amino acid peptide (of the type described in WO 2010/060497), also targets the mitochondria. This was unexpected because this small peptide is much more fast acting (causing cell death after 30 minutes of exposure) compared to LfcinB (which is most effective after 24 hours of exposure) and the small peptide acts against a broader spectrum of cell types, which suggests a direct effect on the plasma membrane.

This disruption of the organelle membrane results in the release of agents therefrom which have a potent immunostimulatory function, such agents are generally known as DAMPs (Damage-associated molecular pattern molecules) and include ATP, Cytochrome C, mitochondrial CpG DNA sequences, mitochondrial formyl peptides, cathepsins (from lysosomes) and HMGB1 (from the nucleus). Lysis of organelles can also result in release of additional tumour-specific antigens (TAAs).

This ability to stimulate the immune response to tumours through disrupting mitochondrial and other organelle membranes makes these peptides highly suitable as "push" agents in combination "push-pull" immunotherapies designed to treat and protect against tumour development.

Thus, in a first aspect, the present invention provides:

A compound, preferably a peptide, having the following characteristics:
  a) consisting of 9 amino acids in a linear arrangement;
  b) of those 9 amino acids, 5 are cationic and 4 have a lipophilic R group;
  c) at least one of said 9 amino acids is a non-genetically coded amino acid (e.g. a modified derivative of a genetically coded amino acid); and optionally
  d) the lipophilic and cationic residues are arranged such that there are no more than two of either type of residue adjacent to one another; and further optionally
  e) the molecule comprises two pairs of adjacent cationic amino acids and one or two pairs of adjacent lipophilic residues;
for use in the treatment of a tumour by combined, sequential or separate administration with an immune checkpoint inhibitor (ICI).

The combination therapy proposed herein may, in certain advantageous embodiments, provide a synergistic effect. Such surprising synergistic effects have been seen, for example, when using an anti-CTLA-4 antibody (Example 11).

The amino acid containing molecules defined above are conveniently referred to herein as the "peptidic compound of the invention", which expression includes all of the peptides and peptidomimetics disclosed herein.

The cationic amino acids, which may be the same or different, are preferably lysine or arginine but may be histidine or any non-genetically coded amino acid carrying a positive charge at pH 7.0. Suitable non-genetically coded cationic amino acids include analogues of lysine, arginine and histidine such as homolysine, ornithine, diaminobutyric acid, diaminopimelic acid, diaminopropionic acid and homoarginine as well as trimethyllysine and trimethylornithine, 4-aminopiperidine-4-carboxylic acid, 4-amino-1-carbamimidoylpiperidine-4-carboxylic acid and 4-guanidinophenylalanine.

Non-genetically coded amino acids include modified derivatives of genetically coded amino acids and naturally occurring amino acids other than the 20 standard amino acids of the genetic code. In this context, a D amino acid, while not strictly genetically coded, is not considered to be a "non-genetically coded amino acid", which should be structurally, not just stereospecifically, different from the 20 genetically coded L amino acids. The molecules of the invention may have some or all of the amino acids present in the D form, preferably however all amino acids are in the L form.

The lipophilic amino acids (i.e. amino acids with a lipophilic R group), which may be the same or different, all possess an R group with at least 7, preferably at least 8 or 9, more preferably at least 10 non-hydrogen atoms. An amino acid with a lipophilic R group is referred to herein as a lipophilic amino acid. Typically the lipophilic R group has at least one, preferably two cyclic groups, which may be fused or linked.

The lipophilic R group may contain hetero atoms such as O, N or S but typically there is no more than one heteroatom, preferably it is nitrogen. This R group will preferably have no more than 2 polar groups, more preferably none or one, most preferably none.

Tryptophan is a preferred lipophilic amino acid and the molecules preferably comprise 1 to 3, more preferably 2 or 3, most preferably 3 tryptophan residues. Further genetically coded lipophilic amino acids which may be incorporated are phenylalanine and tyrosine.

Preferably one of the lipophilic amino acids is a non-genetically coded amino acid. Most preferably the molecule consists of 3 genetically coded lipophilic amino acids, 5 genetically coded cationic amino acids and 1 non-genetically coded lipophilic amino acid.

When the molecules include a non-genetically coded lipophilic amino acid (e.g. amino acid derivative), the R group of that amino acid preferably contains no more than 35 non-hydrogen atoms, more preferably no more than 30, most preferably no more than 25 non-hydrogen atoms.

Preferred non-genetically coded amino acids include: 2-amino-3-(biphenyl-4-yl)propanoic acid (biphenylalanine), 2-amino-3,3-diphenylpropanoic acid (diphenylalanine), 2-amino-3-(anthracen-9-yl)propanoic acid, 2-amino-3-(naphthalen-2-yl)propanoic acid, 2-amino-3-(naphthalen-1-yl)propanoic acid, 2-amino-3-[1,1':4',1''-terphenyl-4-yl]-propionic acid, 2-amino-3-(2,5,7-tri-tert-butyl-1H-indol-3-yl)propanoic acid, 2-amino-3-[1,1':3',1''-terphenyl-4-yl]-propionic acid, 2-amino-3-[1,1':2',1''-terphenyl-4-yl]-propionic acid, 2-amino-3-(4-naphthalen-2-yl-phenyl)-propionic acid, 2-amino-3-(4'-butylbiphenyl-4-yl)propanoic acid, 2-amino-3-[1,1':3',1''-terphenyl-5'-yl]-propionic acid and 2-amino-3-(4-(2,2-diphenylethyl)phenyl)propanoic acid.

In a preferred embodiment the peptidic compounds of the invention have one of formulae I to V listed below, in which C represents a cationic amino acid as defined above and L represents a lipophilic amino acid as defined above. The amino acids being covalently linked, preferably by peptide bonds resulting in a true peptide or by other linkages resulting in a peptidomimetic, peptides being preferred. The free amino or carboxy terminals of these molecules may be modified, the carboxy terminus is preferably modified to remove the negative charge, most preferably the carboxy terminus is amidated, this amide group may be substituted.

(I) CCLLCCLLC (SEQ ID NO: 1)

(II) LCCLLCCLC (SEQ ID NO: 2)

(III) CLLCCLLCC (SEQ ID NO: 3)

(IV) CCLLCLLCC (SEQ ID NO: 4)

(V) CLCCLLCCL (SEQ ID NO: 5)

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46, 47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds may have 9 identifiable sub-units which are approximately equivalent in size and function to the 9 cationic and lipophilic amino acids. The term 'amino acid' may thus conveniently be used herein to refer to the equivalent sub-units of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in "Drug Design and Development", Krogsgaard et al., 1996, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein just the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

β and γ amino acids as well as α amino acids are included within the term 'amino acids', as are N-substituted glycines. The peptidic compounds of the invention include beta peptides and depsipeptides.

As discussed above, the peptidic compounds of the invention incorporate at least one, and preferably one, non-genetically coded amino acid. When this residue is denoted L', preferred compounds are represented by the following formulae:

(I') CCL'LCCLLC (SEQ ID NO: 6)

(I") CCLLCCLL'C (SEQ ID NO: 7)

(I''') CCLL'CCLLC (SEQ ID NO: 8)

(II') LCCLL'CCLC (SEQ ID NO: 9)

Particularly preferred are compounds (preferably peptides) of formula I and II, and of these, compounds (preferably peptides) of formula I" are especially preferred.

The following peptides as presented in Table 1 are most preferred.

TABLE 1

| Name | SEQ ID NO | Sequence |
|---|---|---|
| LTX-301 | 10 | Dip-K-K-W-W-K-K-W-K-NH$_2$ |
| LTX-302 | 11 | W-K-K-W-Dip-K-K-W-K-NH$_2$ |
| LTX-303 | 12 | W-K-K-W-W-K-K-Dip-K-NH$_2$ |
| LTX-304 | 13 | Bip-K-K-W-W-K-K-W-K-NH$_3$ |
| LTX-305 | 14 | W-K-K-Bip-W-K-K-W-K-NH$_2$ |
| LTX-306 | 15 | w-k-k-w-dip-k-k-w-k-NH$_2$ |
| LTX-307 | 16 | K-K-W-Dip-K-K-W-W-K-NH$_2$ |
| LTX-308 | 17 | k-k-W-Dip-k-k-W-W-k-NH$_2$ |
| LTX-309 | 18 | K-K-W-Dip-K-K-W-Dip-K-NH$_2$ |
| LTX-310 | 19 | K-K-W-Bip-K-K-W-W-K-NH$_2$ |
| LTX-312 | 20 | K-Bip-K-K-W-W-K-W-K-NH$_2$ |

TABLE 1-continued

| Name | SEQ ID NO | Sequence |
|---|---|---|
| LTX-313 | 21 | K-K-Bip-W-K-K-W-W-K-NH$_2$ |
| LTX-314 | 22 | K-K-W-W-K-K-Dip-W-K-NH$_2$ |
| LTX-315 | 23 | K-K-W-W-K-K-W-Dip-K-NH$_2$ |
| LTX-316 | 24 | K-W-Dip-K-K-W-W-K-K-NH$_2$ |
| LTX-317 | 25 | K-K-W-W-K-W-Dip-K-K-NH$_2$ |
| LTX-318 | 26 | Orn-Orn-W-Dip-Orn-Orn-W-W-Orn-NH$_2$ |
| LTX-319 | 27 | Dap-Dap-W-Dip-Dap-Dap-W-W-Dap-NH$_2$ |
| LTX-320 | 28 | R-R-W-Dip-R-R-W-W-R-NH$_2$ |
| LTX-321 | 29 | K-W-W-K-K-Dip-W-K-K-NH$_2$ |
| LTX-323 | 30 | K-Dip-K-K-W-W-K-K-W-NH$_2$ |
| LTX-324 | 31 | K-K-Dip-W-K-K-W-W-K-NH$_2$ |
| LTX-325 | 32 | k-w-w-k-k-dip-w-k-k-NH$_2$ |
| LTX-326 | 33 | R-R-Bip-W-R-R-W-W-R-NH$_2$ |
| LTX-327 | 34 | R-R-Dip-W-R-R-W-W-R-NH$_2$ |
| LTX-329 | 35 | k-k-bip-w-k-k-w-w-k-NH$_2$ |
| LTX-331 | 36 | k-k-Bip-w-k-k-w-w-k-NH$_2$ |
| LTX-332 | 37 | K-K-bip-W-K-K-W-W-K-NH$_2$ |
| LTX-333 | 38 | Dab-Dab-W-Dip-Dab-Dab-W-W-Dab-NH$_2$ |
| LTX-334 | 39 | K-K-W-1-Nal-K-K-W-W-K-NH$_2$ |
| LTX-335 | 40 | K-K-W-2-Nal-K-K-W-W-K-NH$_2$ |
| LTX-336 | 41 | K-K-W-Ath-K-K-W-W-K-NH$_2$ |
| LTX-338 | 42 | K-K-W-Phe(4-4'Bip)-K-K-W-W-K-NH$_2$ |

In which:
the standard single letter code is used for the genetically coded amino acids
lower case denotes D amino acids
Dip is diphenylalanine
Bip is biphenylalanine
Orn is ornithine
Dap is 2,3-diaminopropionic acid
Dab is 2,4-diaminobutyric acid
1-Nal is 1-naphthylalanine
2-Nal is 2-naphthylalanine
Ath is 2-amino-3-(anthracen-9-yl)propanoic acid
Phe(4,4'Bip) is 2-amino-3-[1,1':4',1''-terphenyl-4-yl]propionic acid
Compound LTX-315 is most preferred.

All of the molecules described herein may be in salt, ester or amide form.

The molecules are preferably peptides and preferably have a modified, particularly an amidated, C-terminus. Amidated peptides may themselves be in salt form and acetate forms are preferred. Suitable physiologically acceptable salts are well known in the art and include salts of inorganic or organic acids, and include trifluoracetate as well as acetate and salts formed with HCl.

The peptidic compounds described herein are amphipathic in nature, their 2° structure, which may or may not tend towards the formation of an α-helix, provides an amphipathic molecule in physiological conditions.

The combination therapies defined herein are for the treatment of tumours, in particular solid tumours and thus for the treatment of cancer.

The peptidic compounds of the invention destabilise and/or permeabilise the membranes of tumour cell organelles, e.g. mitochondria, the nucleus or lysomome, in particular the mitochondria.

By 'destabilising' is meant a perturbation of the normal lipid bi-layer configuration including but not limited to membrane thinning, increased membrane permeability to water, ions or metabolites etc.

Immune checkpoints are known in the art (Naidoo et al. and Pardoll et al supra) and the term is well understood in the context of cancer therapy. The most well-known are CTLA-4, PD-1 and its ligand PDL-1. Others include TIM-3, KIR, LAG-3, VISTA, BTLA. Inhibitors of immune checkpoints inhibit their normal immunosuppressive function, for example by down regulation of expression of the checkpoint molecules or by binding thereto and blocking normal receptor/ligand interactions. As the immune checkpoints put brakes on the immune system response to an antigen, so an inhibitor thereof reduces this immunosuppressive effect and enhances the immune response. Inhibitors of immune checkpoints are known in the art and preferred are anti-immune checkpoint antibodies, such as anti-CTLA-4 antibodies (e.g. ipilimumab and tremelimumab), anti-PD-1 antibodies (e.g. nivolumab, pembrolizumab, formerly known as lambrolizumab, pidilizumab and RG7446 (Roche)) and anti-PDL-1 antibodies (e.g. BMS-936559 (Bristol-Myers Squibb), MPDL3280A (Genentech), MSB0010718C (EMD-Serono) and MEDI4736 (AstraZeneca)).

Thus preferred ICIs are antibodies that bind to a specific immune checkpoint molecule, whether that immune checkpoint molecule is itself a receptor or a ligand therefor. Preferred immune checkpoint molecules are listed above. Receptors which form part of an immune checkpoint are typically found on the surface of T cells.

With knowledge of an immune checkpoint target, a skilled man is able to develop an inhibitor thereof. Inhibitors may be selected from proteins, peptides, peptidomimetics, peptoids, antibodies, antibody fragments, small inorganic molecules, small non-nucleic acid organic molecules or nucleic acids such as anti-sense nucleic acids, small interfering RNA (siRNA) molecules or oligonucleotides. Thus the inhibitor may act to down regulate expression of an immune checkpoint molecule. The inhibitor may for example be a modified version of the natural ligand (e.g. for CTLA-4, CD80 (B7-1) and CD86 (B7-2)), such as a truncated version of one of the ligands. They may be naturally occurring, recombinant or synthetic.

Preferably the inhibitor is either an antibody, a modified ligand or an antisense nucleic acid molecule such as siRNA designed to inhibit a particular immune checkpoint molecule. Preferably the siRNA is capable of preventing or prevents the translation of the immune checkpoint, thus preventing the expression of the protein. Given that the genomic sequence of many immune checkpoints are known, the skilled person would be able to use routine methods to design suitable inhibitory antisense nucleic acid molecules.

Inhibitors of CTLA-4, PD-1 and PD-L1 are preferred and antibodies thereto are particularly preferred. Such antibodies are known as immune checkpoint-blocking antibodies and can invigorate the antitumour immune response.

The invention provides methods of treating a tumour and a method of treating tumour cells. The combination therapy should be effective to kill all or a proportion of the target tumour cells or to prevent or reduce their rate of multiplication, or to inhibit metastasis or otherwise to lessen the harmful effect of the tumour on the patient. The clinician or patient should observe improvement in one or more of the parameters or symptoms associated with the tumour. Administration may also be prophylactic and this is encompassed by the term "treatment". The patient will typically be a human patient but non-human animals, such as domestic or livestock animals may also be treated.

Cancer targets include melanomas, sarcomas, lymphomas, leukemias, neuroblastomas and glioblastomas (e.g. from the brain), carcinomas and adenocarcinomas. Cancers of the breast, colon, bladder, kidney, liver (e.g. hepatocellular carcinoma), lung, ovary, pancreas, prostate and skin) are preferred targets. Head and neck cancers are also preferred targets. Melanomas, sarcomas and lymphomas are preferred targets. Tumours for treatment are typically solid tumours and may be metastatic lesions that are accessible for transdermal injection.

The peptides may be synthesised in any convenient way. Generally the reactive groups present (for example amino, thiol and/or carboxyl) will be protected during overall synthesis. The final step in the synthesis will thus be the deprotection of a protected derivative of the invention. In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art. A wide choice of protecting groups for amino acids which are used in the synthesis of peptides are known.

References and techniques for synthesising peptidomimetic compounds and the other bioactive molecules of the invention are described herein and are well known in the art.

While it is possible for the peptidic compounds (including salts, esters or amides thereof) to be administered as pure compounds, it is preferable to present them as pharmaceutical formulations, i.e. incorporating one or more pharmaceutically acceptable diluents, carriers or excipients.

The active agents according to the invention may be presented, for example, in a form suitable for oral, topical, nasal, parenteral, intravenal, intratumoral, rectal or regional (e.g. isolated limb perfusion) administration. Unless otherwise stated, administration is typically by a parenteral route, preferably by injection subcutaneously, intramuscularly, intracapsularly, intraspinally, intraperitoneally, intratumourally, transdermally or intravenously. For the peptidic compound, administration is preferably intratumoural. Particularly preferred are intratumoural injections of the peptidic compound of the invention once a day for several consecutive days, e.g. 2, 3, 4, 5, 6 or 7 days, preferably on 2-4 consecutive days or at 2, 3, 4, 5, 6 or 7 daily intervals, e.g. 2-4 times at 5, 6, 7, 8 or 9 daily intervals.

For the checkpoint inhibitor, administration is preferably intravenous or intralesional.

The peptidic compound may be administered with or after the immune checkpoint inhibitor, as has been shown to be effective with respect to anti-PD1 and anti-CTLA4 antibodies. Alternatively the peptidic compound may be administered with or before the immune checkpoint inhibitor, as has been shown to be effective with respect to anti-CTLA4 and anti-PD-L1 antibodies. There are preferably multiple administrations. The immune system is preferably stimulated over time. For example, administrations of the peptidic compound and/or the checkpoint inhibitor may be carried out over the course of eight months, preferably four months, more preferably two months; in such regimens administration is preferably weekly. Thus there may be 2 to 40, preferably 3 to 30, e.g. 6 to 30 or 6 to 20 administrations.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms. Simple solutions are preferred.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Preferred formulations are those in which the molecules are in saline. Such formulations being suitable for use in preferred methods of administration, especially local administration, i.e. intratumoural, e.g. by injection.

Unless otherwise stated, dosage units containing the peptidic molecules preferably contain 0.1-10 mg, for example 1-5 mg. The formulation may additionally comprise further active ingredients, including other cytotoxic agents such as other anti-tumour peptides. Other active ingredients may include different types of cytokines e.g. IFN-γ, TNF, CSF and growth factors, immunomodulators, chemotherapeutics e.g. cisplatin or antibodies or cancer vaccines.

Also provided according to the present invention is the use of a peptidic compound as defined above in the manufacture of a medicament for the treatment of a tumour, wherein said peptidic compound is co-administered with a checkpoint inhibitor as defined above.

Preferably, the medicament is for the treatment of multidrug resistant (MDR) tumours.

Also provided according to the present invention is a pharmaceutical pack or composition comprising:
  (i) a peptidic compound as defined herein; and
  (ii) a checkpoint inhibitor as described herein.

With pharmaceutical packs, the components can be for administration separately. The pharmaceutical pack can of course also comprise instructions for administration. The pack and composition are for use in the treatment of a tumour.

Also provided according to the present invention is a method of treatment of a tumour, comprising the step of administering a peptidic compound as defined herein and a checkpoint inhibitor as described herein, together in pharmaceutically effective amounts, to a patient in need of same.

As discussed above, the peptidic compounds of the invention are able to destabilise mitochondrial membranes and cause release of DAMPs and antigenic material. This can have a powerful positive effect on the immune system's response to cancer cells. In certain cancer treatments, the immune response is of primary importance, e.g. to treat unidentified secondary tumours, to prevent formation of metastatic tumours, when surgery or other direct intervention is not possible. Different cancers are more or less immunogenic and therefore in some scenarios boosting the immune response to cancer is vital.

Thus, in a further aspect, the present invention provides a peptidic compound as defined herein for use in the destabilisation of a mitochondrial membrane, wherein said use is in the treatment of a tumour. This can be regarded as an immunotherapeutic use or treatment and the tumour will typically be cancerous. Preferred features and embodiments discussed elsewhere in relation to the combination therapies apply, mutatis mutandis, to this aspect.

In a further aspect the invention provides a composition comprising or consisting of a peptidic compound of the invention and an immunotherapeutic agent. In a further aspect the invention provides a method of treating tumours in a patient, said method comprising administration of an effective amount of a peptidic compound of the invention and simultaneous or sequential administration of an effective amount of an immunotherapeutic agent.

Alternatively viewed, there is provided a peptidic compound of the invention and an immunotherapeutic agent for use in the treatment of tumours.

By "immunotherapeutic agent" is meant an agent which modulates the immune response. Preferably, the immunotherapeutic agent enhances the immune response against one or more tumor antigens, for example by suppressing (preferably selectively) Treg cells and or MDSCs and/or by blocking cytotoxic T lymphocyte antigen-4 (CTLA-4), an inhibitory receptor expressed on T cells. In all aspects and embodiments of the invention, the immunotherapeutic agent is preferably an anti-CTLA-4 agent.

The skilled person would be able to select suitable dosages of the immunotherapeutic agent.

The immunotherapeutic agent, e.g. the immune checkpoint inhibitor such as an anti-CTLA-4 agent, is preferably administered prior to or simultaneously with the peptidic compound of the invention, it is most preferred that it is administered prior to the first administration of the peptidic compound of the invention. Preferably, it is administered prior to the peptidic compound of the invention, e.g. 1, 2, 3, 4, 5, 6, 7, 8, 9, or 10 days prior to the peptidic compound of the invention. Preferably the first peptidic administration is 1 or 2 days after the last ICI administration. There may be 1 to 8 ICI administrations, e.g. 2 to 4 administrations given 2, 3 or 4 days apart. Multiple doses may be used, which may be e.g. 1, 2, 3, 4, 5, 6, 7, 8, 9, 10 days apart.

For example, the anti-CTLA-4 agent ipilimumab is typically administered once every three weeks for a total of four doses. The anti-PD1 agent nivolumab is typically administered every second week, and the anti-PD1 agent pembrolizumab, formerly known as lambrolizumab, is typically administered every third week. Such dosage regimens are preferable.

Anti-PD-L1 is preferably administered at the same time or after the peptidic compound.

In some embodiments the peptidic compound is administered on the same day as the first dose of the immunotherapeutic agent, followed by weekly administrations for four to eight weeks, e.g. six weeks, as part of an induction phase. The peptidic compound may then be administered every second week thereafter as part of a maintenance phase.

Co-administration may be simultaneous or sequential and by the same or different routes of administration, e.g. oral and/or parenteral, or i.p. for the ICI and intra-tumoural for the peptidic compound.

There is further provided a product containing a peptidic compound of the invention and an immunotherapeutic agent as a combined preparation for separate, simultaneous or sequential use in treating tumours.

The inventors have also surprisingly found that the treatment of a tumour with a peptidic compound of the invention in conjunction with an immunotherapeutic agent can induce an adaptive immunity against further tumours. The above methods, uses and products (compositions) may therefore optionally extend to the induction of an adaptive immunity against further tumours. Thus, for example, the invention also provides a peptidic compound of the invention and an immunotherapeutic agent for use in the treatment of tumours in a patient and inducing adaptive immunity against tumour growth, development or establishment in said patient.

Thus, in a further aspect, there is provided a method of inducing adaptive immunity against tumour growth, development or establishment in a patient, said method comprising administration of an effective amount of a peptidic compound of the invention and simultaneous or sequential administration of an effective amount of an immunotherapeutic agent.

Alternatively viewed, the invention provides a peptidic compound of the invention and an immunotherapeutic agent for use in inducing an adaptive immunity against tumour growth, development or establishment.

Alternatively viewed, there is provided the use of a peptidic compound of the invention and an immunotherapeutic agent in the manufacture of a medicament for use as a vaccine against tumour growth, development or establishment.

Thus, there is provided a product containing a peptidic compound of the invention and an immunotherapeutic agent as a combined preparation for separate, simultaneous or sequential use in inducing an adaptive immunity against tumour growth, development or establishment.

The invention also provides a method of vaccinating a subject against tumour growth, development or establishment through administration of an effective amount of a peptidic compound of the invention and an immunotherapeutic agent to said patient. Reference to a 'vaccine' and 'vaccinating' both imply a prophylactic effect, thus while there may be beneficial direct treatment of existing tumours, a significant motivation in this aspect of the invention is the prevention or reduction in future tumour growth or development.

Figure 2:
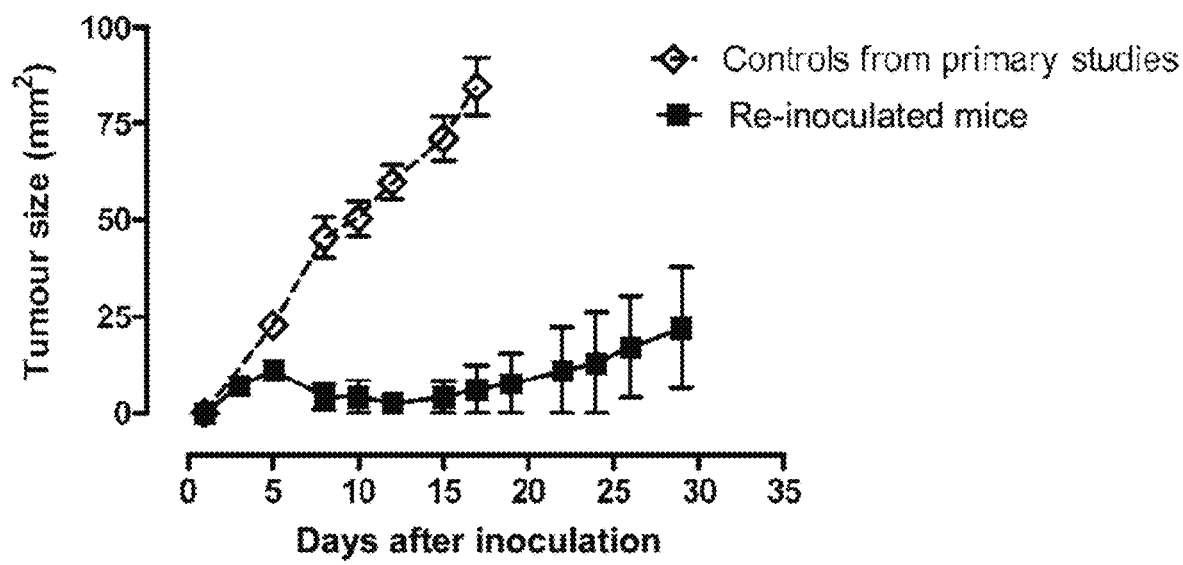
Figure 3:
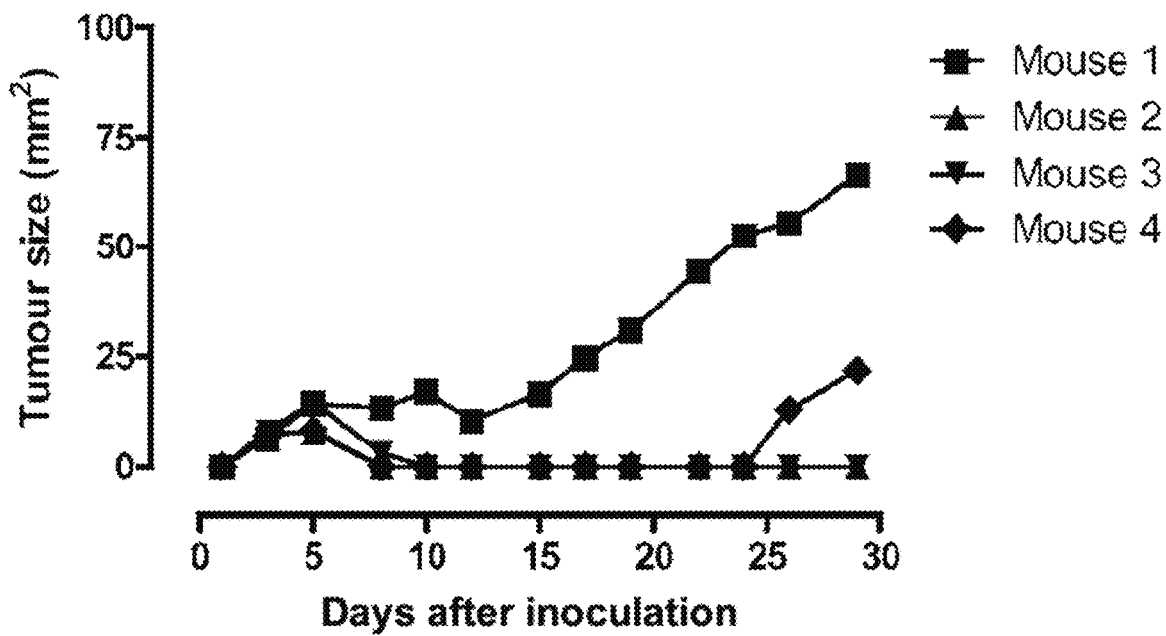
Figure 4:
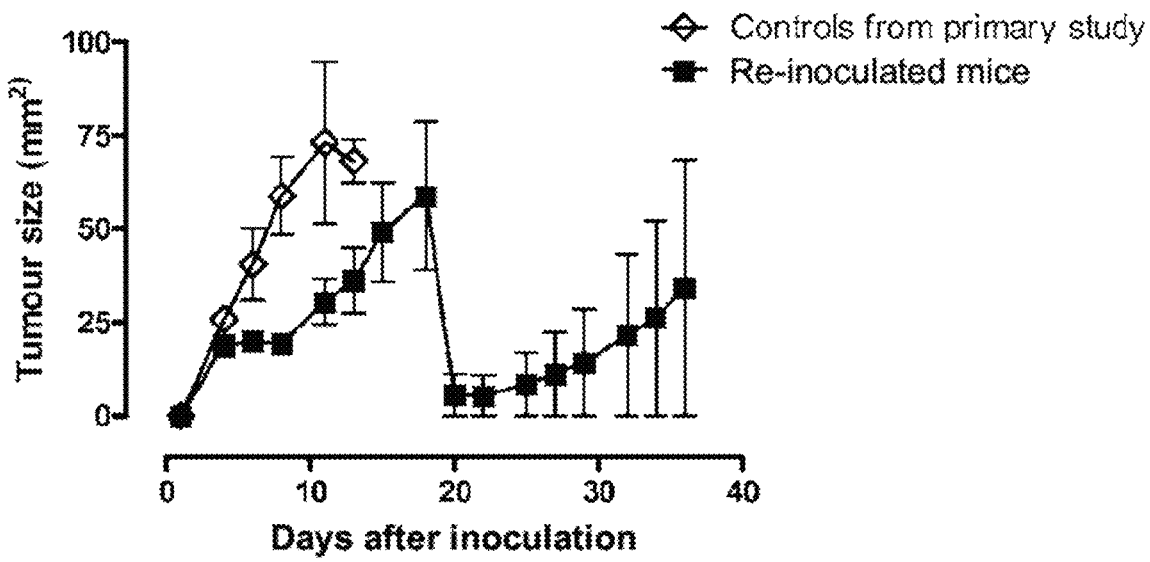
Figure 5:
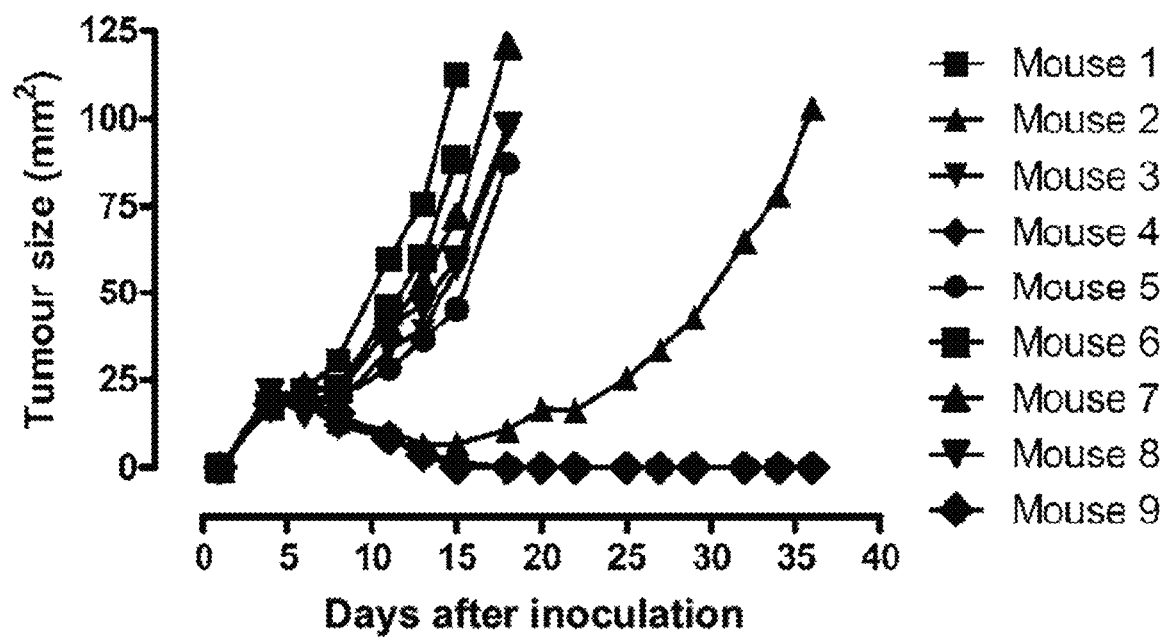
Figure 6:
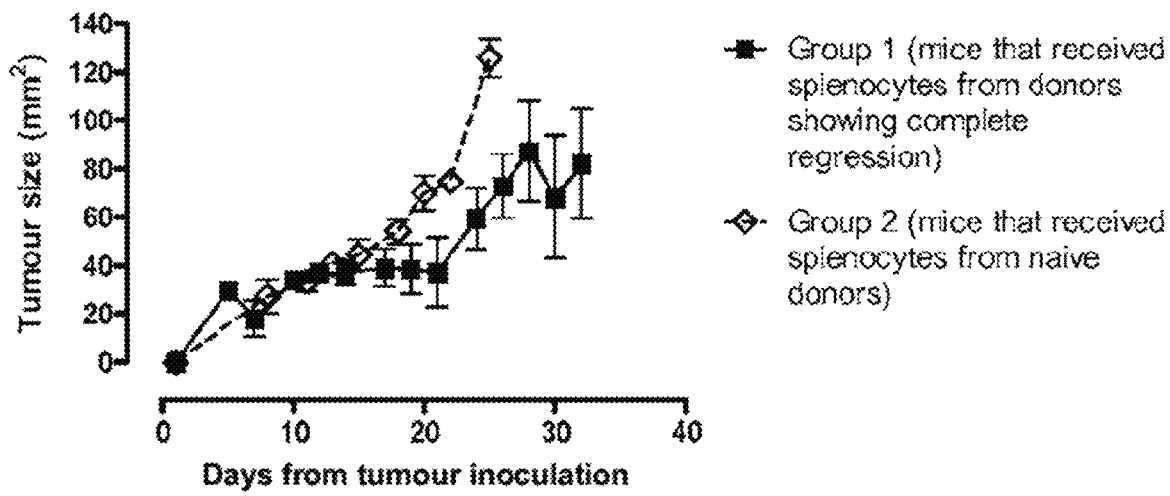
Figure 7:
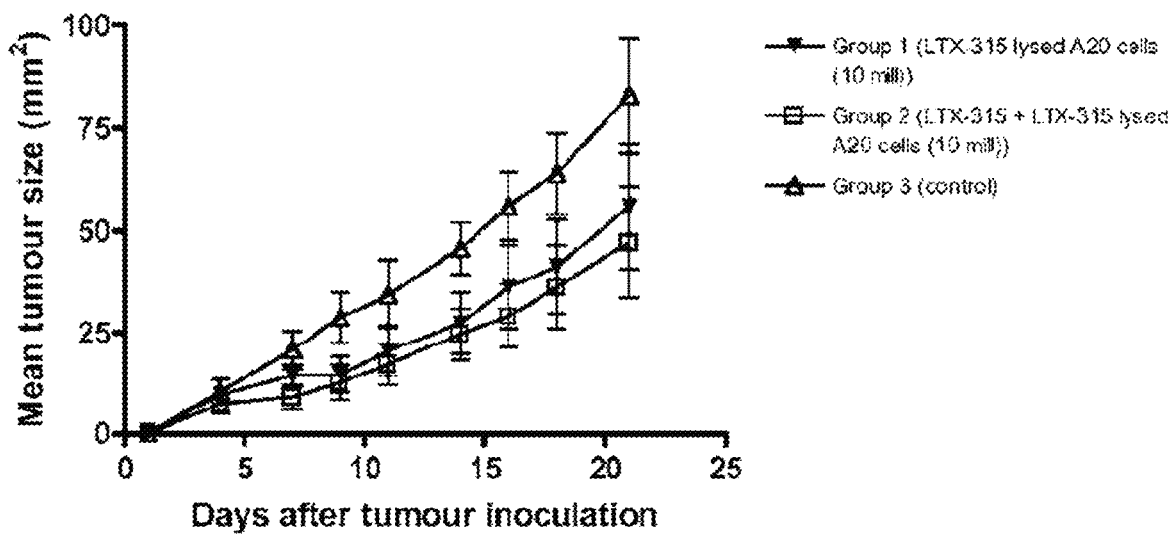

The invention will now be further described in the following Examples and with reference to the figures in which:

FIG. 1 is a graph showing the percentage of red blood cell death in a series of experiments to test peptide LTX-315 at varying concentrations. X-axis shows peptide concentration (µg/ml). Y-axis shows % cell death;

FIG. 2 shows tumour growth in mice re-inoculated with murine A20 B cell lymphoma cells compared with growth in the control animals from the initial study. Diamonds indicate controls from primary studies. Solid squares indicate re-inoculated mice;

FIG. 3 shows tumour growth in individual mice re-inoculated with murine A20 B cell lymphoma cells having been initially treated with LTX-315. Squares indicate Mouse 1. Triangles (base at bottom) indicate Mouse 2. Triangles (base at top) indicate Mouse 3. Diamonds indicate Mouse 4;

FIG. 4 shows tumour growth in mice re-inoculated with murine CT26WT colon carcinoma cells compared with growth in the control animals. Diamonds indicate controls from primary studies. Solid squares indicate re-inoculated mice;

FIG. 5 shows tumour growth in individual mice re-inoculated with murine CT26WT colon carcinoma cells having been initially treated with LTX-315. Small squares indicate Mouse 1. Small triangles (base at bottom) indicate Mouse 2. Small triangles (base at top) indicate Mouse 3. Small diamonds indicate Mouse 4; Circles indicate Mouse 5. Large squares indicate Mouse 6. Large triangles (base at bottom) indicate Mouse 7. Large triangles (base at top) indicate Mouse 8. Large diamonds indicate Mouse 9;

FIG. 6 shows growth of A20 B-cell lymphomas in irradiated mice that received splenocytes from donor mice showing complete tumour regression following treatment with LTX-315 (Group 1) or control mice (Group 2) that received splenocytes from naïve donor mice. Squares indicate Group 1 (mice that received splenocytes from donors showing complete regression). Diamonds indicate Group 2 (mice that received splenocytes from naive donors);

FIG. 7 shows anti-cancer effect of two different treatment regimes on solid murine A20 tumours (Groups 1 and 2) as compared to non-treated controls (Group 3). Inverted solid triangles (base at top) indicate Group 1 (treatment). Open squares indicate Group 2 (treatment+adjuvant). Open triangles (base at bottom) indicate Group 3 (control). Order of tumour size (mm$^2$) at Day 21 is (largest to smallest): Group 3, Group 1, Group 2.

Figure 8A:
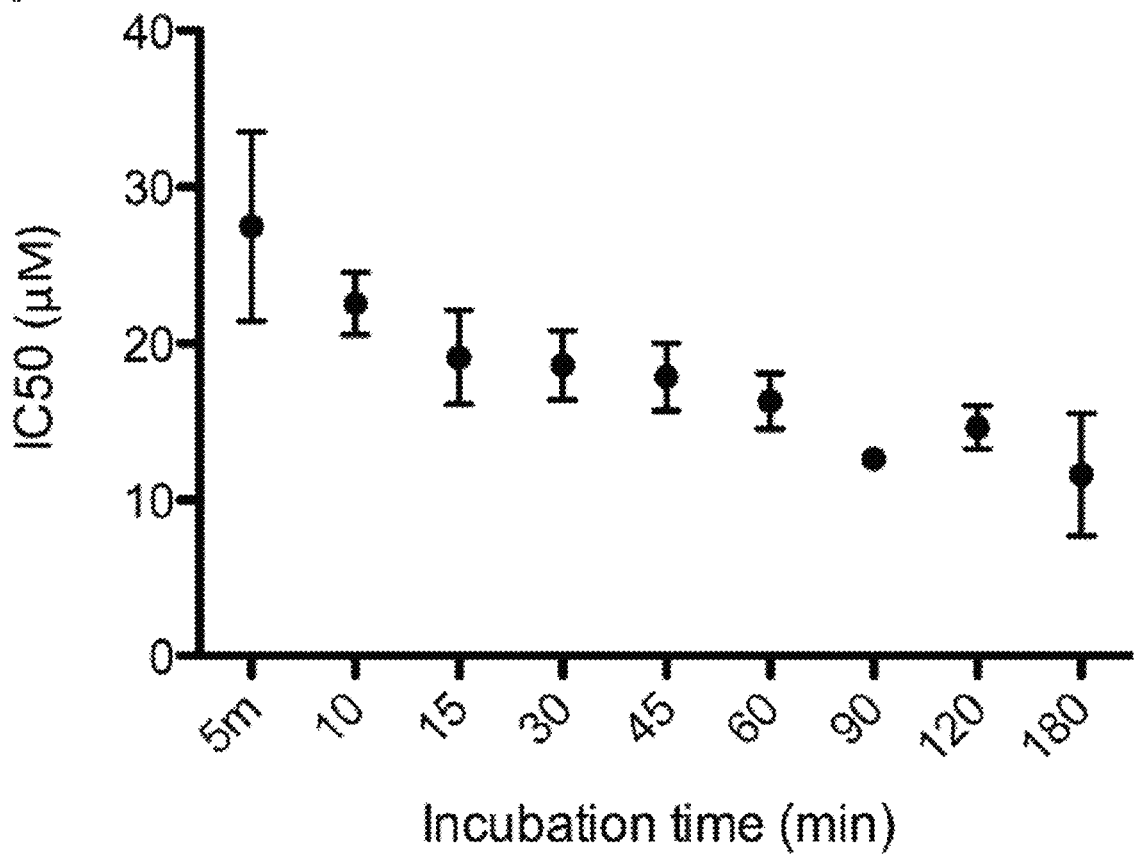
Figure 8B:
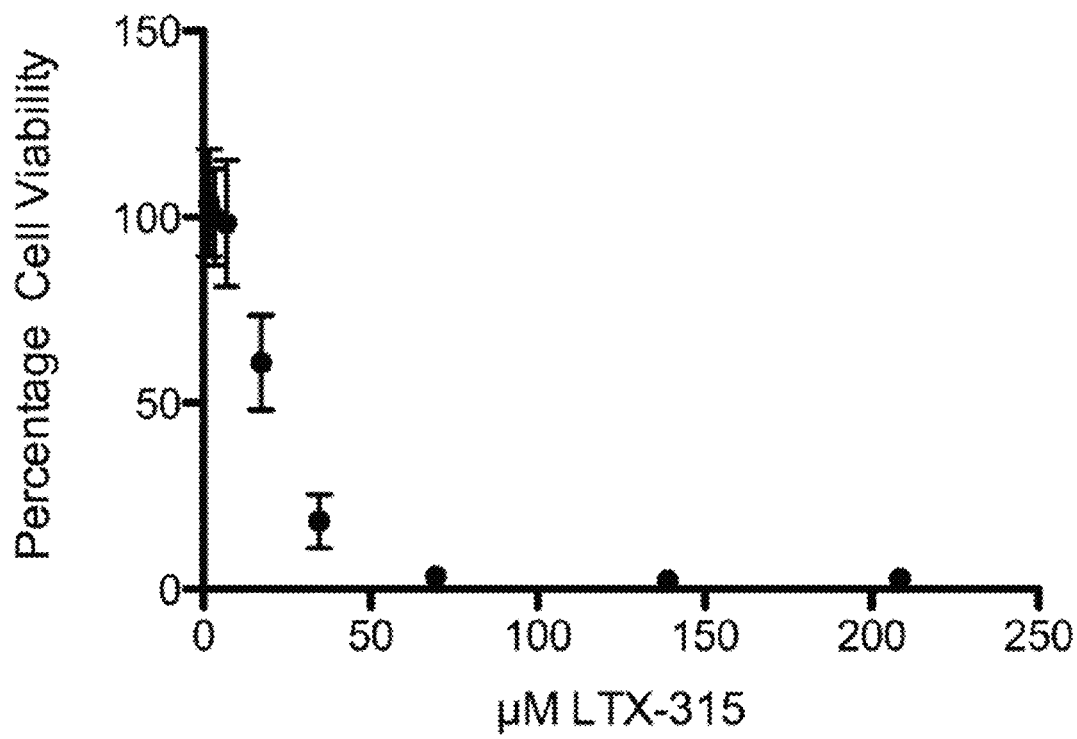

FIGS. 8a-8b LTX-315 causes rapid cell death in human melanoma cells. In vitro cell-killing kinetics of LTX-315 against human melanoma cell line A375 measured with MTT. Results from three experiments are presented for each time point as mean±SD. FIG. 8a shows IC$_{50}$ values at different incubation times. FIG. 8b shows percentage cell viability at different concentrations of L TX-315.

Figure 9:
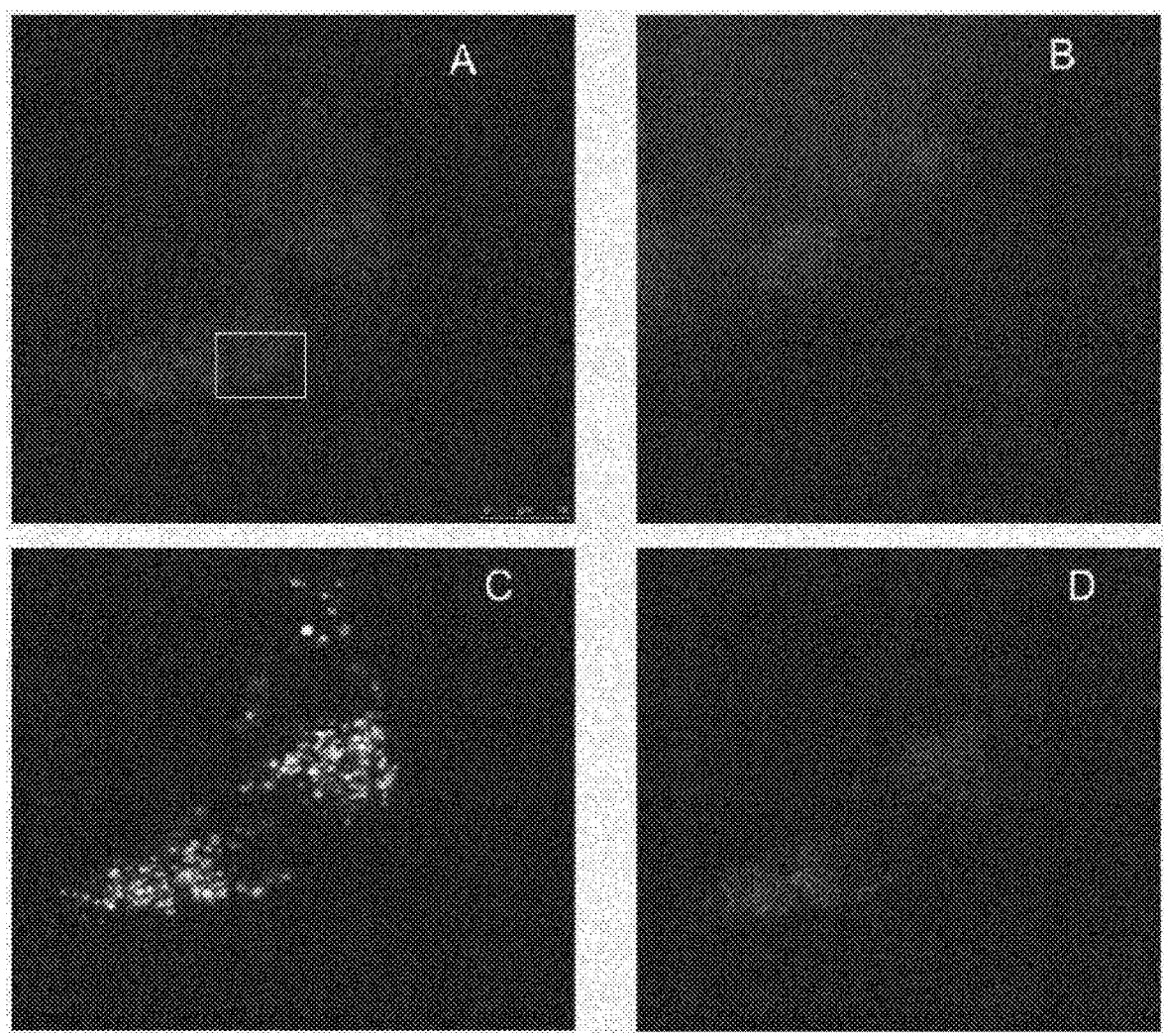

FIG. 9 LTX-315 internalizes and accumulates close to the mitochondria. A375 cells treated 30 minutes with 1.5 μM fluorescence-labeled LTX-315, and with labeled mitochondria and nucleus. The peptide was internalized and detected in close proximity to the mitochondria. A: overlay channels, B: close up, C: mitochondria. D: peptide FIG. 10 Internalization occurs only in lytic 9-mer compounds such as LTX-315 and not in the non-lytic mock peptide LTX-328. A375 cells treated with 3 μM LTX-315 or LTX-328 peptide for 60 min. LTX-315 was detected in the cytoplasm, while LTX-328 was not internalized. A: LTX-315 60 min incubation, B: LTX-328 60 min incubation.

Figure 11:
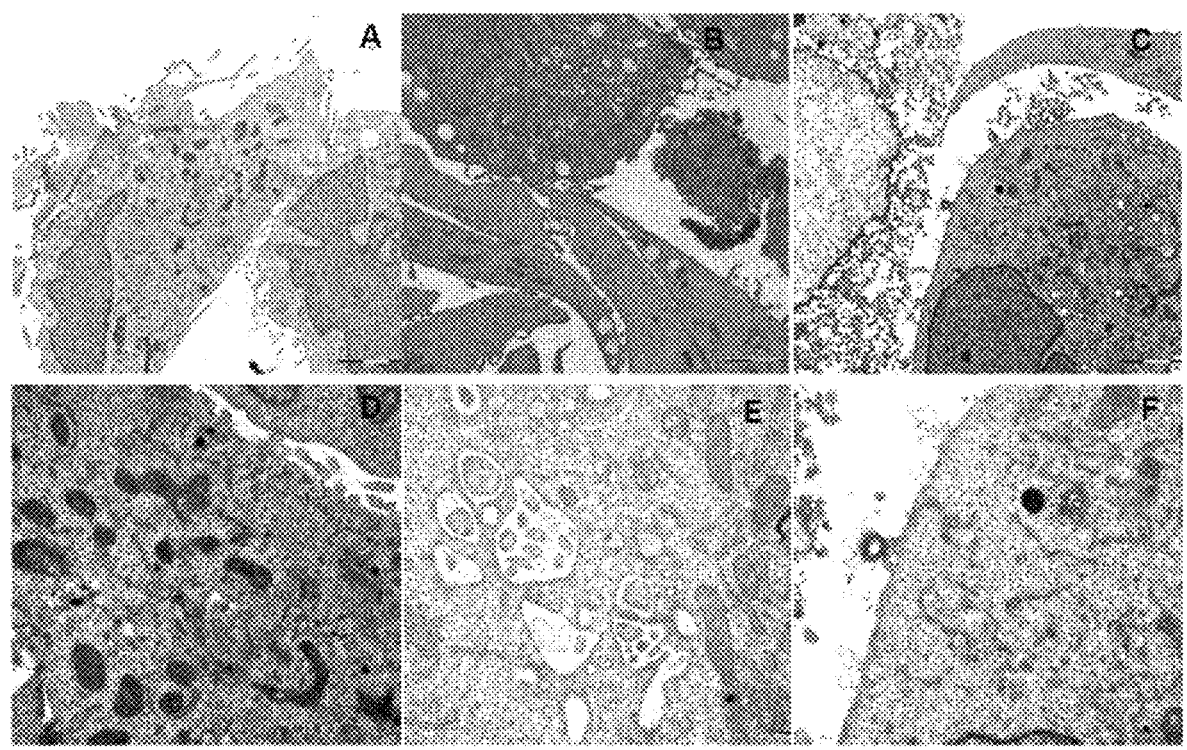

FIG. 11 LTX-315 treatment causes ultrastructural changes. TEM images of A375 cells treated with LTX-315 for 60 minutes compared to control cells. A&D: untreated control cells, B&E: cells treated with 3.5 μM, C:&F cells treated with 17 μM. Magnification 10 000×A-C, 30 000 D-F, scale bar 5 μm.

Figure 12:
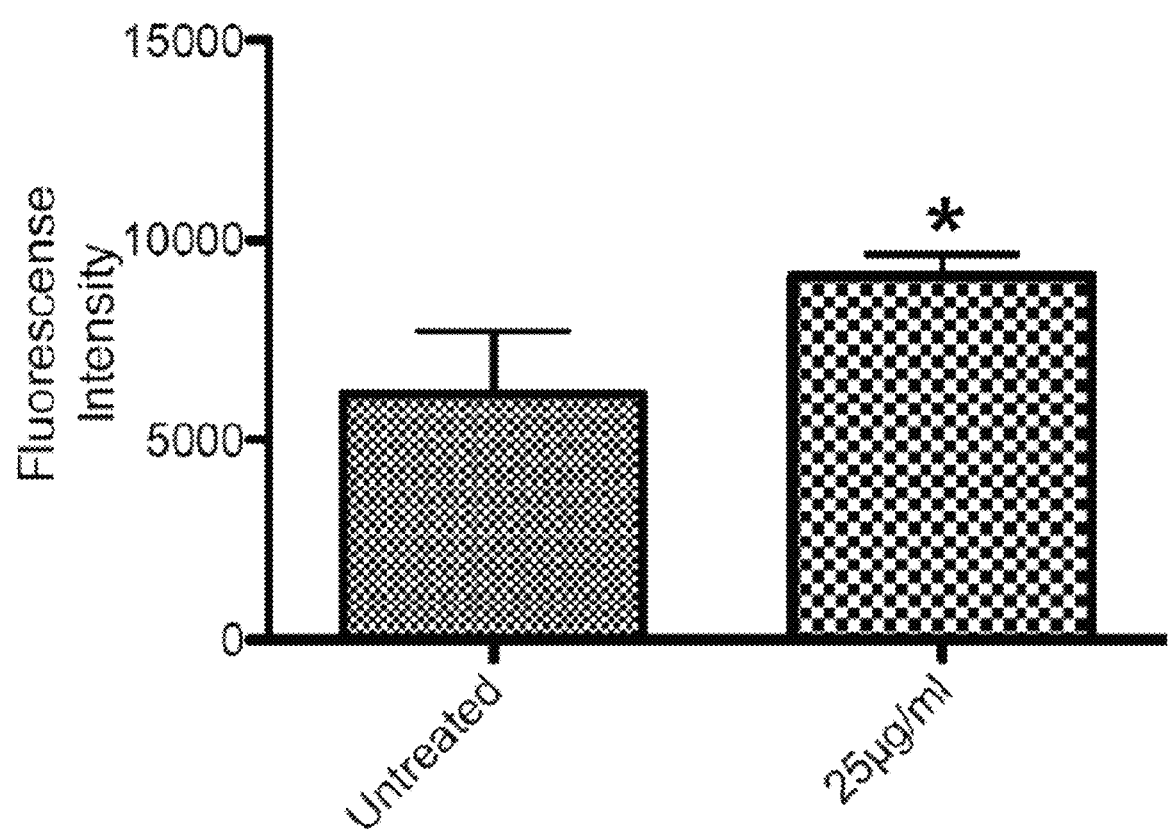

FIG. 12 ROS generation in LTX-315 induced cell death. A375 cells were treated with LTX-315 at different concentrations for 15 minutes. After peptide treatment, carboxy-H2DCFDA was added to the samples and fluorescence was analyzed with a fluorescence plate reader. The experiment was conducted in duplicate, with bars representing mean fluorescence+−S.D.

Figure 13:
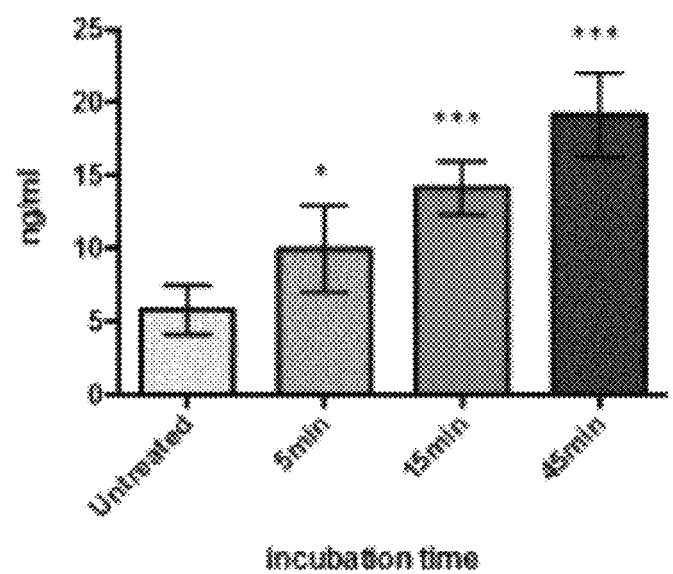

FIG. 13 Human melanoma cells treated with LTX-315 release cytochrome-C in the supernatant. Cytochrome-C release in the supernatant after LTX-315 treatment of A375 after designated time points (5, 15, 45 min) were determined by ELISA assay.

Figure 14:
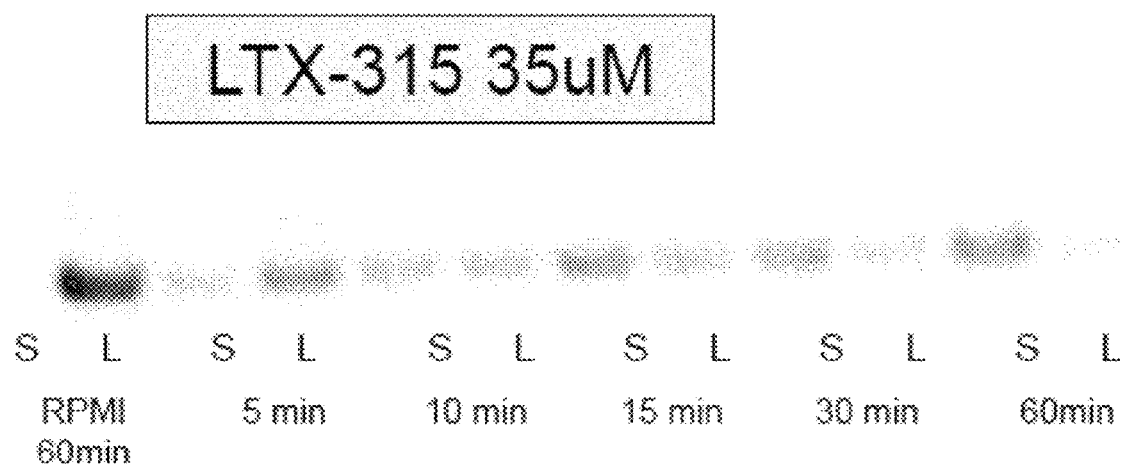
Figure 14:
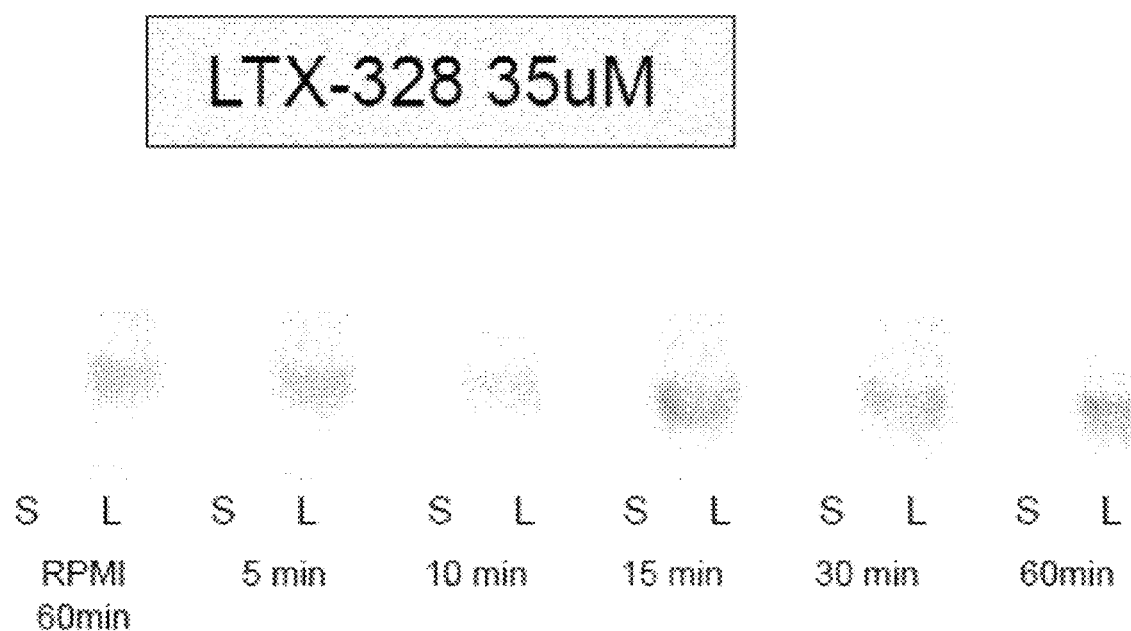

FIG. 14 HMGB 1 is released in the supernatant after LTX-315 treatment. A375 human melanoma cells were treated with 35 μM LTX-315 (top) or LTX-328 (bottom), and cell lysate (L) and supernatant (S) were analyzed with Western blot, and the LTX-315-treated cells showed a gradual translocation from the cell lysate to the cell supernatant. Control cells were treated with media alone, and showed no translocation after 60 minutes.

Figure 15:
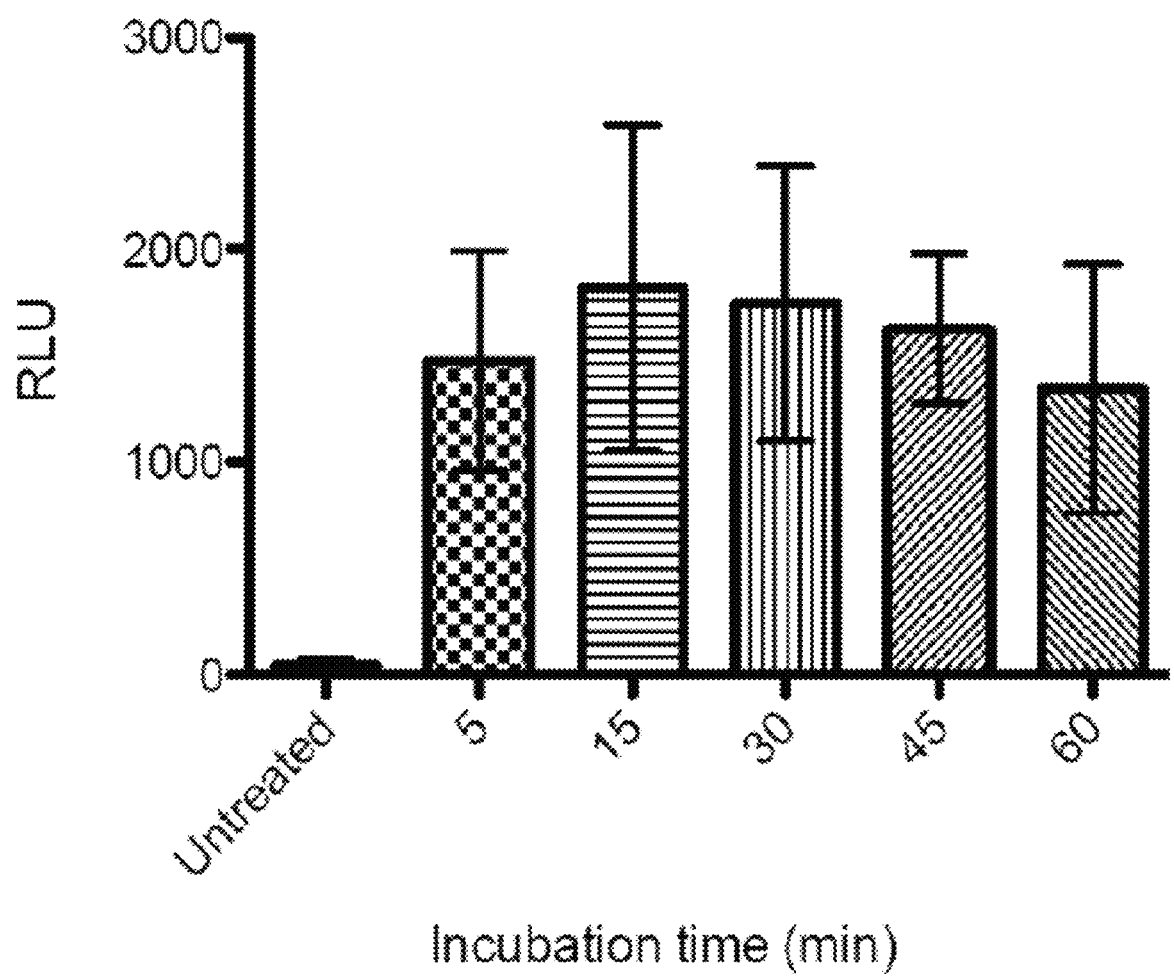

FIG. 15 Extracellular ATP levels following LTX-315 treatment: A375 cells were treated with LTX-315 for 5 minutes at different concentrations or maintained under controlled conditions, and the supernatant was analyzed for the quantification of ATP secretion by luciferase bioluminescence. Quantitative data (mean+−S.D.) for one representative experiment are reported.

Figure 16:
Figure 16:
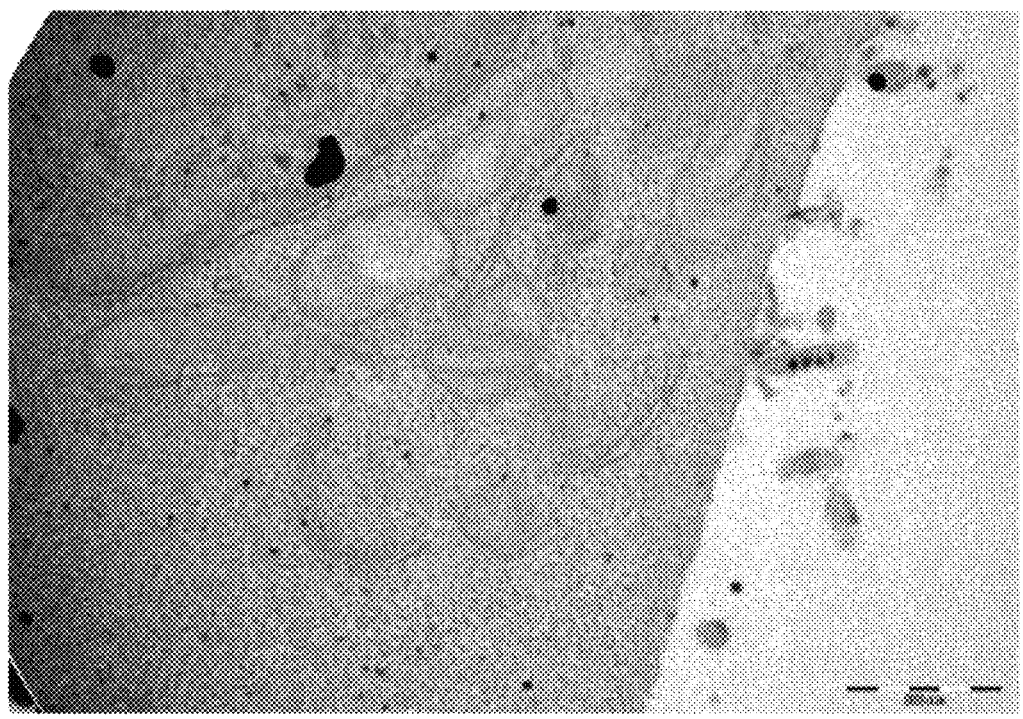
Figure 17A:
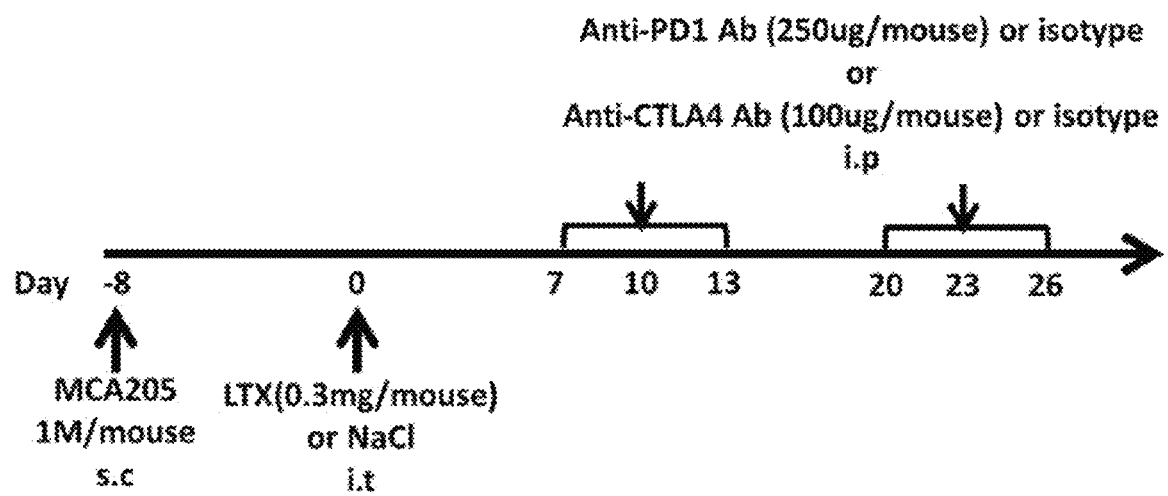
Figure 17B:
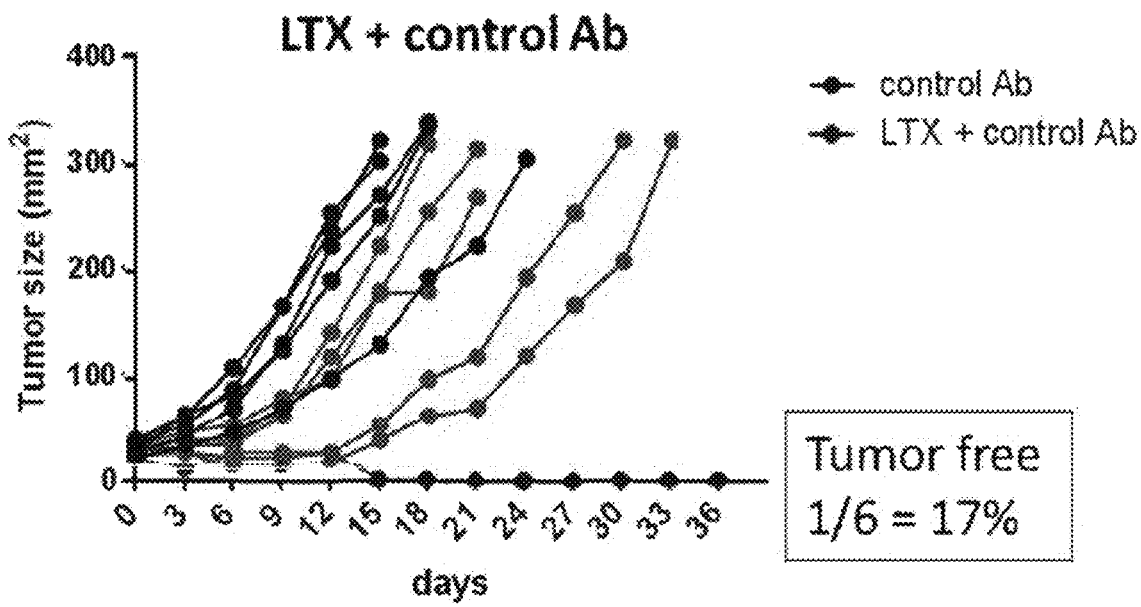
Figure 17C:
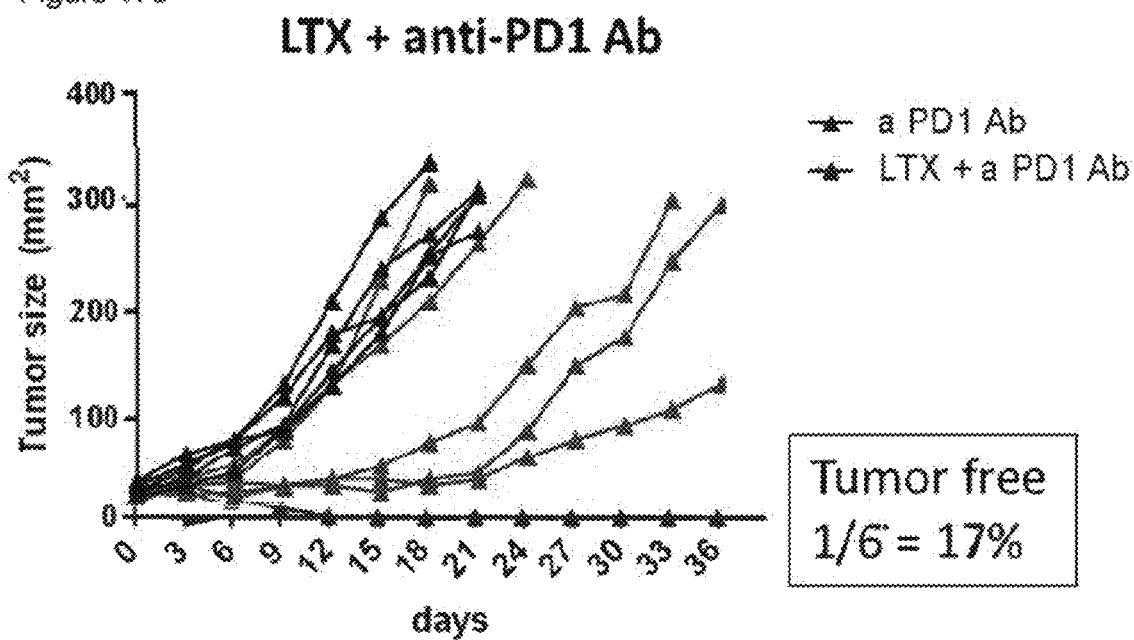
Figure 17D:
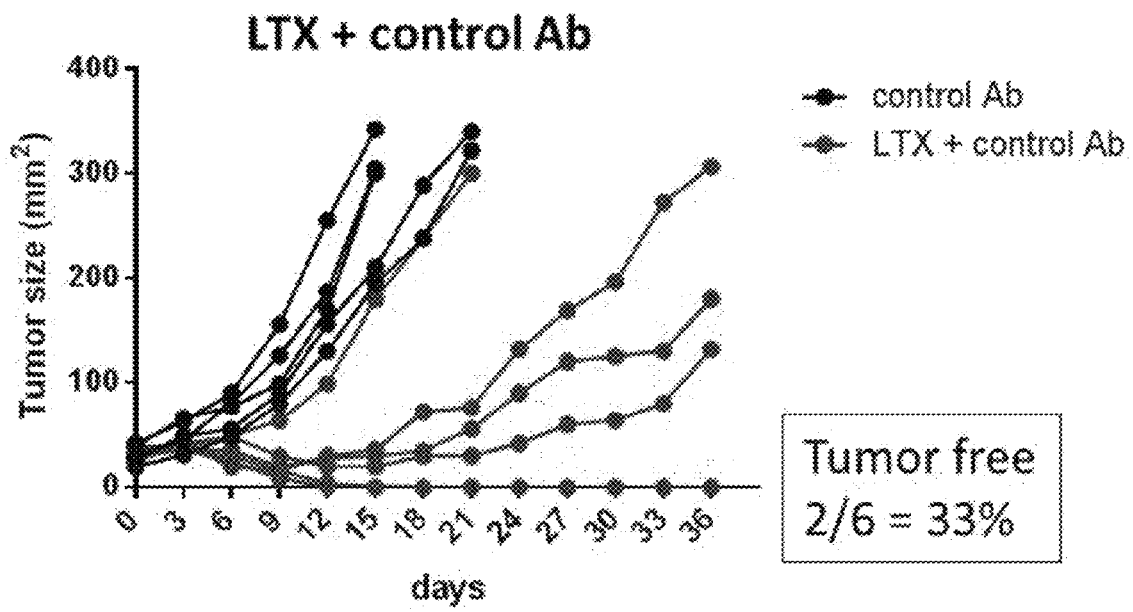
Figure 17E:
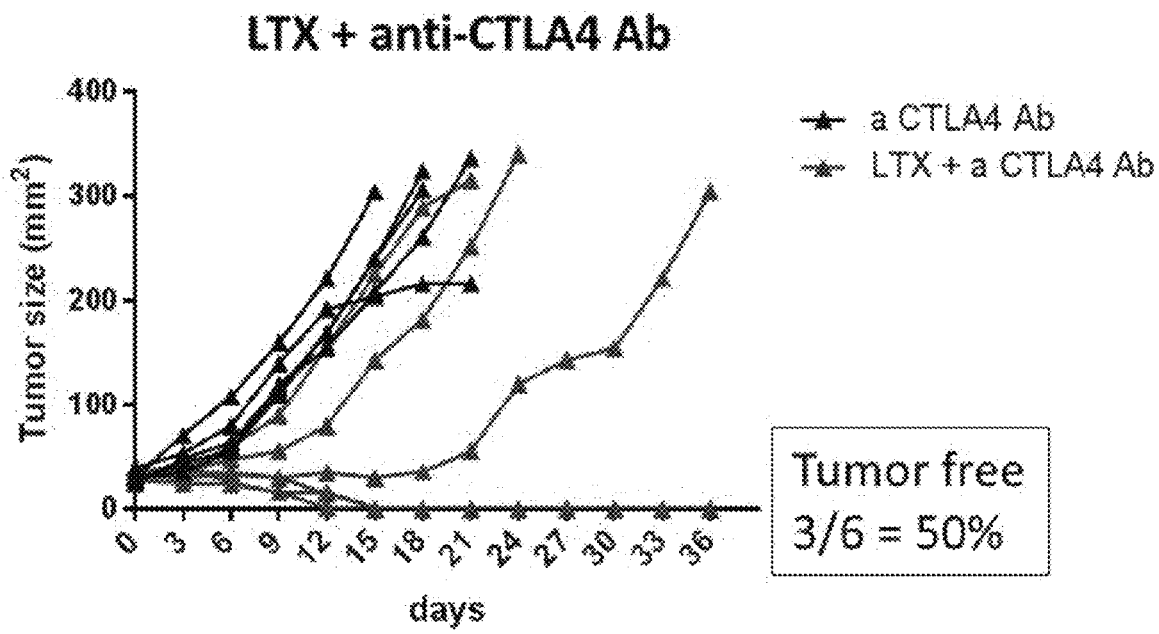
Figure 18A:
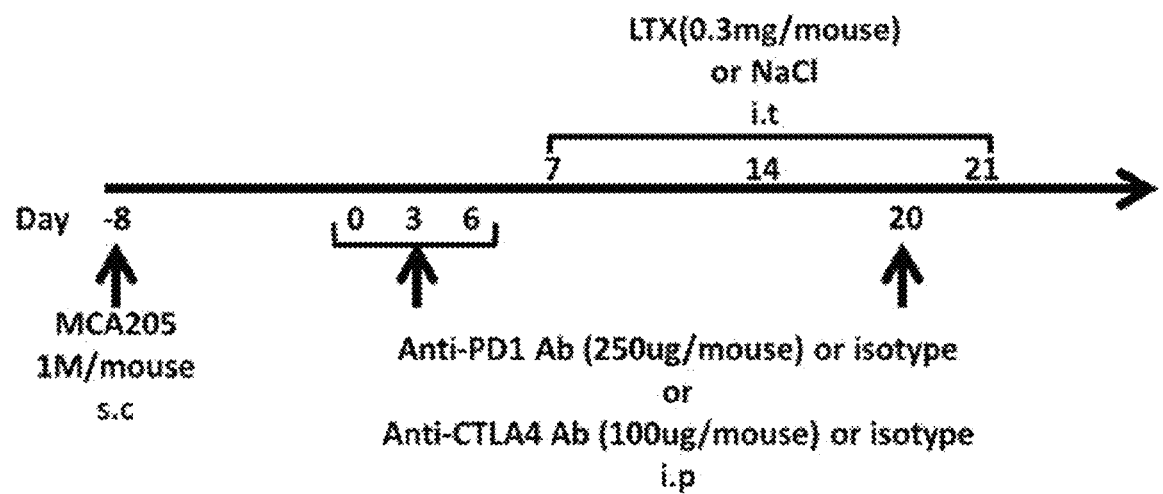
Figure 18B:
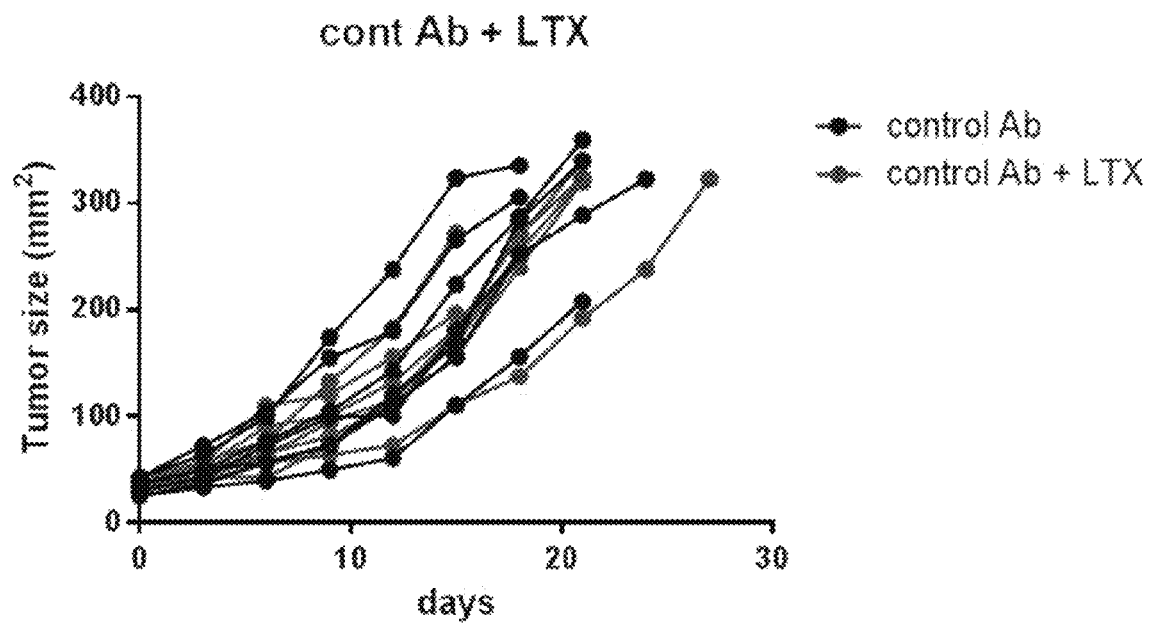
Figure 18C:
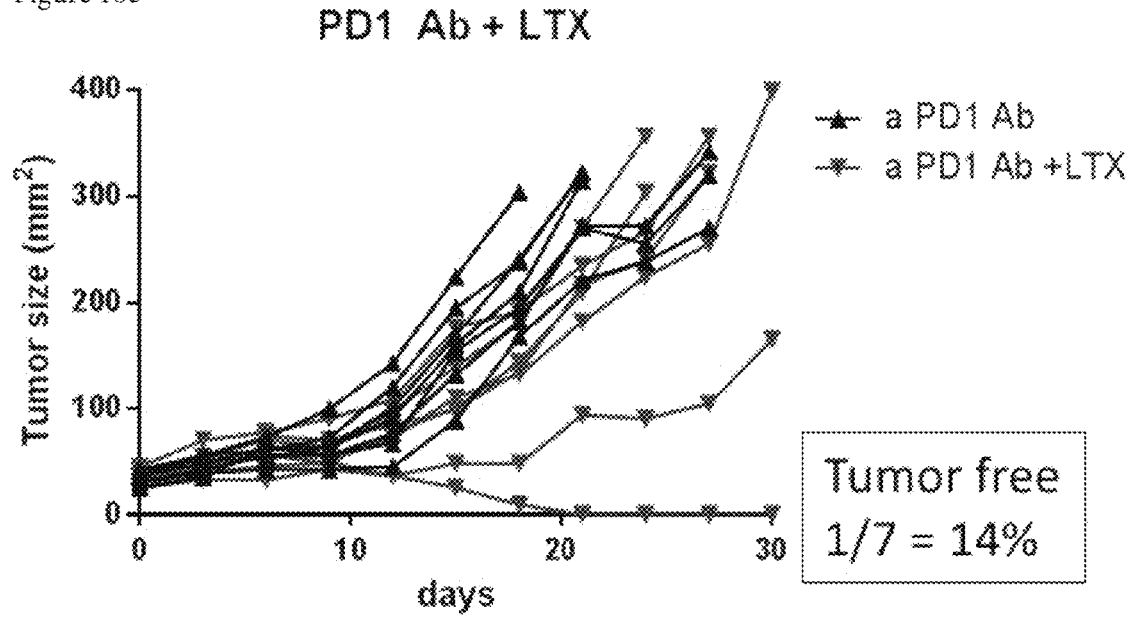
Figure 18D:
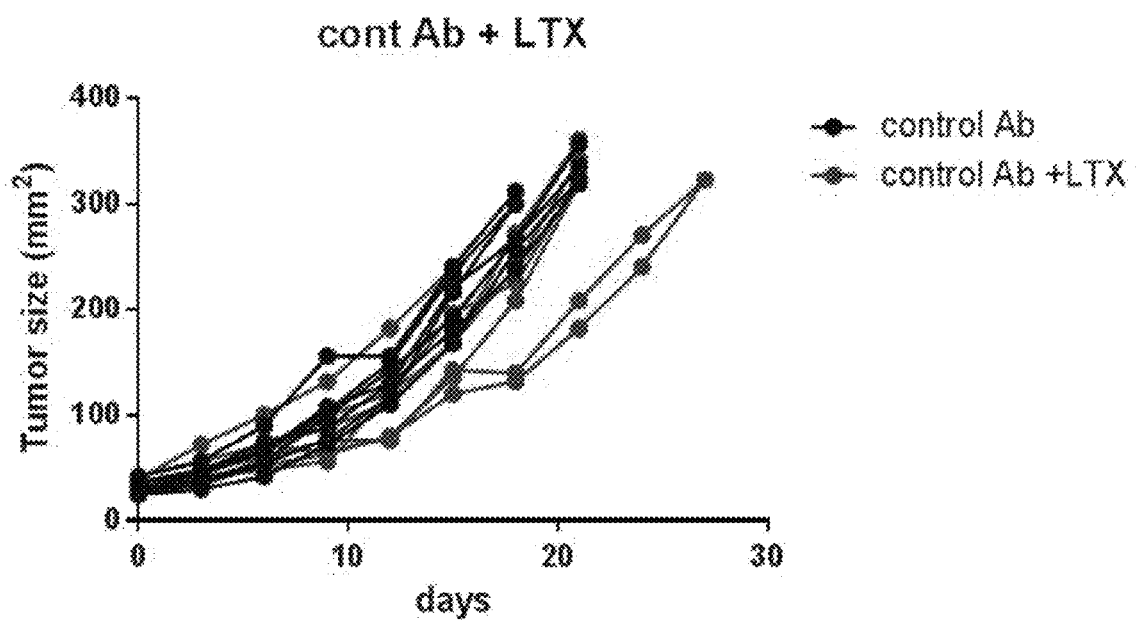
Figure 18E:
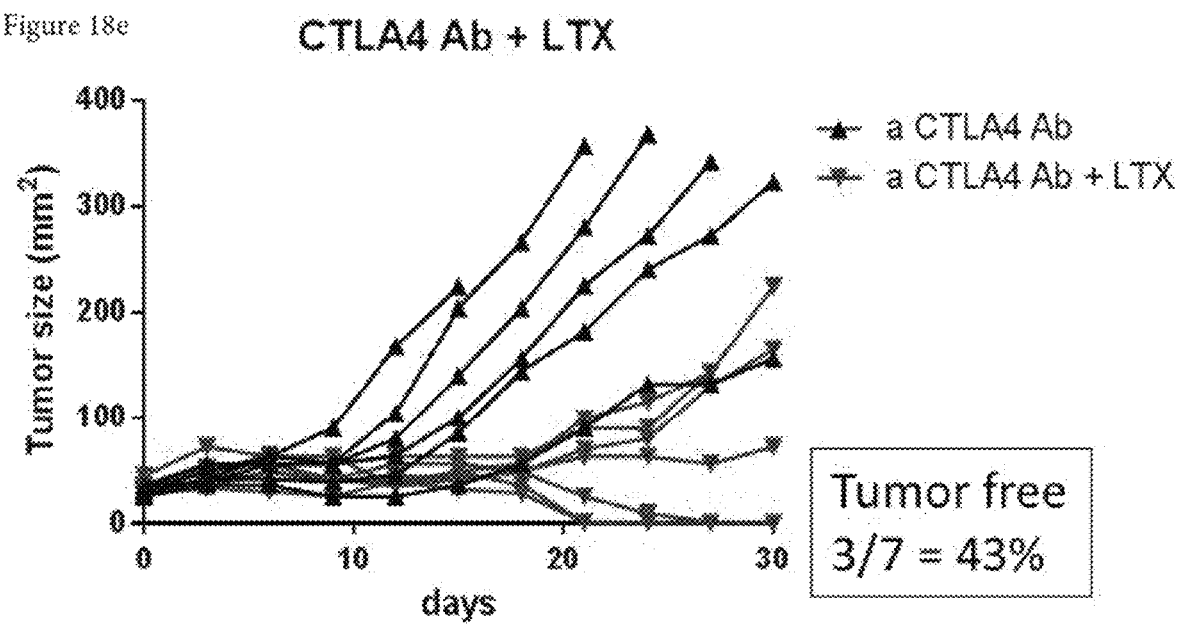
Figure 19A:
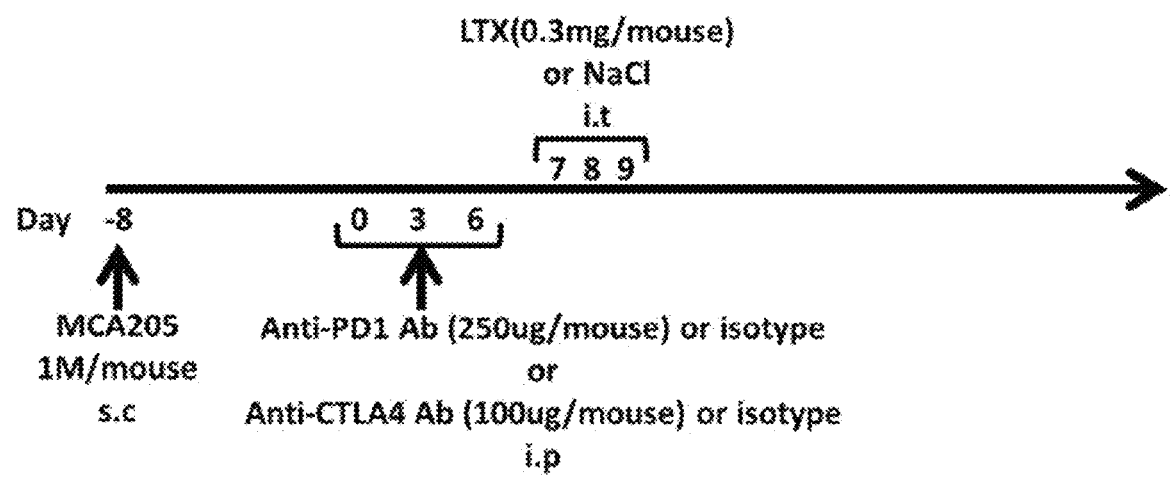
Figure 19B:
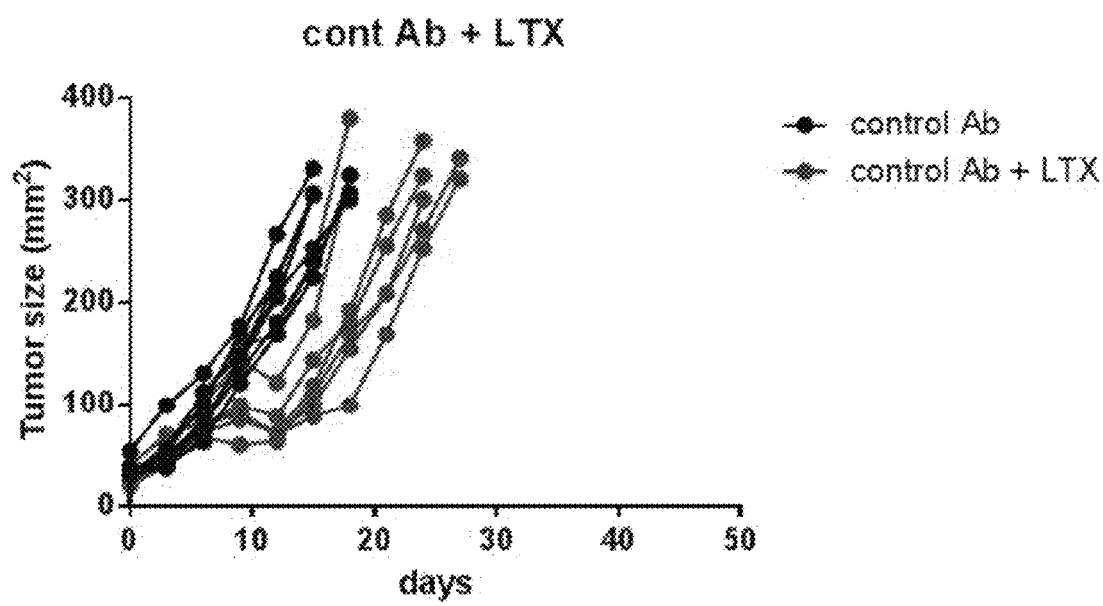
Figure 19C:
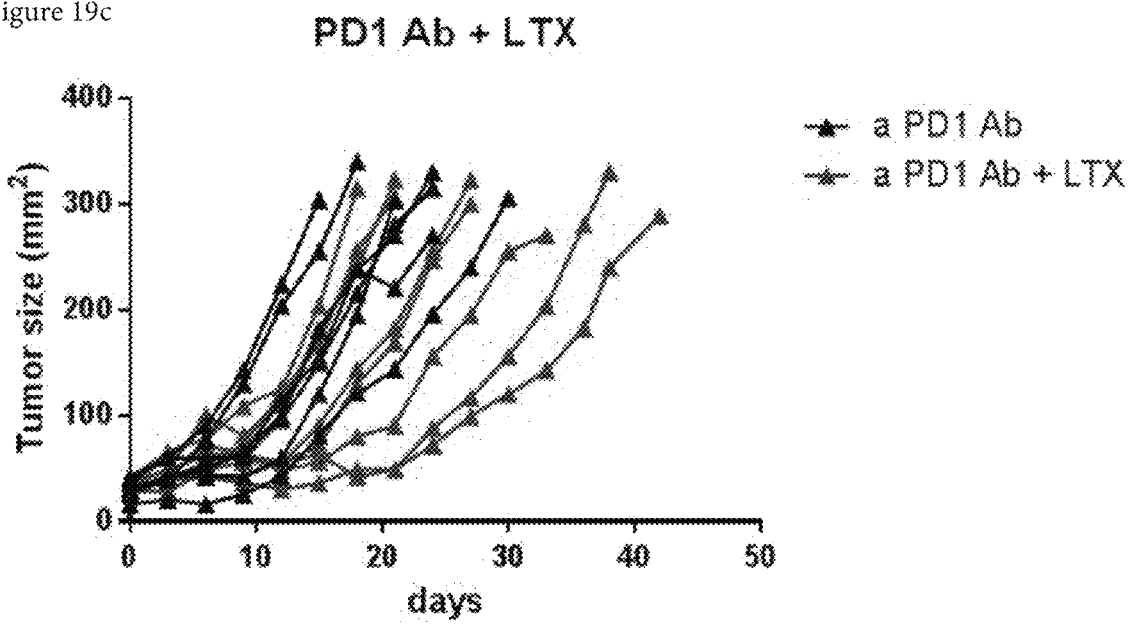
Figure 19D:
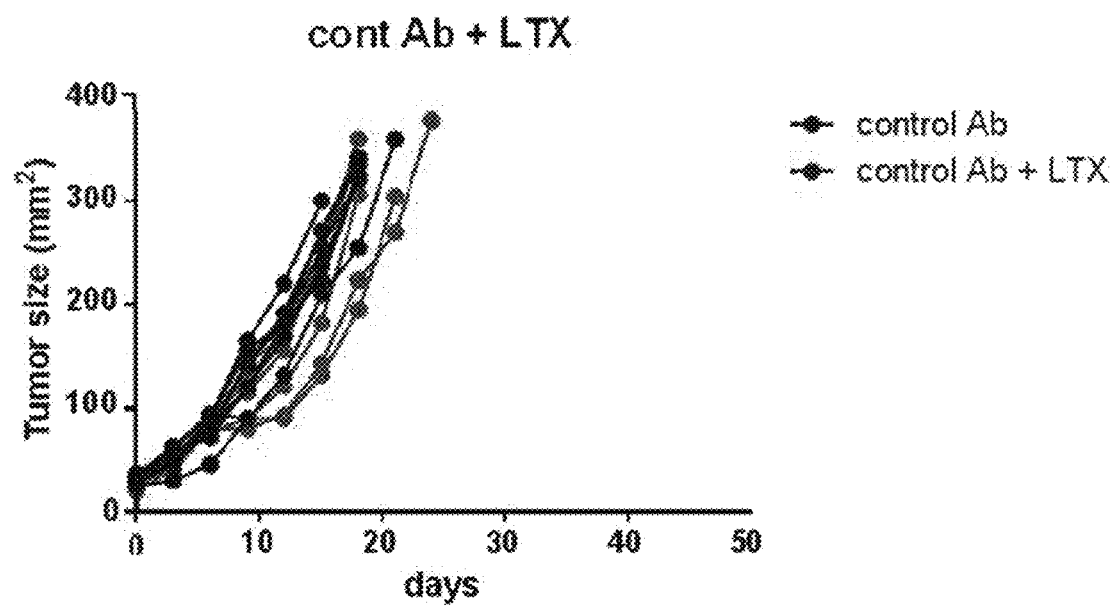
Figure 19E:
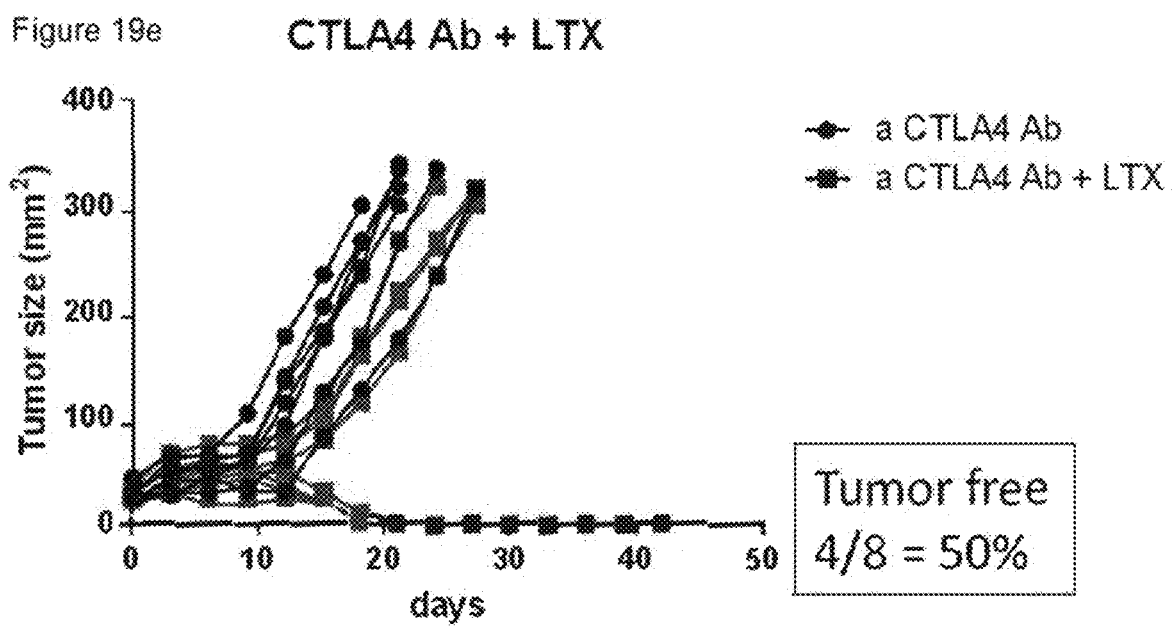
Figure 20A:
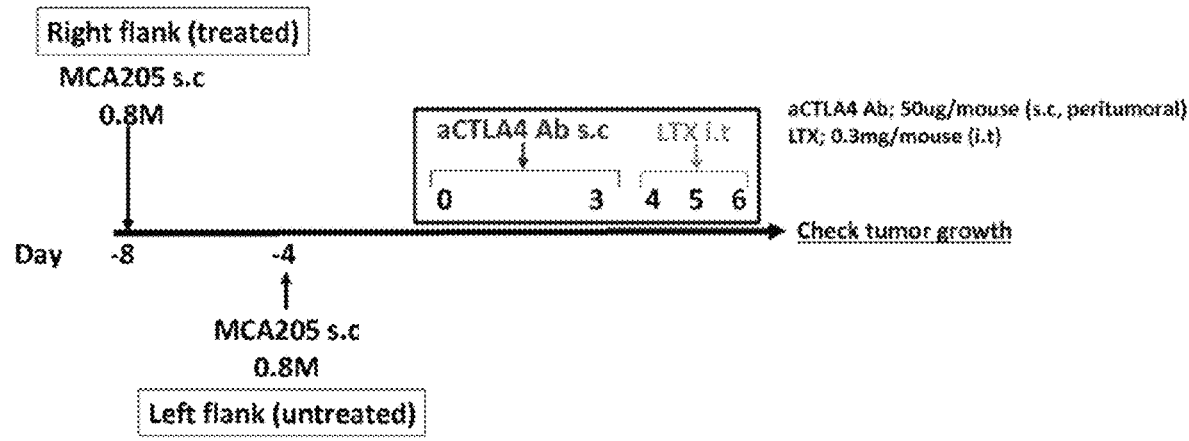
Figure 20B:
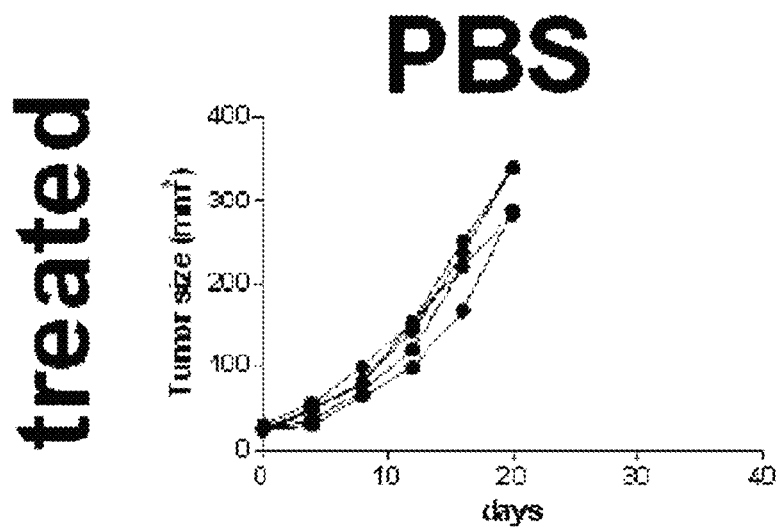
Figure 20C:
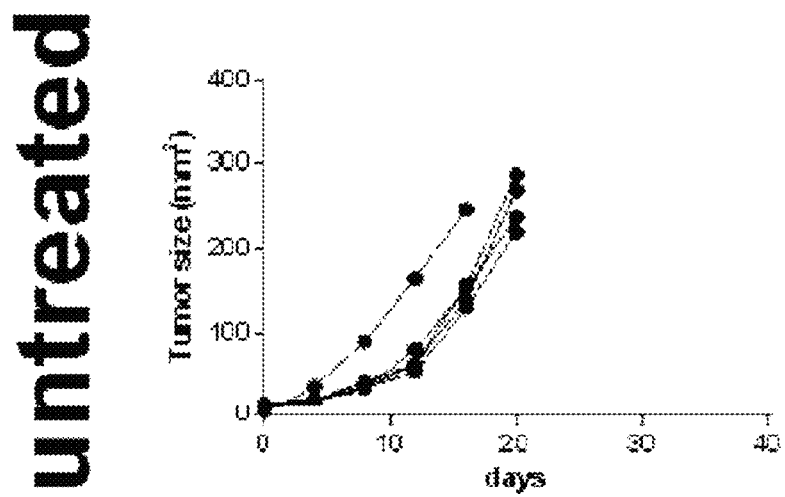
Figure 20D:
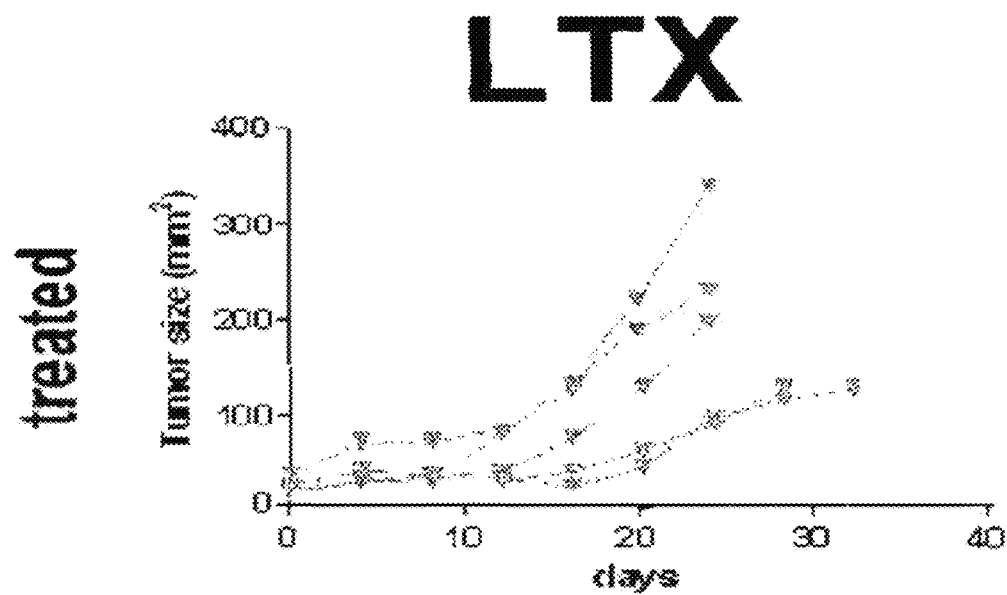
Figure 20E:
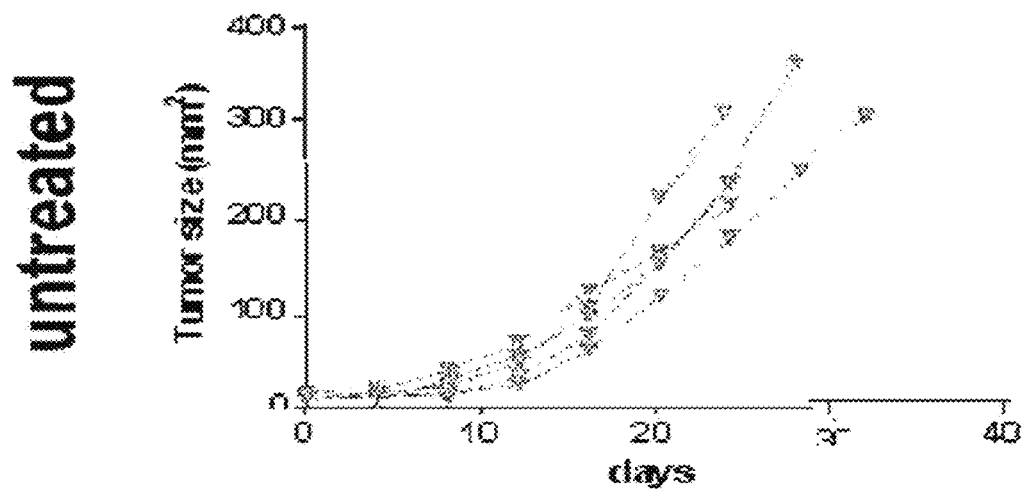
Figure 20F:
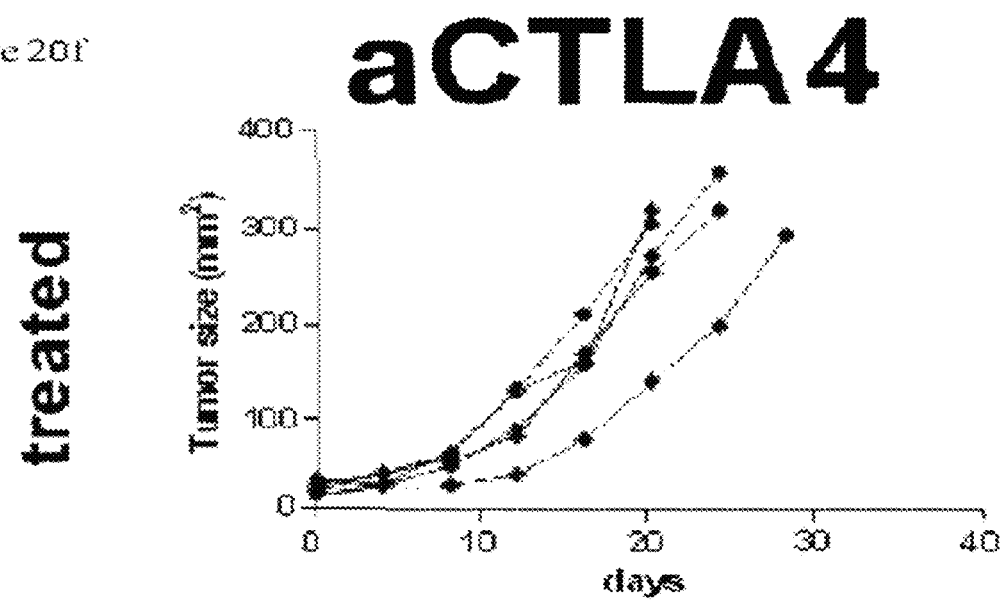
Figure 20G:
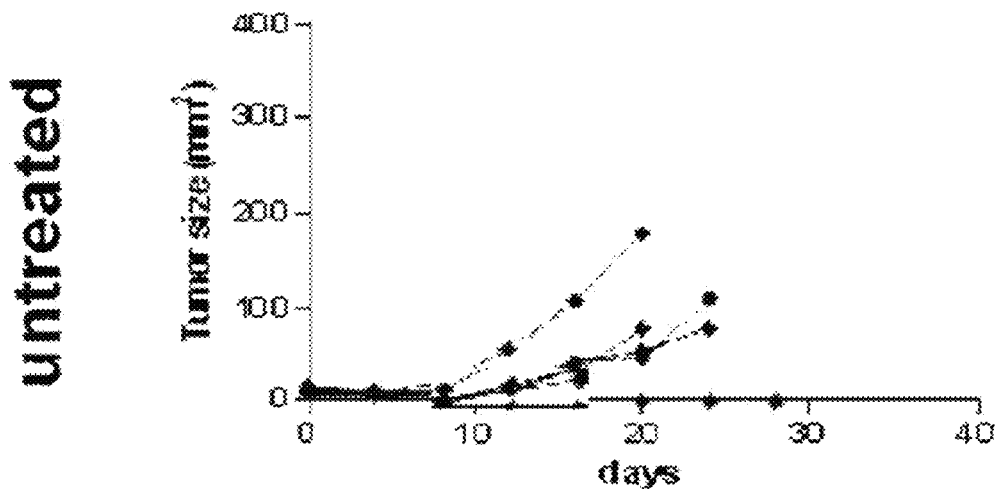
Figure 20H:
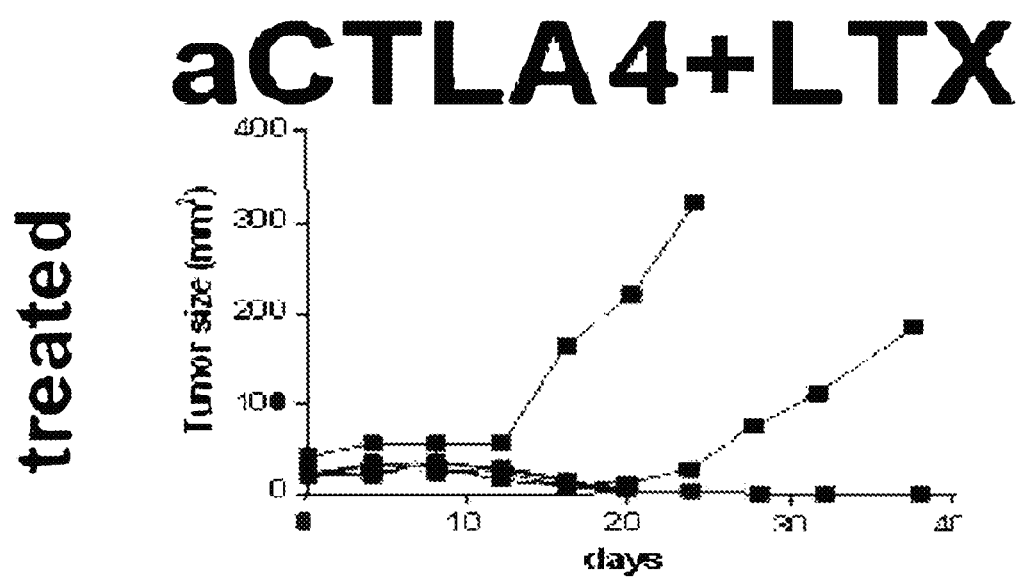
Figure 20I:
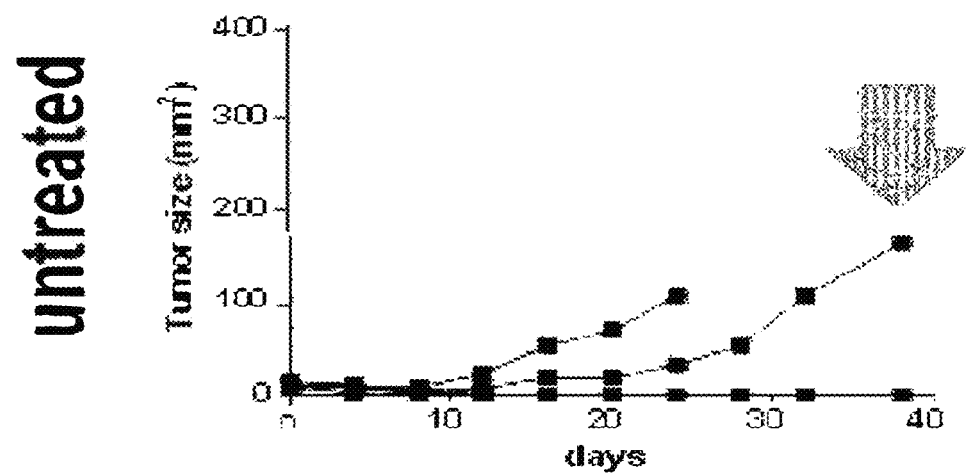
Figure 20J:
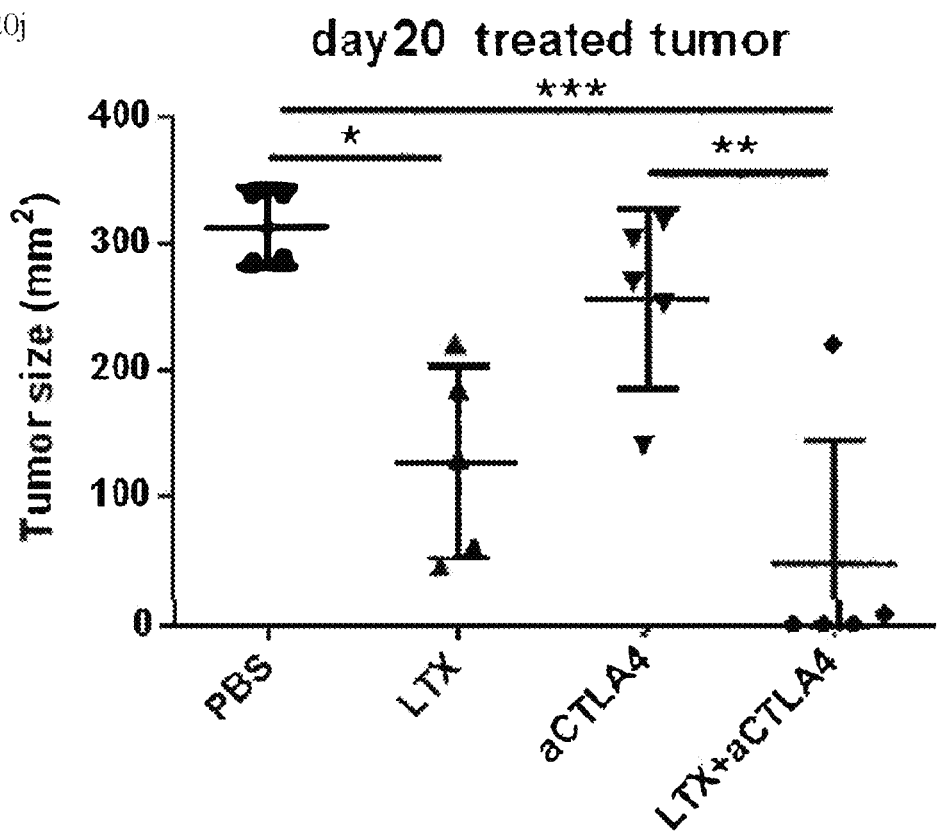
Figure 20K:
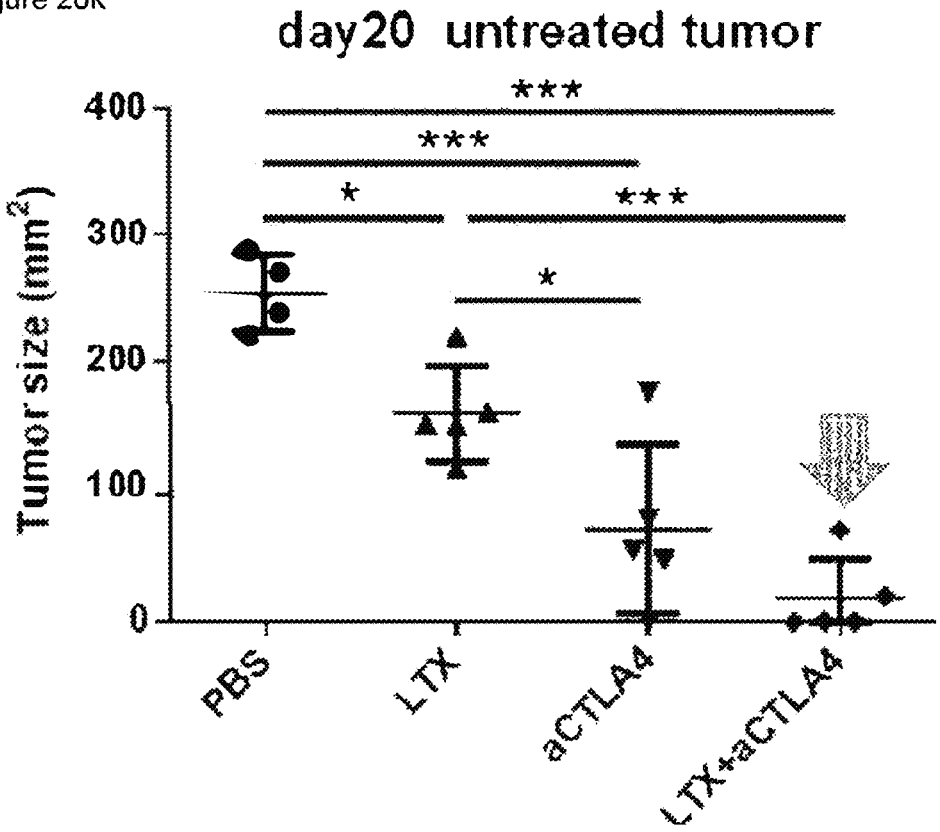

FIG. 16 LTX-315 disintegrates the mitochondria membrane. TEM images of FIG. 16a: human A547 melanoma cells treated with LTX-315 (10 μg/ml) for 60 minutes compared to FIG. 16b: control cells.

FIGS. 17a-17e Experimental setting in a MCA205 sarcoma model starting with LTX-315 first and boosting with either anti-programmed cell death protein 1 (PD-1) antibodies or anti-cytotoxic T-lymphocyte-associated protein 4 (CTLA-4) antibodies (a). Tumour regression is seen with LTX-315 combined with CTLA-4 Ab and with LTX-315 combined with PD-1 Ab ((b) and (d)).

FIGS. 18a-18e Experimental setting in a MCA205 sarcoma model starting with either anti-PD-1 antibodies or anti-CTLA-4 antibodies and boosting with weekly LTX-315 (a). Tumour regression is seen with LTX-315 combined with CTLA-4 Ab and LTX-315 combined with PD-1 Ab ((b) and (d)).

FIGS. 19a-19e Experimental setting in a MCA205 sarcoma model starting with either anti-PD-1 antibodies or anti-CTLA-4 antibodies followed by iterative LTX-315 local inoculations (a). Tumour regression is seen with LTX-315 combined with CTLA-4 Ab and LTX-315 combined with PD-1 Ab ((b) and (d)).

FIGS. 20a-20k Adaptive immunity effects of the combination of anti-CTLA-4 antibodies with LTX-315 in a MCA205 sarcoma model.

(a) Experimental setting showing timing of administrations. MCA205 cells are inoculated into the animal's right flank at day-8 and into the animal's left flank at day-4. Anti-CTLA-4 antibody is administered s.c. in the right flank on days 0 and 3 and LTX315 is administered in the animal's right flank on days 4, 5 and 6 i.t. The left flank is left untreated.

(b) to (k) The combination treatment in which LTX-315 is administered i.t. to a tumour in the animal's right flank induces an adaptive immunity resulting in regression of the tumor in the animal's untreated left flank. Tumour rejection took place in 3 out of 5 (60%) of the treated (right flank) tumours and 3 out of 5 (60%) of the untreated (left flank) tumours following administration of anti-CTLA-4 antibody in combination with LTX-315. Tumour rejection took place in 1 out of 5 (20%) of the untreated (left flank) tumours following administration of anti-CTLA-4 antibody alone.

Figure 21:
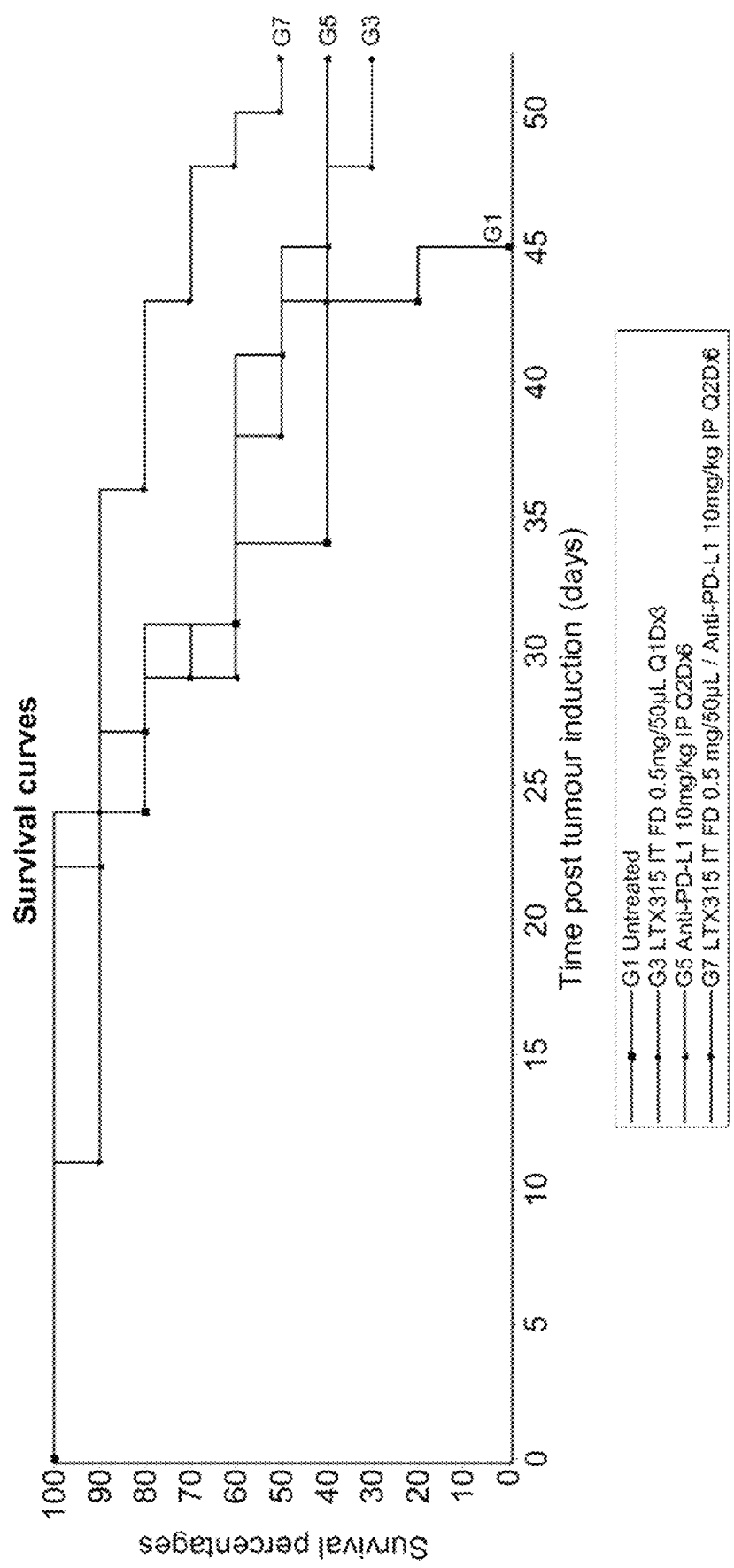

FIG. 21 Combined direct antitumour and adaptive immunity effects of the combination of anti-PD-L1 antibodies with LTX-315 in a EMT-6 murine mammary carcinoma model.

In summary, the Examples below show:

Example 1—that LTX-315 is the most potent of the 5 tested compounds in an in vitro cytotoxic activity study against a panel of 37 human cancer cell lines.

Example 2—that LTX-315 is the most potent of the 5 tested compounds in an in vitro cytotoxic activity study against a panel of 10 lymphoma cell lines.

Example 3—that LTX 315 has a mean EC$_{50}$ value greater than 1200 μg/ml (833 μM) against human red blood cells.

Example 4—that the anti-tumour activity of LTX-315 resulted in a complete tumour response in 3 of 7 treated mice for the Group receiving the optimal dose (Group 1) in an investigation into the effect of LTX-315 at different dose levels on a murine A20 B-cell lymphoma in mice.

Example 5—that four different LTX-315 treatment regimes demonstrated a strong anti tumour effect against murine CT26WT (multidrug resistant) tumours.

Example 6—that LTX-315 has a broad spectrum of activity against various multidrug resistant cancer cell lines and, significantly, a much weaker cytotoxic effect on normal human cells.

Example 7—that complete tumour regression following initial treatment of solid murine tumours with LTX-315 resulted in a form of endogenous long-term protection against growth of the same tumours following re-inoculation.

Example 8—that treatment with LTX-315 may confer long term protection against specific tumours by eliciting an immune response.

Example 9—that an anti A20 cell immune response have been induced by the injection of the cocktail of LTX-315 and lysed A20 cells.

Example 10—that treatment with LTX-315 induces hallmarks of immunogenic cell death by mitochondria distortion in human melanoma cells.

Example 11—that treatment with LTX-315 in combination with an anti-CTLA-4 antibody caused a complete and long-lasting tumor regression in a high proportion of test subjects and induced an adaptive immune response. Anti-PD-1 antibody also showed an ability to act in combination with LTX-315 to inhibit tumour growth.

Example 12—that treatment with LTX-315 in combination with an anti-PD-L1 antibody caused tumour regression in a high proportion of test subjects and induced an adaptive immune response.

Example 1

In Vitro Cytotoxic Activity Study of 5 Test Compounds Against a Panel of 37 Human Cancer Cell Lines 1. Study Aim To determine the concentrations of five novel compounds to obtain a 50% inhibition of proliferation ($IC_{50}$) against a panel of 37 human cancer cell lines.

2. Materials and Methods 2.1. Test Substances
2.1.1. Test Substances
  Test substances, LTX-302, LTX-313, LTX-315, LTX-320 and LTX-329 (see Table 1) provided in powder form.
2.1.2. Positive Control
  Triton X-100 was used as positive control, supplied by Oncodesign (Dijon, France) from Sigma (Saint Quentin Fallavier, France).
2.1.3. Drug Vehicle and Storage Conditions
  Compounds were stored at 4° C. Powder was first dissolved in serum free culture medium (RPMI 1640, Lonza, Verviers, Belgium) and further diluted using serum-free culture medium to reach appropriate dilutions. Stock solution was not stored and was prepared fresh the day of experiment.
  1% (final concentration) Triton X-100 was obtained by dilution using culture medium.
2.2. Tumor Cell Lines and Culture Conditions
2.2.1. Tumor Cell Lines
  Cancer cell lines and culture media were purchased and provided by Oncodesign. The details of the cell lines is presented in Table 1 below.

TABLE 1

| Cell lines | Origin | Source |
|---|---|---|
| BLOOD | | |
| CCRF-CEM | acute lymphoblastic leukemia, T cells | Pharmacell [a] |
| CCRF-CEM/VLB | acute lymphoblastic leukemia, T cells | Pharmacell |
| HL-60 | acute promyelocytic leukemia, AML, pluripotent differentiation | ATCC [b] |
| HL-60/ADR | acute promyelocytic leukemia, AML | Pharmacell |
| K-562 | chronic myeloid leukemia, pleural effusion metastasis | ATCC |
| K-562/Gleevec | chronic myeloid leukemia, pleural effusion metastasis | Oncodesign |
| RPMI 8226 | myeloma, B cells, Igl-type | Pharmacell |
| BRAIN | | |
| SH-SY5Y | neuroblastoma, bone marrow metastasis | ATCC |
| SK-N-AS | neuroblastoma, bone marrow metastasis | ATCC |
| U-87 MG | glioblastoma, astrocytoma | ATCC |
| BREAST | | |
| MCF-7 | invasive ductal carcinoma, pleural effusion metastasis | Pharmacell |
| MCF7/mdr | adenocarcinoma, pleural effusion metastasis | Pharmacell |
| MDA-MB-231 | invasive ductal carcinoma, pleural effusion metastasis | Pharmacell |
| MDA-MB-435S | invasive ductal carcinoma, pleural effusion metastasis | ATCC |
| T-47D | invasive ductal carcinoma, pleural effusion metastasis | ATCC |
| COLON | | |
| COLO 205 | colorectal adenocarcinoma, ascites metastasis | ATCC |
| HCT 116 | colorectal carcinoma | ATCC |
| HCT-15 | colorectal adenocarcinoma | ATCC |
| HT-29 | colorectal adenocarcinoma | ATCC |
| ENDOTHELIUM | | |
| HUV-EC-C | normal | ATCC |
| KIDNEY | | |
| 786-O | renal cell adenocarcinoma | ATCC |
| A-498 | carcinoma | ATCC |
| LIVER | | |
| Hep G2 | hepatocellular carcinoma | ATCC |
| SK-HEP-1 | adenocarcinoma, ascites metastasis | ATCC |
| LUNG | | |
| A549 | carcinoma | Pharmacell |
| Calu-6 | anaplastic carcinoma | ATCC |
| NCI-H460 | carcinoma, pleural effusion metastasis | ATCC |
| OVARY | | |
| IGROV-1 | carcinoma | Pharmacell |
| IGROV-1/CDDP | carcinoma | Pharmacell |
| NIH:OVCAR-3 | adenocarcinoma, ascites metastasis | Pharmacell |
| SK-OV-3 | adenocarcinoma, ascites metastasis | Pharmacell |
| PANCREAS | | |
| BxPC-3 | adenocarcinoma | ATCC |
| PANC-1 | carcinoma | ATCC |
| PROSTATE | | |
| DU 145 | carcinoma, brain metastasis | Pharmacell |
| PC-3 | adenocarcinoma, bone metastasis | ATCC |

TABLE 1-continued

| Cell lines | Origin | Source |
|---|---|---|
| SKIN | | |
| A-431 | epidermoid carcinoma | ATCC |
| Malme-3M | Malignant melanoma | ATCC |
| SK-MEL-2 | malignant melanoma, skin metastasis | ATCC |

[a] - Pharmacell, Paris
[b] - ATCC, Manassas, Virginia, USA 2.2.2. Culture Conditions Tumor cells were grown as adherent monolayers or as suspensions at 37° C. in a humidified atmosphere (5% $CO_2$, 95% air). The culture medium was RPMI 1640 containing 2 mM L-glutamine (Lonza, Belgium) and supplemented with 10% fetal bovine serum (FBS, Lonza). For experimental use, the adherent cells were detached from the culture flask by a 5-minute treatment with trypsin-versene (Lonza), diluted in Hanks' medium without calcium or magnesium (Lonza) and neutralized by addition of complete culture medium. Cells were counted in a hemocytometer and their viability was assessed by 0.25% trypan blue exclusion.

*Mycoplasma* detection was performed using the MycoAlert® *Mycoplasma* Detection Kit (Lonza) in accordance with the manufacturer's instructions. All tested cells were found to be negative for *mycoplasma* contamination.

3. Experimental Design and Treatments 3.1. Cell Lines Amplification and Plating

Tumor cells were plated in 96-well flat-bottom microtitration plates (Nunc, Dutscher, Brumath, France) and incubated at 37° C. for 24 hours before treatment in 190 µl of drug-free culture medium supplemented or not with 10% FBS for adherent or suspension growing cell lines, respectively.

Implantation densities for each cell lines are summarized in Table 2 below:

TABLE 2

| Cell lines | Implantation densities (cells/well) | Cell lines | Implantation densities (cells/well) |
|---|---|---|---|
| CCRF-CEM | 25,000 | HUV-EC-C | 20,000 |
| CCRF-CEM/VLB | 25,000 | 786-O | 15,000 |
| HL-60 | 20,000 | A-498 | 15,000 |
| HL-60/ADR | 20,000 | Hep G2 | 15,000 |
| K-562 | 20,000 | SK-HEP-1 | 15,000 |
| K-562/IMR | 20,000 | A549 | 15,000 |
| RPMI 8226 | 20,000 | Calu-6 | 15,000 |
| SH-SY5Y | 20,000 | NCI-H460 | 15,000 |
| SK-N-AS | 15,000 | IGROV-1 | 15,000 |
| U-87 MG | 15,000 | IGROV-1/CDDP | 15,000 |
| MCF-7 | 20,000 | NIH:OVCAR-3 | 15,000 |
| MCF7/mdr | 20,000 | SK-OV-3 | 15,000 |
| MDA-MB-231 | 15,000 | BxPC-3 | 15,000 |
| MDA-MB-435S | 20,000 | PANC-1 | 15,000 |
| T-47D | 15,000 | DU 145 | 15,000 |
| COLO 205 | 15,000 | PC-3 | 15,000 |
| HCT 116 | 15,000 | A-431 | 15,000 |
| HCT-15 | 15,000 | Malme-3M | 15,000 |
| HT-29 | 20,000 | SK-MEL-2 | 15,000 |

3.2. $IC_{50}$ Determination

The adherent cell lines were washed once with 200 µl FBS-free culture medium before treatment. Tumor cells were incubated for 4 hours with 10 concentrations of compounds in ¼ dilution step with a top dose of 400 µM (range $4 \times 10^{-4}$ to $4 \times 10^{-10}$ M), with 1% (final concentration) Triton X-100 as positive control and FBS-free culture medium as negative control. The cells (190 µl) were incubated in a 200 µl final volume of FBS-free culture medium containing test substances at 37° C. under 5% $CO_2$.

Three independent experiments were performed, each concentration being tested in quadruplicate. Control cells were treated with vehicle alone. At the end of treatments, the cytotoxic activity was evaluated by a MTS assay (see § 3.3).

Dilutions of tested compound as well as distribution to plates containing cells were performed using a Sciclone ALH 3000 liquid handling system (Caliper Life Sciences S.A.). According to automate use, a single range of concentrations was tested whatever the cell lines to be tested. The range was not adapted for each cell line.

3.3. MTS Assay

The in vitro cytotoxic activity of the test substance was revealed by a MTS assay (BALTROP J. A. et al., Bioorg. Med. Chem. Lett. 1991, 1:611-614) using a novel tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT.

At the end of the cells treatment, 40 µl of a 0.22 µm filtered freshly combined solution of MTS (20 ml at 2 mg/ml, Ref G1111, Batch 235897, Exp 03/2009, Promega, Charbonnières, France) and PMS (1 ml at 0.92 mg/ml, Ref P9625, Batch 065K0961, Sigma) in Dulbecco's Phosphate Buffered Saline (DPBS, Ref 17-513Q, Batch 6MB0152, Cambrex), were added in each well. Culture plates were incubated for 2 h at 37° C. Absorbency (OD) were measured at 490 nm in each well using VICTOR[3TM] 1420 multilabeled counter (Wallac, PerkinElmer, Courtaboeuf, France).

4. Data Presentation 4.1. $IC_{50}$ Determination

The dose response inhibition of proliferation (IC) was expressed as follows:

$$IC = \frac{OD_{drug-exposed\ wells}}{OD_{drug-free\ wells}} \times 100$$

The OD values are the mean of 4 experimental measurements.

$IC_{50}$: drug concentration to obtain a 50% inhibition of cell proliferation.

The dose-response curves were plotted using XLFit 3 (IDBS, United Kingdom). The $IC_{50}$ determination values were calculated using the XLFit 3 software from semi-log curves. Individual $IC_{50}$ determination values as well as mean and SD values were generated.

4.2. Resistance Index (RI)

Resistance index was calculated using the following formula:

$$RI_{compound\ A} = \frac{IC_{50\ compound A}(\text{Resistant cell line})}{IC_{50 compound A}(\text{Sensitive cell line})}$$

Resistance index was calculated for each compound for each couple of sensitive and resistant cell lines. Individual resistance index was calculated when $IC_{50}$ values of both sensitive and corresponding resistant cell lines were determined within same experiment. In addition, resistance index was also calculated ratio of mean $IC_{50}$ values obtained during three independent experiments.

5. Results 5.1. LTX-302

All thirty seven human tumor cell lines tested were sensitive to LTX-302 compound with $IC_{50}$ values ranging from 4.83±0.96 µM to 20.09±4.07 µM for T-47D and Hep G2 cell lines, respectively.

Mean $IC_{50}$ value for LTX-302 compound obtained on the 37 tumor cell lines was 12.05+4.27 µM with a median value of 11.70 µM. Mean $IC_{50}$ value obtained for the normal cell line (HUV-EC-C) was higher than for any of the tumor cell lines.

Hematological and lung cancer cell lines were the most sensitive to LTX-302 compound (median $IC_{50}$ values 7.96 µM (n=7) and 9.02 µM (n=3) for hematological and lung cancer cell lines, respectively) whereas liver cancer cell lines were the most resistant (median $IC_{50}$ value 17.84 µM, n=2).

Activity of LTX-302 compound seemed to be slightly decreased by acquired resistance towards doxorubicin as exhibited by the RI values of both HL-60/ADR and MCF-7/mdr cell lines (1.31 and 1.23 for HL-60/ADR and MCF-7/mdr cell lines, respectively). On the contrary, activity of LTX-302 compound seemed to be increased by acquired resistance towards cisplatin as exhibited by a RI value of 0.33 for IGROV-1/CDDP cell line.

5.2. LTX-313

All thirty seven (37) human tumor cell lines tested were sensitive to LTX-313 compound with $IC_{50}$ values ranging from 4.01±0.39 µM to 18.49±4.86 µM for RPMI 8226 and U-87 MG cell lines, respectively.

Mean $IC_{50}$ value for LTX-313 compound obtained on the 37 tumor cell lines was 9.60±3.73 µM with a median value of 8.83 µM. Mean $IC_{50}$ value obtained for the normal cell line (HUV-EC-C) was higher than for any of the tumor cell lines.

Hematological cancer cell lines were the most sensitive to LTX-313 compound (median $IC_{50}$ value 7.04 µM, n=7) whereas liver cancer cell lines were the most resistant (median $IC_{50}$ value 13.71 µM, n=2).

Activity of LTX-313 compound seemed not to be modified by acquired resistance towards doxorubicin as exhibited by the RI values of CCRF-CEM/VLB, HL-60/ADR and MCF-7/mdr cell lines (0.76, 1.16 and 1.24 for CCRF-CEM/VLB, HL-60/ADR and MCF-7/mdr cell lines, respectively). On the contrary, activity of LTX-313 compound seemed to be increased by acquired resistance towards cisplatin as exhibited by a RI value of 0.49 for IGROV-1/CDDP cell line.

5.3. LTX-315

All thirty seven human tumor cell lines tested were sensitive to LTX-315 compound with $IC_{50}$ values ranging from 1.18±0.25 µM to 7.16±0.99 µM for T-47D and SK-OV-3 cell lines, respectively.

Mean $IC_{50}$ value for LTX-315 compound obtained on the 37 tumor cell lines was 3.63±1.45 µM with a median value of 3.27 µM. Mean $IC_{50}$ value obtained for the normal cell line (HUV-EC-C) was higher than for any of the tumor cell lines.

Breast, hematological and lung cancer cell lines were the most sensitive to LTX-315 compound (median $IC_{50}$ values 2.45 µM (n=5), 2.60 µM (n=7) and 2.83 µM (n=3) for breast, hematological and lung cancer cell lines respectively) whereas liver cancer cell lines were the most resistant (median $IC_{50}$ value 5.86 µM, n=2).

Activity of LTX-315 compound seemed to be slightly decreased by acquired resistance towards doxorubicin as exhibited by the RI values of HL-60/ADR and MCF-7/mdr cell lines (1.45 and 1.12 for HL-60/ADR and MCF-7/mdr cell lines, respectively). On the contrary, activity of LTX-315 compound seemed to be increased by acquired resistance towards cisplatin as exhibited by a RI value of 0.50 for IGROV-1/CDDP cell line.

5.4. LTX-320

All thirty seven human tumor cell lines tested were sensitive to LTX-320 compound with $IC_{50}$ values ranging from 3.46±0.22 µM to 16.64±3.15 µM for T-47D and Hep G2 cell lines, respectively.

Mean $IC_{50}$ value for LTX-320 compound obtained on the 37 tumor cell lines was 7.58±2.79 µM with a median value of 6.92 µM. Mean $IC_{50}$ value obtained for the normal cell line (HUV-EC-C) was higher than for any of the tumor cell lines.

Hematological, breast, kidney and brain cancer cell lines were the most sensitive to LTX-320 compound (median $IC_{50}$ values 6.04 µM (n=7), 6.60 µM (n=5), 6.60 µM (n=2) and 6.92 µM (n=3) for hematological, breast, kidney and brain cancer cell lines respectively) whereas liver cancer cell lines were the most resistant (median $IC_{50}$ value 11.46 µM, n=2).

Activity of LTX-320 compound seemed not to be modified by acquired resistance towards doxorubicin as exhibited by the RI values of HL-60/ADR and MCF-7/mdr cell lines (0.90 and 1.19 for HL-60/ADR and MCF-7/mdr cell lines, respectively). On the contrary, activity of LTX-320 compound seemed to be increased by acquired resistance towards cisplatin as exhibited by a RI value of 0.49 for IGROV-1/CDDP cell line.

5.5. LTX-329

All thirty seven human tumor cell lines tested were sensitive to LTX-329 compound with $IC_{50}$ values ranging from 2.43±0.34 µM to 16.90±1.18 µM for T-47D and U-87 MG cell lines, respectively.

Mean $IC_{50}$ value for LTX-329 compound obtained on the 37 tumor cell lines was 8.17±3.20 µM with a median value of 7.89 µM. Mean $IC_{50}$ value obtained for the normal cell line (HUV-EC-C) was higher than for any of the tumor cell lines.

Breast and hematological cancer cell lines were the most sensitive to LTX-329 compound (median $IC_{50}$ values 4.92 µM (n=5) and 5.26 µM (n=7) for breast and hematological cancer cell lines respectively) whereas ovarian cancer cell lines were the most resistant (median $IC_{50}$ value 13.37 µM, n=4).

Activity of LTX-329 compound seemed not to be modified by acquired resistance towards doxorubicin as exhibited by the RI values of CCRF-CEM/VLB, HL-60/ADR and MCF-7/mdr cell lines (0.76, 0.80 and 1.07 for CCRF-CEM/VLB, HL-60/ADR and MCF-7/mdr cell lines, respectively). On the contrary, activity of LTX-329 compound seemed to be increased by acquired resistance towards cisplatin as exhibited by a RI value of 0.46 for IGROV-1/CDDP cell line.

5.6. General Comments

T-47D breast cancer cell line is the most sensitive cell line whatever the LTX compound tested.

Hematological cancer cell lines are the most sensitive histological type for all five compounds tested, liver and ovarian cancer cell lines being within the most resistant cell lines. All five compounds tested exhibited highest activity on IGROV-1/CDDP cell line (resistant to cisplatin) than on parental IGROV-1 ovarian cancer cell line. Doxorubicin resistance seemed to slightly decrease activity of LTX compounds.

LTX-315 compound is the most potent compound from the five compounds tested.

6. Conclusions

All five compounds tested (i.e. LTX-302, LTX-313, LTX-315, LTX-320 and LTX-329) exhibited cytolytic activity against 37 human cancer cell lines tested with $IC_{50}$ values in micromolar to ten micromolar range.

LTX-315 compound is the most potent compound tested with $IC_{50}$ values between 1 and 5 micromolar on all 37 human cancer cell lines tested.

Example 2

In Vitro Cytotoxic Activity Study of 5 Test Compounds Against a Panel of 10 Lymphoma Cell Lines

1. Study Aim

To determine the concentrations of five novel compounds to obtain a 50% inhibition of proliferation ($IC_{50}$) against a panel of 10 lymphoma cell lines.

2. Materials and Methods 2.1. Test Substances
2.1.1. Test Substances
Test substances, LTX-302, LTX-313, LTX-315, LTX-320 and LTX-329 (see Table 1) provided in powder form.
2.1.2. Positive Control
Triton X-100 was used as positive control and supplied by Oncodesign (Dijon, France) from Sigma (Saint Quentin Fallavier, France).
2.1.3. Drug Vehicle and Storage Condition
  Compounds were stored at 4° C. Powder was first dissolved in serum free culture medium (RPMI 1640, Lonza, Verviers, Belgium) and further diluted using serum-free culture medium to reach appropriate dilutions. Stock solution was not stored and was prepared fresh the day of experiment.
  1% (final concentration) Triton X-100 was obtained by dilution using culture medium.
2.2. Tumor Cell Lines and Culture Conditions
2.2.1. Tumor Cell Lines
Cancer cell lines and culture media were purchased and provided by Oncodesign. The details of the cells lines are presented in Table 3 below.

TABLE 3

| N° | Cell lines | Origin | Source |
|---|---|---|---|
| | | BLOOD | |
| 1 | Daudi | Burkitt's lymphoma, B cells, peripheral blood | ATCC [a] |
| 2 | Hs 445 | Hodgkin's lymphoma, lymph node | ATCC |
| 3 | KARPAS-299 | Anaplastic large cell lymphoma, T cells, peripheral blood | DSMZ [b] |
| 4 | Mino | Mantle cell lymphoma, peripheral blood | ATCC |
| 5 | NAMALWA | Burkitt's lymphoma, B cells, peripheral blood | ATCC |
| 6 | Raji | Burkitt's lymphoma, B cells, peripheral blood | DSMZ |

TABLE 3-continued

| N° | Cell lines | Origin | Source |
|---|---|---|---|
| 7 | Ramos | Burkitt's lymphoma, B cells, peripheral blood | ATCC |
| 8 | SU-DHL-1 | Anaplastic large cell lymphoma, pleural effusion | DSMZ |
| 9 | Toledo | Non-Hodgkin's B cell lymphoma, peripheral blood | ATCC |
| 10 | U-937 | Lymphoma, histiocytic, macrophage differentiation, pleural effusion | ATCC |

[a] American Type Culture Collection, Manassas, Virginia, USA
[b] Deutsche Sammlung von Mikroorganismen und Zellkuturen Gmbh, Braunschweig, Germany 2.2.2. Culture Conditions
Tumor cells were grown as suspensions at 37° C. in a humidified atmosphere (5% $CO_2$, 95% air). The culture medium for each cell line is described in Table 4 below. For experimental use, cells were counted in a hemocytometer and their viability was assessed by 0.25% trypan blue exclusion.

TABLE 4

| | | Additives | | | | |
|---|---|---|---|---|---|---|
| Cell lines | Culture medium | FBS (%) | Glucose (g/l) | Glutamine (mM) | NaPyr (mM) | Hepes (mM) |
| Daudi | RPMI 1640 | 10 | — | 2 | 1 | 10 |
| Hs 445 | RPMI 1640 | 20 | 4.5 | 2 | 1 | 10 |
| KARPAS-299 | RPMI 1640 | 20 | — | 2 | — | — |
| Mino | RPMI 1640 | 15 | 4.5 | 2 | 1 | 10 |
| NAMALWA | RPMI 1640 | 10 | 2.5 | 2 | 1 | 10 |
| Raji | RPMI 1640 | 10 | — | 2 | 1 | 10 |
| Ramos | RPMI 1640 | 10 | — | 2 | 1 | 10 |
| SU-DHL-1 | RPMI 1640 | 10 | — | 2 | — | — |
| Toledo | RPMI 1640 | 15 | 4.5 | 2 | 1 | 10 |
| U-937 | RPMI 1640 | 10 | — | 2 | — | — |

*Mycoplasma* detection was performed using the MycoAlert® *Mycoplasma* Detection Kit (Lonza) in accordance with the manufacturer's instructions. All tested cells were found to be negative for *mycoplasma* contamination.

3. Experimental Design and Treatments 3.1. Cell Lines Amplification and Plating
Tumor cells were plated in 96-well flat-bottom microtitration plates (Nunc, Dutscher, Brumath, France) and incubated at 37° C. for 24 hours before treatment in 190 µl of drug-free and FBS-free culture medium.
Implantation densities for each cell lines are summarized in Table 5 below:

TABLE 5

| N° | Cell lines | Implantation densities (cells/well) |
|---|---|---|
| 1 | Daudi | 25,000 |
| 2 | Hs 445 | 25,000 |
| 3 | KARPAS-299 | 25,000 |
| 4 | Mino | 25,000 |
| 5 | NAMALWA | 15,000 |
| 6 | Raji | 20,000 |
| 7 | Ramos | 20,000 |
| 8 | SU-DHL-1 | 25,000 |
| 9 | Toledo | 25,000 |
| 10 | U-937 | 15,000 |

3.2. IC$_{50}$ Determination

Tumor cells were incubated for 4 hours with 10 concentrations of compounds in ¼ dilution step with a top dose of 400 µM (range 4×104 to 4×10-10 M), with 1% (final concentration) Triton X-100 as positive control and FBS-free culture medium as negative control. The cells (190 µl) were incubated in a 200 µl final volume of FBS-free culture medium containing test substances at 37° C. under 5% $CO_2$.

Three independent experiments were performed, each concentration being issued from quadruplicate. Control cells were treated with vehicle alone. At the end of treatments, the cytotoxic activity was evaluated by a MTS assay (see § 3.3 below).

Dilutions of tested compound as well as distribution to plates containing cells were performed using a Sciclone ALH 3000 liquid handling system (Caliper Life Sciences S.A.). According to automate use, a single range of concentrations was tested whatever the cell lines to be tested. The range was not adapted for each cell line.

3.3. MTS Assay

The in vitro cytotoxic activity of the test substance was revealed by a MTS assay (Baltorp et al.) using a novel tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT.

At the end of the cells treatment, 40 µl of a 0.22 µm filtered freshly combined solution of MTS (20 ml at 2 mg/ml, Ref G1111, Batch 235897, Exp 03/2009, Promega, Charbonnières, France) and PMS (1 ml at 0.92 mg/ml, Ref P9625, Batch 065K0961, Sigma) in Dulbecco's Phosphate Buffered Saline (DPBS, Ref 17-513Q, Batch 6MB0152, Cambrex), were added in each well. Culture plates were incubated for 2 h at 37° C. Absorbency (OD) were measured at 490 nm in each well using VICTOR$^{3TM}$ 1420 multilabeled counter (Wallac, PerkinElmer, Courtaboeuf, France).

4. Data Presentation 4.1. IC$_{50}$ Data was Determined as in Example 1

5. Results 5.1. LTX-302

All ten human lymphoma cell lines tested were sensitive to LTX-302 compound with IC$_{50}$ values ranging from 5.30±2.02 µM to 12.54±3.52 UM for U-937 and Raji cell lines, respectively.

Mean IC$_{50}$ value for LTX-302 compound obtained on 10 sensitive cell lines was 8.11±2.44 µM with a median value of 7.53 µM.

5.2. LTX-313

All ten human lymphoma cell lines tested were sensitive to LTX-313 compound with IC$_{50}$ values ranging from 3.21±2.81 µM to 16.08±4.86 UM for Ramos and Raji cell lines, respectively.

Mean IC$_{50}$ value for LTX-313 compound obtained on 10 sensitive cell lines was 7.05±3.91 µM with a median value of 5.89 µM.

5.3. LTX-315

All ten human lymphoma cell lines tested were sensitive to LTX-315 compound with IC$_{50}$ values ranging from 1.15±0.42 UM to 4.93±1.03 UM for U-937 and Raji cell lines, respectively.

Mean IC$_{50}$ value for LTX-315 compound obtained on 10 sensitive cell lines was 3.01±1.36 UM with a median value of 2.93 µM.

5.4. LTX-320

All ten human lymphoma cell lines tested were sensitive to LTX-320 compound with IC$_{50}$ values ranging from 2.22+NA µM to 11.26±3.42 µM for Hs 445 and Raji cell lines, respectively.

Mean IC$_{50}$ value for LTX-320 compound obtained on 10 sensitive cell lines was 5.03±2.82 UM with a median value of 4.84 µM.

5.5. LTX-329

All ten human lymphoma cell lines tested were sensitive to LTX-329 compound with IC$_{50}$ values ranging from 2.46±NA µM to 8.70±1.70 µM for Hs 445 and Raji cell lines, respectively.

Mean IC$_{50}$ value for LTX-329 compound obtained on 10 sensitive cell lines was 5.76±2.27 µM with a median value of 5.72 µM.

5.6. General Comments

KARPAS-299 and Raji cell lines are the most resistant cell lines whatever the LTX compound tested.

Hs 445, Ramos and U-937 cell lines are the most sensitive cell lines whatever the LTX compound tested.

LTX-315 compound is the most potent compound from the five compounds tested.

6. Conclusions

All five compounds tested (i.e. LTX-302, LTX-313, LTX-315, LTX-320 and LTX-329) exhibited cytolytic activity against the 10 human lymphoma cell lines tested with IC$_{50}$ values in micromolar range.

LTX-315 compound is the most potent compound tested with IC$_{50}$ values between 1 and 5 micromolar on all 10 human lymphoma cell lines tested.

Example 3

Haemolytic Activity In Vitro

Principle of Test

The haemolytic activity of the peptide LTX-315 against human red blood cells was measured.

Materials and Methods

Freshly collected human blood was centrifuged at 1500 rpm for 10 minutes in order to isolate the red blood cells. The red blood cells (RBC) were washed three times with PBS [35 mM phosphate buffer with 150 mM NaCl, pH 7.4] by centrifugation at 1500 rpm for 10 minutes, and adjusted to 10% haematocrit with PBS. LTX-315 solutions were added to give a final concentration range of the peptide from 1200 µg/ml to 1 µg/ml and an RBC concentration of 1%. The resulting suspension was incubated with agitation for one hour at 37° C. After incubation the suspension was centrifuged at 4000 rpm for 5 minutes, and the released haemoglobin were monitored by measuring the absorbance of the supernatant at 405 nm. PBS was used as negative control and assumed to cause no haemolysis. 0.1% Triton was used as positive control and assumed to cause complete haemolysis.

Test Substance: LTX-315

Reference substances: PBS (negative control) and Triton X-100 (positive control). Components of reaction mixtures: LTX-315, 10% Triton X-100, PBS and RBC (10% haematocrit). Details regarding these substances is presented in Table 6 below.

TABLE 6

| Concentration | PBS (μl) | RBC (μl) | LTX-315/Triton X-100 (μl) |
|---|---|---|---|
| Neg. Control | 630 | 70 | — |
| Pos. Control | 623 | 70 | 7 |
| 1200 | 150 | 50 | 300 (2 mg/ml stock) |
| 1000 | 200 | 50 | 250 (2 mg/ml stock) |
| 500 | 325 | 50 | 125 (2 mg/ml stock) |
| 100 | 595 | 70 | 35 (2 mg/ml stock) |
| 50 | 612.5 | 70 | 17.5 (2 mg/ml stock) |
| 10 | 560 | 70 | 70 (0.1 mg/ml stock) |
| 1 | 623 | 70 | 7 (0.1 mg/ml stock) |

Method of Evaluation:

Released haemoglobin was monitored by measuring the absorbance of the supernatant at 405 nm, and percent haemolysis was calculated by the equation:

$$\% \text{ Haemolysis} = (A_{405}\ LTX-315 - A_{405}\ PBS) / \\ (A_{405}0, 1\% \text{ Triton } X-100 - A_{405}\ PBS)] \times 100$$

LTX-315 concentration corresponding to 50% haemolysis (ECs) was determined from a dose-response curve.

Results

Mean value of five different experiments with standard deviation are presented in Table 7 below.

TABLE 7

| LTX-315 Concentration (μg/ml) | Mean cell death (%) | Standard Deviation | Number of parallels |
|---|---|---|---|
| 1,200 | 37.7 | 8.1445 | 3 |
| 1,000 | 38.2 | 9.5760 | 5 |
| 500 | 20.4 | 7.8613 | 5 |
| 100 | 3.6 | 1.1402 | 5 |
| 50 | 1.6 | 0.5477 | 5 |
| 10 | 0.6 | 0.8944 | 5 |
| 1 | 0.0 | 0.000 | 5 |

The data are also represented in FIG. 1. FIG. 1 shows that LTX-315 has a mean value of $EC_{50}$ higher than 1200 μg/ml (833 μM).

Example 4

Pharmacodynamic Effects Relative to Murine A20 B-Cell Lymphoma Tumours in Mice

Principle of Test

The aim of the study was to investigate the effect of LTX-315 at different dose levels on a murine A20 B-cell lymphoma in mice.

Materials and Methods

The administration took place by intratumoural injection of LTX-315 dissolved in sterile saline.

Female mice were inoculated subcutaneously in the abdomen with 5 million murine A20 cells (ATCC, LGC Promochem AB, Middlesex, England) in a volume of 50 μl. The mice were divided into four groups (see Table 8 below for details). The intratumoural treatment was initiated when the tumours had reached the desired size of approximately 5 mm in diameter (minimum of 20 mm$^2$).

Three dose levels of LTX-315, 1 mg (Group 1), 0.5 mg (Group 2) and 0.25 mg (Group 3) per injection, were investigated. The volume was 50 μl for all injections. LTX-315 was dissolved in sterile 0.9% NaCl water solution. This vehicle was used as control (Group 4). All four groups received three injections.

The mice were monitored during the study by measuring the tumours and weighing the animals regularly. The mice were followed until the maximum tumour burden of 125 mm$^2$ was reached, or until serious adverse events occurred (i.e. wound formation upon repeated treatments during the follow up period), then the mice were sacrificed. A calliper was used for tumour size measurements and weighing and physical examination were used as health control.

Animals: Specific pathogen-free female Balb/c mice, 6-8 weeks old, supplied form Harlan (England, UK)

Conditioning of animals: Animals were kept on standard laboratory chow and water.

Mean body weight, dose, route and treatment schedule is given in Table 8 below.

TABLE 8

| Group | Number of animals | Initial body weight (g; mean ± SE) | Treatment | Dose | Route | Schedule (Day*) |
|---|---|---|---|---|---|---|
| 1 | 7 | 20.36 ± 0.56 | Once daily | 1 mg in 50 μl (20 mg/ml) | Intra tumour | 1, 2, 3 |
| 2 | 7 | 19.96 ± 0.38 | Once daily | 0.5 mg in 50 μl (10 mg/ml) | Intra tumour | 1, 2, 3 |
| 3 | 9 | 20.11 ± 0.33 | Once daily | 0.25 mg in 50 μl (5 mg/ml) | Intra tumour | 1, 2, 3 |
| 4 | 7 | 19.73 ± 0.40 | Once daily | 50 μl 0.9% NaCl in H$_2$0 | Intra tumour | 1, 2, 3 |

*Day 1 is first day of treatment

Results:

The anti-tumour effect of the various treatments is presented as mean tumour size in Table 9 below.

TABLE 9

| Treatment | Mean tumour size (mm$^2$) at day 1* | Mean tumour size (mm$^2$) on day 4 | Mean tumour size (mm$^2$) on day 9 | Mean tumour size (mm$^2$) on day 14 |
|---|---|---|---|---|
| Group 1 | 25.82 ± 0.80 | 0 | 3.70 ± 2.40 | 12.43 ± 7.87 |
| Group 2 | 22.03 ± 0.63 | 0 | 11.41 ± 4.69 | 61.08 ± 23.84 |
| Group 3 | 21.25 ± 0.64 | 20.60 ± 5.71 | 68.49 ± 12.74 | 69.42 ± 17.70 |
| Group 4 | 22.79 ± 0.68 | 45.51 ± 5.27 | 57.79 ± 4.39 | 84.70 ± 7.35 |

*Tumour size prior to start of treatment at first day of treatment

The degree of tumour response in the different treatment groups is summarised in Table 10 below.

TABLE 10

| Animal Group | Tumour Response | | | Relapse of Tumour | Free of Tumour at end of Follow-Up |
| --- | --- | --- | --- | --- | --- |
| | no response | partial response | complete response | | |
| 1 | 0 | 42.8% (3/7) | 57.2% (4/7) | 25% | 42.8% (3/7) |
| 2 | 0 | 71.42% (2/7) | 28.57% (2/7) | 0% (0/2) | 28.57% (2/7) |
| 3 | 77.77% | 22.22% (0/9) | 0% | NA | 0 |
| 4 | 100% | NA | NA | NA | NA |

Discussion/Conclusions

In Group 3, receiving the lowest LTX-315 dose (0.25 mg/dose), a small inhibitory effect is observed during the first days. In Group 1 and Group 2, receiving LTX-315 doses of 1.0 mg/dose and 0.5 mg/dose respectively, all animals showed partial or complete tumour response. It was found that the anti-tumour activity resulted in a complete tumour response in 3 of 7 treated mice for the Group receiving the optimal dose (Group 1).

Generally stronger necrosis and more wound formation were observed in Group 1 compared to the other two groups. Except from the wound formation no other adverse events or toxic effects were observed in either of the groups of animals.

Both 1 mg and 0.5 mg of LTX-315 demonstrated a strong and rapid anti tumour effect in the first period of the study. However, as the study progresses more animals in Group 2 relapses than in Group 1.

Example 5

The Effect of LTX-315 on Murine CT26WT Colon Carcinoma Tumours in Mice

Materials and Methods

The administration takes place by intra-tumoural injection of LTX-315 dissolved in sterile saline (0.9% NaCl in sterile water).

Each of a total of 40 female mice was inoculated with five million murine CT26WT cells (ATCC, LGC Promochem AB, Boras, Sweden) subcutaneously on the abdomen surface in a volume of 50 µl. The mice were divided into five groups, 8 mice in each group. When the tumours reached the desired size of 20 mm$^2$ the treatment by intra tumoural injection was initiated. Group one was treated solely on day 1, Group two on day 1 and 2, Group three on day 1 and 3 and Group four on day 1, 2 and 3. All daily treatments were one single injection of 1.0 mg LTX-315 dissolved in 50 µl (20 mg/ml). Group five was treated with the 50 µl of vehicle for LTX-315 (Group 5).

The mice were monitored during the study by measuring the tumours (digital calliper) and weighing the animals regularly. The mice were followed until the maximum tumour burden of 125 mm$^2$ was reached, or until serious adverse events occurred (i.e. wound formation due to repeated injections), then the mice were sacrificed. Weighing and physical examination were used as health controls.

Animals: Specific pathogen-free female Balb/c mice, 6-8 weeks old, supplied form Harlan (England, UK) Conditioning of animals: Standard animal facility conditions. Mean body weight, dose, route and treatment schedule is given in Table 11 below.

TABLE 11

| Group | Number of animals | Initial body weight (g; mean ± SE) | Treatment | Dose | Route | Schedule (Day*) |
| --- | --- | --- | --- | --- | --- | --- |
| 1 | 8 | 19.00 ± 1.087 | Once daily | 1 mg in 50 µl (20 mg/ml) | Intra tumour | 1 |
| 2 | 8 | 19.56 ± 1.087 | Once daily | 1 mg in 50 µl (20 mg/ml) | Intra tumour | 1, 2 |
| 3 | 8 | 19.41 ± 0.8999 | Once daily | 1 mg in 50 µl (20 mg/ml) | Intra tumour | 1, 3 |
| 4 | 8 | 19.00 ± 0.9396 | Once daily | 1 mg in 50 µl (20 mg/ml) | Intra tumour | 1, 2, 3 |
| 5 (control) | 8 | 18.71 ± 0.7868 | Once daily | 50 µl 0.9% NaCl in H$_2$0 | Intra tumour | 1, 2, 3 |

*Day 1 is first day of treatment

Results

The anti-tumour effect of the various treatments is presented as mean tumour size in Table 12 below.

TABLE 12

| Treatment | Mean tumour size (mm$^2$) at day 1* | Mean tumour size (mm$^2$) on day 6 | Mean tumour size (mm$^2$) on day 10 | Mean tumour size (mm$^2$) on day 17 |
| --- | --- | --- | --- | --- |
| Group 1 | 22.69 ± 0.4070 | 4.343 ± 2.295 | 7.171 ± 4.035 | 3.712 ± 3.712 |
| Group 2 | 22.90 ± 1.155 | 1.458 ± 1.458 | 5.058 ± 4.014 | 6.644 ± 3.430 |
| Group 3 | 21.43 ± 1.141 | 2.983 ± 2.983 | 10.85 ± 7.553 | 0.00 ± 0.00 |
| Group 4 | 24.09 ± 1.653 | 0.00 ± 0.00 | 0.00 ± 0.00 | 1.308 ± 1.308 |
| Group 5 | 21.39 ± 1.683 | 33.77 ± 3.168 | 48.37 ± 7.035 | 40.64 ± 19.77 |

*Tumour size prior to start of treatment at first day of treatment

Complete tumour response was observed in the vast majority of all animals treated with LTX-315. The degree of tumour response in the different treatment groups is summarised in Table 13 below.

TABLE 13

| Animal Group | Tumour Response | | | Relapse of Tumour | Free of Tumour at end of Follow-Up |
| --- | --- | --- | --- | --- | --- |
| | no response | partial response | complete response | | |
| 1 | 0 | 27.5% | 62.5% | 20% (1/5) | 50% (4/8) |
| 2 | 0 | 12.5% | 87.5% | 71% (5/7) | 25% (2/8) |
| 3 | 12.5% | 0 | 87.5% | 29% (2/7) | 62.5% (5/8) |
| 4 | 0 | 0 | 100% (8/8) | 37.5% | 62.5% (5/8) |
| 5 | 100% (8/8) | NA | NA | NA | NA |

Discussion/Conclusions

The treatment was started when the tumours had reached the desired size of a minimum of 20 mm$^2$ and animals were sacrificed when the tumours reached the maximum tumour burden of 125 mm$^2$.

End of study was defined as day 17 when six out of eight control animals (Group 5) were sacrificed.

All LTX-315 treatment regimes resulted in a strong anti CT26WT-tumour effect.

Totally 27 of the 32 treated animals were observed with a complete tumour response and four with a partial response. Only one animal (in Group 3) did not have a response to the treatment. The results presented show that all four treated groups have very similar overall tumour response, the data also indicate that the degree of relapse of tumour was higher in Group 2 than in Group 1, 3 and 4. In addition fewer animals were observed to be free of tumour at end of follow-up in Group 2 (FIG. 2).

Necrosis and complete tumour response was observed in all the treated groups. In Group 1 four out of eight animals, in Group 2 two out of eight animals, in Group 3 five out of eight animals, and in Group 4 five out of eight animals showed complete tumour response. At this stage the tumour was completely necrotic and a wound crust formed at the location of the tumour.

Necrosis at the tumour site was seen in all treatment groups. Generally, animals in Group 2, 3 and 4 showed more necrosis, wound and crust formation than the animals in Group 1 that were given only one injection of LTX-315. Group 4 animals, which were given three injections, showed the most necrosis, wound and crust formation. The difference in necrosis between Group 1 and Group 4 was quite large but the animals given the highest number of treatments seemed to cope well. No toxic or other adverse effects besides local necrotic tissue and wound formation were observed in either of the treated groups of animals.

All four treatment regimes of LTX-315 tested demonstrated a strong anti tumour effect against murine CT26WT tumours.

The amount of necrosis, wound and crust formation was proportional to the number of LTX-315 treatments given.

Example 6

LTX-315 Activity Against Sensitive and Multidrug-Resistant Cancer Cells and Normal Human Cells Characteristics of the cell lines tested are presented in Table 14 below.

TABLE 14

| Cell line | Drug susceptibility | Origin | $IC_{50}$ μM |
|---|---|---|---|
| HL-60 | Sensitive | Acute promyelocytic leukemia | 2.07 |
| HL-60/ADR | Resistant | Acute promyelocytic leukemia | 3.01 |
| MCF-7 | Sensitive | Breast carcinoma | 1.94 |
| MCF-7/mdr | Resistant | Breast carcinoma | 1.96 |
| IGROV-1 | Sensitive | Ovary carcinoma | 6.37 |
| IGROV-1/CDDP | Resistant | Ovary carcinoma | 3.19 |
| K-562 | Sensitive | Chronic myeloid leukemia | 3.27 |
| K5627/Gleevec | Resistant | Chronic myeloid leukemia | 2.98 |
| HUV-EC-C | — | Normal endothelial cells | 23 |
| RBC | — | Red blood cells | 833 |

The above data shows the broad spectrum of activity of LTX-315 against various cancer cell lines and, significantly, a much weaker cytotoxic effect on normal human cells.

Example 7

Re-challenge with murine A20 B-cell lymphoma and murine CT26WT colon carcinoma cells in mice with complete tumour regression.

This study sought to investigate the effects of tumour growth in animals that had previously shown complete tumour regression following treatment with LTX-315.

Methods: Female Balb-c mice (n=4), previously treated with LTX-315, 1 mg) or (n=9); previously treated with LTX-315 0.5 or 1 mg) were re-inoculated (s.c. in the abdominal area) with either murine A20 B cell lymphoma cells or CT26WT colon carcinoma cells (5 million) respectively 6 weeks following initial treatment with LTX-315. Tumour growth was monitored for up to 36 days following re-inoculation.

Significant inhibition (P<0.006) of tumour growth was observed in all 4 mice treated previously with LTX-315 (1 mg) in study R315-03 compared with control animals (FIG. 2) and while relapse was seen in 1 animal, 3 weeks later, complete tumour regression was observed in the other 3 mice (FIG. 3).

In 9 mice previously treated with LTX-315 (0.5 or 1 mg) inhibition (P<0.01) of tumour growth was observed in comparison with control animals (FIG. 3). The sudden drop in tumour size in FIG. 20, after Day 18, is explained by the death of 6 animals bearing large tumours. Inhibition was observed in 7 mice and complete regression in 2 of the animals (FIG. 5).

Taken together these data suggest that complete tumour regression following initial treatment of solid murine tumours (murine A20 B cell lymphoma or CT26WT colon carcinoma) with LTX-315 resulted in a form of endogenous long-term protection against growth of the same tumours following re-inoculation. Inhibition of tumour growth was more pronounced in animals bearing A20 B cell lymphoma tumours when compared with animals bearing CT26WT colon tumours.

Example 8

Immunological effects of LTX-315 in a murine A20 B-cell lymphoma model. An in vivo adoptive spleen cell transfer pilot study.

This study was undertaken to investigate whether the long-term protection against growth of the same tumours following re-inoculation in animals observed in study R315-33 could be passively transferred to naive recipients via spleen cells taken from LTX-315-treated donor animals.

Ten female Balb/c mice (n=32) were each inoculated with A20 cells (5 million in 50 μL s.c.) on the abdominal surface. Once tumours had reached 20 mm$^2$ they were injected with LTX-315 (1 mg) injected intratumourally, once daily for 3 days, in a volume of 50 μL. Tumour size (mm$^2$) and body weight were subsequently monitored and a further injection of LTX-315 was given if any tumour re-growth was observed. Subsequently, mice showing complete tumour regression were sacrificed and used as donors for transfer of splenocytes while naive donor mice were used as controls. Spleens from donor mice were excised and cells isolated. Naive receiver mice were irradiated and divided into 2 groups. Group 1 received isolated splenocytes from cured mice, whereas group 2 received isolated splenocytes from naive mice. Freshly prepared cells were injected (20×106 per 100 μl) via the tail vein. Twenty four hours later receiver mice were inoculated with 5 million murine A20 B-cell lymphoma cells on the abdominal surface as described above. Tumour size and body weight were monitored until the maximum tumour burden of ~125 mm$^2$ was reached, or a serious adverse events occurred (i.e. wound formation due to tumour tissue necrosis) at which point mice were sacrificed.

Inhibition of tumour growth was observed in irradiated mice that received splenocytes isolated from animals that had shown complete tumour regression following treatment with LTX-315 when compared with control animals that received splenocytes from naive donors (FIG. 6). It was also noted that there was a difference in the colour and texture of the tumours in recipients of splenocytes from LTX-315-treated mice suggesting an immediate inflammatory response.

Based on these observations, the data provides evidence for an adaptive immune response in the animals that received splenocytes from animals that previously showed complete regression of A20-B lymphoma tumours following treatment with LTX-315. This data suggests that treatment with LTX-315 may confer long term protection against specific tumours by eliciting an immune response.

Example 9

The objective of the study was to investigate the anti-cancer effect of prophylactic vaccination with A20 lymphoma cells lysed by 10 mg/ml LTX-315:
(i) alone; and
(ii) in combination with 20 mg/ml LTX-315 injected at the vaccination site prior to the vaccine.

In total, two different treatment regimens were used.

Administration was by subcutaneous injection of LTX-315 dissolved in growth media containing A20 lymphoma cells. The cell-LTX-315 "cocktail" was left for 30 min prior to injection in order to assure complete lysis of the cancer cells.

Group 1 ("vaccine") mice were injected subcutaneously on the abdomen surface with 50 µl of a "cocktail" of ten million murine A20 cells (ATCC, LGC Promochem AB, Boras, Sweden) and 10 mg/ml LTX-315 ("A20 lysate"). Group 2 ("vaccine+adjuvant") mice were treated as per Group 1, but in addition were given 25 µl of 20 mg/ml LTX-315 subcutaneously at the site of vaccination 5 minutes prior to the A20 lysate injection. Group 3 ("control") mice received no treatment.

Six weeks after the treatment, all mice were inoculated with 5 million viable A20 B-cell lymphoma cells subcutaneously on the abdomen surface in a volume of 50 µl.

The mice were monitored during the study by measuring the tumour size and weighing the animals regularly. The mice were followed until the maximum tumour burden of ~130 mm² was reached, at which point the mice were sacrificed.

Materials and Methods

Animals: Specific pathogen-free female Balb/c mice, 6-8 weeks old, supplied from Harlan Laboratories (England, UK; www.harlan.com)

Conditioning of animals: Standard animal facility conditions at the University of Tromsø.

Test substance: Murine A20 cells lysed by LTX-315 (Lot 1013687), and LTX-315 (Lot 1013687) alone Test substance preparation: $10 \times 10^6$ A20 cells were added to a 50 µl 10 mg/ml LTX-315/vehicle ("A20 lysate"). The test substance was ready for use 30 minutes after mixing. LTX-315 alone was dissolved in 0.9% NaCl in sterile $H_2O$ Vehicle: RPMI-1640 w/2 mM L-glutamine or 0.9% NaCl in sterile $H_2O$ Reference substances: Not applicable Treatment of controls: Not applicable Method of evaluation: Tumour size measurements and health control by weighing and examination Additional data regarding method: A digital calliper was used for tumour size measurements and weighing and physical examination were used as health control Mean body weight, dose, route and treatment schedule are shown in Table 15 (below).

TABLE 15

| Group | No of animals | Initial body weight (g; mean ± SE) | Treatment | Cell numbers and dose | Route |
|---|---|---|---|---|---|
| 1 | 8 | 17.31 ± 0.3815 | Once | $10 \times 10^6$ A20 cells in 50 µl LTX-315 (10 mg/ml) | Subcutaneous |
| 2 | 8 | 17.14 ± 0.4633 | Once | 0.25 µl LTX-315 20 mg/ml) + $10 \times 10^6$ A20 cells in 50 µl LTX-315 (10 mg/ml) | Subcutaneous |
| 3 | 7 | 17.29 ± 0.3020 | Not treated | Not applicable | Not applicable |

Results:

The anti cancer effect of the various treatments is presented as mean tumour size in Table 16 below and a graphical presentation of the data is provided in FIG. 7. In Table 16, Day 1 was the day of inoculation of viable A20 cells six weeks post-vaccination.

TABLE 16

| Treatment | Mean tumour size (mm²) at day 4 | Mean tumour size (mm²) on day 11 | Mean tumour size (mm²) on day 16 | Mean tumour size (mm²) on day 21 |
|---|---|---|---|---|
| Group 1 | 9.515 ± 1.528 | 20.44 ± 6.191 | 36.21 ± 10.30 | 55.89 ± 15.27 |
| Group 2 | 7.315 ± 2.231 | 17.13 ± 5.078 | 29.13 ± 7.903 | 47.16 ± 13.54 |
| Group 3 | 10.25 ± 3.100 | 34.49 ± 8.298 | 56.04 ± 8.339 | 82.89 ± 14.06 |

Discussion/Conclusions

The inoculation of viable A20 B-cell lymphoma cells was accomplished 6 weeks after the treatment was given (day 1) and the animals were sacrificed when the tumours reached the maximum allowed tumour burden of ~130 mm².

The results show that the tumours developed more slowly in both LTX-315/A20-lysate treatment Groups as compared to the control Group. The median survival of Group 1 was 28 days, 33 days for Group 2, and 25 days for the control group (Group 3). Increase in median survival was 12% for Group 1 and 35% for Group 2 as compared to the control group (Group 3).

The data indicate a prolonged survival of the treated groups compared to the untreated control group. On day 34, when the last animal in the control group was sacrificed, 50% of the animals in Group 2 were still alive while 37.5% of the animals in Group 1 were still alive. End of study was defined as day 60. At this time-point, a total of 3 of the 16 treated animals had a complete regression of an initially developing tumour and were tumour free. At the end of the study 25% of animals from Group 1, and 12.5% of animals from Group 2 were observed to be tumour free.

Macroscopically there were morphological differences between the treated groups (Group 1 and 2) compared to the non-treated control group (Group 3). The developing tumours in the two treatment groups were observed to be whiter and harder than the tumours observed in the control group. This finding together with the slower growth rate of the tumours indicates that an anti-A20 cell immune response was induced by the vaccination with the cocktail of LTX-315 and lysed A20 cells.

Hence, LTX-315 may have a dual use by lysing the tumour cells and inducing release of danger signals from normal cells at the injection site.

Example 10

In this study, we investigated the tumoricidal effect of LTX-315 on human melanoma cells. The peptide internalized and was shown in association with mitochondria, ultimately leading to a lytic cell death. The LTX-315 peptide was designed to treat solid tumors with intratumoral injections through a two-stage mode of action: the first is the collapse of the tumor itself, while the second is the released damage-associated molecular pattern molecules (DAMPs) from the dying tumor cell, which can induce a subsequent immune protection against recurrences and metastastis.

Material and Methods
Reagents

LTX-315 and LTX-328 (K-A-Q-Dip-Q-K-Q-A-W-NH$_2$) were made on request by Bachem AG (Bubendorf, Switzerland) and Innovagen (Lund, Sweden), respectively. LTX-315 Pacific Blue and LTX-328 Pacific Blue were purchased on request from Innovagen (Lund, Sweden) Norud (Tromsø, Norway), respectively.

Cell Culture

The A375 cell line A375 (ECACC, 88113005) is a human malignant melanoma derived from patient material, and was purchased from Public Health England (PHE Culture Collections, Porton Down, Salisbury, UK). Cells were maintained as monolayer cultures in high glucose 4.5% DMEM supplemented with 10% FBS and 1% L-glutamine, but not as antibiotics (complete media). The cell line was grown in a humidified 5% CO$_2$ atmosphere at 37° C., and was regularly tested for the presence of *mycoplasma* with Myco-Alert (Lonza).

In Vitro Cytotoxicity, MTT-Assay

The cytotoxic effect of LTX-315 was investigated using the colorimetric MTT viability assay as described in Eliassen et al. (2002), 22(5): pp 2703-10. The A375 cells were seeded at a concentration of 1×10$^5$ cells/ml in a volume of 0.1 ml in 96-well plates, and allowed to adhere in a complete growth media overnight. The media was then removed and the cells were washed twice in serum-free, RPMI-1650 media, before adding LTX-315 dissolved in serum-free RPMI at concentrations ranging from 2.5-300 µg/ml, and incubated for 5-180 minutes. Cells treated with a serum-free RPMI were used as negative control cells, while cells treated with 1% Triton X-100 in serum-free media were used as a positive control. The final results were calculated using the mean of three experiments, each with triplicate wells.

Confocal Microscopy

Live cell imaging with unlabeled cells-A375 cells were seeded at 10,000 cells/well in a complete media in Nunc Lab-Tec 8-wells chambered covered glass (Sigma) pre-coated with 25 µg/ml human fibronectin (Sigma) that were allowed to adhere overnight. Cells were washed twice with a serum-free RPMI, treated with peptide dissolved in RPMI and investigated using Bright on a Leica TCS SP5 confocal microscope, with a 63X/1.2W objective. The microscope was equipped with an incubation chamber with CO$_2$ and temperature control.

Fixed cells, mitotracker—Cells were seeded as for live cell imaging, and treated with Mitotracker CMH2XROS (Invitrogen) at 100 nm for 15 minutes prior to peptide treatment. Cells were treated with 17 µM LTX-315, with negative control serum-free RPMI only. After 60 min of incubation, cells were analyzed using a Zeiss microscope. All confocal imaging experiments were subsequently conducted at least twice with similar results.

Fixed cells, fluorescence-labeled peptide-Subconfluential A375 cells were seeded at 8,000 cells/well as above, and transfected on the second day using the Lipofectamine LTX with Plus transfection reagents (Invitrogen) following the manufacturer's protocol. The mitochondria were labeled using the pDsRed2-Mito, and the nucleus was labeled using the GFP-Histon2B plasmid (Imaging Platform, University of Tromsø). A day after transfection, cells were washed twice with serum-free RPMI, and treated at different concentration and incubation periods with LTX-315 Pacific Blue or LTX-328 Pacific Blue. LTX-315 PB exhibited a similar cytotoxic profile as the unlabeled LTX-315 as determined by MTT assay.

Control cells were treated with unlabeled LTX-315 and also with serum-free RPMI only. After incubation, cells were fixed with 4% paraformaldehyde in PBS, and the wells were covered with Prolong Gold antifade (Invitrogen). Cells were further analyzed by use of a Leica TCS SP5 confocal microscope, with a 693, 1.2 W objective. Pacific Blue, GFP and Ds Red were excited using UV, with 488 and 561 lasers, and fluorescence channels were sequentially detected using the following band passes: UV: 420-480 nm (with attenuation), 488: 501-550 nm and 561: 576-676 nm.

TEM Electron Microscopy

A375 cells were seeded at 1×10$^5$ cells per well in 6-well plates and allowed to grow for three days to optimize membrane structures in the culture, and the media was changed on the second day. Cells were washed twice in serum-free RPMI before being treated with LTX-315 dissolved in serum-free RPMI at 5, 10 and 25 µg/ml, with serum-free RPMI as a negative control. Cells were then washed with PBS twice before fixation for 24 hours in 4° C. with 4% formaldehyde and 1% gluteralaldehyde in a Hepes buffer at pH 7.8. Dehydration and post-fixation protocols included incubation in a 5% buffered tannic acid and incubation in a 1% osmium-reduced ferrocyanide. Ultrathin sections were prepared, and uranyl acetate (5%) and Reynolds's lead citrate were used for staining and contrasting. Samples were examined on a JEOL JEM-1010 transmission electron microscope, and images were taken with an Olympus Morada side-mounted TEM CCD camera (Olympus soft imaging solutions, GmbH, Germany).

Fluorescence Measurement of Reactive Oxygen Species (ROS)

A DCFDA cellular reactive oxygen species detection assay kit was purchased from Abcam®, and A375 cells seeded in a 96-well Costar black clear bottom plate with 20,000 cells per well incubated in 37° C. 16 hours prior to DCFDA assay. Cells were washed with a 100 μL/well of pre-warmed PBS one time, and incubated with 20 μM of DCFDA in a buffer solution supplied with the kit at 37° C. in a cell culture incubator for 45 min, and then washed again with a buffer solution of 100 μL/well. The cells were then stimulated with a 100 μL/well LTX-315 peptide dissolved in a buffer solution at concentrations of 17 μM for 30 min, and cells not treated were used as a negative control. The fluorescence intensity was determined at an excitation wavelength of 485 nm and an emission wavelength of 530 nm on a FLUOstar Galaxy plate reader.

Release of High Mobility-Group Box-1 (HMGB1)

A375 cells were seeded with $3 \times 10^5$ cells/well in 6-well plates in a complete media, and allowed to adhere overnight. Cells were treated with LTX-315 or LTX-328 at 35 μM, and incubated at 37° C. and 5% $CO_2$ for different time points (5, 10, 15, 30, 60 min), and negative controls were serum-free RPMI-1650. Supernatants (S) were collected and centrifuged at 1,400 g for five minutes, and cell lysates (L) were harvested after washing with PBS twice and then subsequently lysed using a 4× Sample buffer (Invitrogen, number), 0.1 M DTT (Sigma number) and water. Supernatants were concentrated using Amicon Ultra 50K centrifugal filters (Millipore UFC505024), and the cell lysate was sonicated. Both supernatants and lysate were boiled and resolved in a 10% sodium dodecyl sulfate polyacrylamide gel electrophoresis (SDS-PAGE), and then electro transferred to a polyvindiline difluoride (PVDF) membrane (Millipore). The membrane was blocked in 5% milk and incubated with the HMGB1 antibody (rabbit, polyclonal, abcam ab 18256); the membrane was then rinsed several times with TBST, incubated with a horseradish peroxidase (HRP)-conjugated secondary antibody (abcam ab6721), rinsed again with TBST and then developed using WB Luminol Reagent (Santa Cruz Biotechnology, Heidelberg, Germany).

Release of Cytochrome-C

A375 cells were seeded as with HMGB1 studies, and treated with 35 μM for different time points (5, 15, 45). Supernatants were collected and concentrated as with HMGB1 studies, and samples from the supernatants were analyzed using a 4.5 hour solid form Cytochrome C-Elisa kit (R&D Systems, USA, #DCTC0) following the manufacturer's description. Shortly thereafter, a 50% diluted sample was analyzed and the optical density was determined using a microplate reader set at 450 nm, and this reading was then subtracted from the reading at 540 nm. A standard curve was generated for each set of samples assayed. Samples were run in four parallels, and the cytochrome-c released into the supernatant was expressed as a fold over the level of cytochrome-c in the supernatant of untreated cells.

Release of ATP

The supernatant of LTX-315-treated A375 cells was analyzed using an Enliten ATP luciferase assay kit (Promega, USA). Cells were then seeded as with an ROS assay, and treated with LTX-315 in different incubation times, from 1 to 15 minutes with two parallels, which was then conducted three times. Negative controls were untreated A375 cells exposed to serum-free media alone. Samples were diluted at 1:50 and 1:100, and analyzed with a Luminoscan RT luminometer according to the manufacturer's protocol.

Statistical Analysis

All data represent at least two independent experiments with at least two parallels, which were expressed as the mean±SD. Cytochrome-C release and ATP release data was compared using one-way ANOVA and a multiple comparison test, and we considered the P-value<0.05 to indicate statistical significance.

Results

Cytotoxic Effect of LTX-315 on Melanoma Cells

To investigate the effect of LTX-315 on A735 melanoma cells in vitro, we determined the IC-50 values for the peptide by a cell viability assay MTT at different incubation times. The IC-50 value was 30 μM after only five minutes of incubation, and progressed to 14 μM after 90 minutes. Further incubation up to 180 minutes did not offer any additional effect (FIG. 8).

LTX-315 Treatment Causes Rapid Cell Lysis

We next wanted to assess the cell morphology of A735 melanoma cells treated with LTX-315. Cells were treated with LTX-315 at an IC-50 value, and investigated by bright field confocal microscopy. Treated cells displayed a rapid change from a normal epithelial morphology to a total collapse of the cells with an extrusion of cytoplasmic content, which was preceded by a rounding up of the cell (data not shown). These changes typically occurred within 15-60 minutes at an IC-50 value in the majority of the cells.

LTX-315 Internalizes and Targets the Mitochondria

Figure 10:
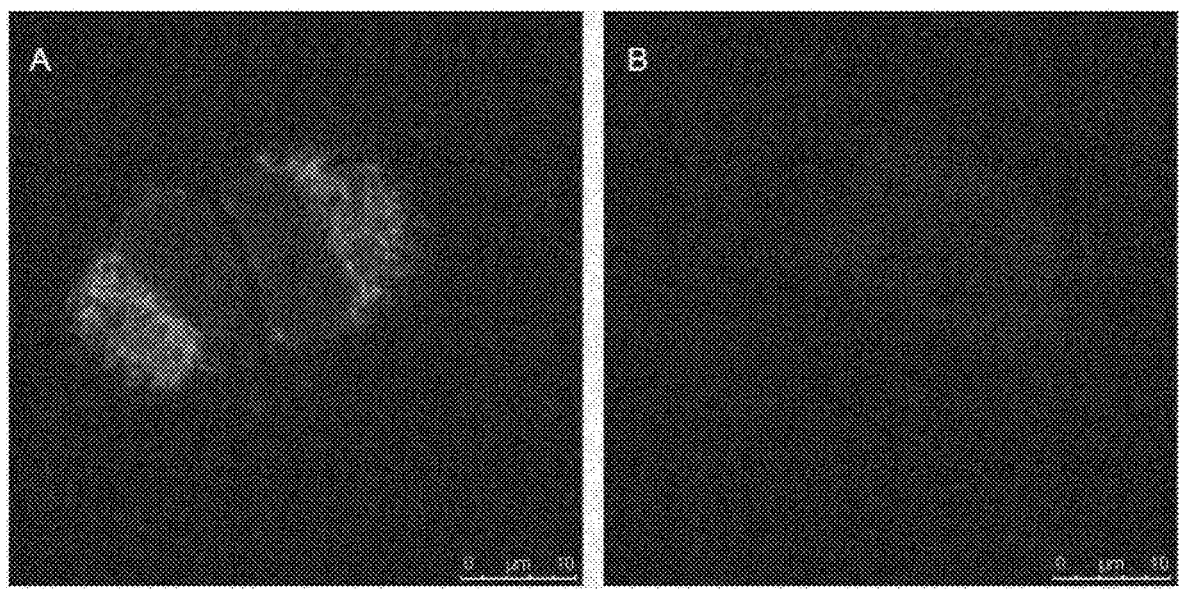

To investigate the internalization and fate of the peptide within the cells, LTX-315 was labeled with Pacific Blue and incubated with cells at concentrations of 3 μM and 1.5 μM, respectively. The labeled LTX-315 rapidly penetrated the plasma membrane and at 1.5 μM, the peptide showed an accumulation around the mitochondria after 30 minutes of incubation but was not detected in the cell nucleus (FIG. 9). The labeled non-lytic mock-sequence peptide LTX-328 did not demonstrate any internalization at any concentration or incubation time tested (FIG. 10).

LTX-315 Induces Ultra-Structural Changes in Cells

We further evaluated the ultrastructural changes in treated cells by performing transmission electron microscopy (TEM), in which A375 cells were treated with either peptides dissolved directly in media or in media alone. A significant number of the cells treated with a low concentration (3.5 μM) of the LTX-315 peptide for 60 minutes showed vacuolization, as well as some altering of the mitochondrial morphology (FIG. 11). The mitochondria appeared to be less electron-dense, also exhibiting some degree of reorganization, with the cristae lying further apart or not visible at all. The number of necrotic cells in these samples was less than 5%. In these low concentrations, vacuolization of the cytoplasm was observed. Another common finding in these samples were peripherally placed vacuoles, which were lined with a single membrane layer containing a homogenous material (FIG. 11B). When cells were treated with higher concentration (17 μM) for 60 min, approximately 40% of them displayed a necrotic morphology with a loss of plasma membrane integrity (FIG. 11C&E). The cells that were still intact displayed a great heterogeneity, from a normal appearance with microvilli to a round appearance, with mitochondria clearly affected. In this high concentration, only 4% of the cells investigated displayed vacuolization, and chromatin condensation was not visible in this material at any peptide concentration tested. These results demonstrate that LTX-315 kills the tumor cells with a lytic mode of action, while lower concentrations cause the cells to undergo ultrastructure changes, such as vacuolization and an altered mitochondrial morphology. Moreover, no significant morphological changes suggestive of apoptotic cell death were observed.

In a separate experiment, exposure of LTX-315 at 10 μg/ml to human A547 cells (an ovarian melanoma cell line) led to disintegration of the mitochondrial membrane (FIG. 16).

LTX-315 Treatment Leads to Extracellular ATP Release

DAMPs are molecules that are released from intracellular sources during cellular damage. DAMPs can initiate and perpetuate an immune response through binding to Pattern Recognition Receptors (PRRs) on Antigen Presenting Cells (APCs). Among commonly known DAMPs are ATP, HMGB1, Calreticulin, Cytochrome C, mitochondrial DNA and Reactive oxygen species (ROS). We next wanted to investigate whether ATP was released into the supernatant from cells treated with LTX-315. Hence, the supernatant from treated and non-treated cells analyzed using luciferase detection assay. As shown in FIG. 15, ATP was detected in the supernatant as early as after 5 minutes of treatment with LTX-315, and the release was concentration-dependent.

LTX-315 Treatment Induces Cytochrome-C Release in Supernatant

To assess whether LTX-315-treated cells released cytochrome-C into the medium, A375 cells were treated with LTX-315 at 35 µM at different time points (5, 15, 45 min). The supernatant was subsequently analyzed using an ELISA assay. Cells treated with 35 µM value had three times more cytochrome-C in the supernatant compared to untreated control cells. The increase in cytochrome-C was detected after only five minutes of treatment, and there was also an increase after 15 and 45 minutes of peptide treatment, respectively (FIG. 13).

LTX-315 Treatment Leads to Extracellular HMGB1 Release

HMGB 1 is a non-histone, chromatin-binding nuclear protein. Once passively released from necrotic cells, HMGB1 is able to trigger the functional maturation of dendritic cells, cytokine stimulation and chemotaxis among several immunopotentiating effects.

HMGB 1 is normally found in the cell nucleus and would be expected in a cell lysate of healthy cells, though not in the culture media (supernatant). In order to assess the release of HMGB 1 from LTX-315-treated cells, we measured the translocation and free HMGB1 from the nuclear compartment within the cell lysate into the cell supernatant.

Both cell lysate and the cell supernatant of LTX-315- and LTX-328-treated A375 melanoma cells were analyzed using a Western blot. Cells were treated with 35 µM of either LTX-315 or LTX-328, with a gradual translocation from the cell lysate to the supernatant detected in the LTX-315-treated melanoma cells, but not in the cells treated with the mock sequence peptide LTX-328 or a serum-free medium only (FIG. 14).

LTX-315 Treatment Causes the Production of Reactive Oxygen Species (ROS) in A375 Melanoma Cells The ROS generation following LTX-315 treatment was measured by CH2DCFDA fluorometric assay. Significant amounts of ROS were generated after 15 minutes of incubation with LTX-315, and the ROS levels were concentration-dependent (FIG. 12).

Discussion

LTX-315 labeled with the fluorescent molecule Pacific Blue was internalized within minutes after incubation with A375 melanoma cells, and was distributed in the cytoplasm (FIG. 9). At low concentrations, accumulation of the peptide around the mitochondria was evident, whereas at higher concentrations the peptide was more spread within the cytoplasm and accumulated in circular structures closer to the cell membrane (FIG. 10). If the peptide attacks the mitochondrial membrane, a decrease or even a total collapse of the mitochondrial membrane potential would be expected. A confocal imaging of cells with the membrane potential-dependent mitochondrial stain Mitotracker CMXh2ROS showed a loss of mitochondrial signal a short time after peptide treatment (data not shown). The loss of the signal shows that the peptide interaction with the mitochondria causes a loss of mitochondrial membrane potential, which is crucial for the mitochondria's most important cellular functions. An altered mitochondrial morphology was also demonstrated with TEM. Cells treated with LTX-315 for 60 minutes had less electron-dense mitochondria with an altered organization of the cristae, as well as vacuolization within the mitochondria compared to untreated cells (FIG. 11). Furthermore, vacuolization was evident in approximately 20% of cells treated with 3.5 µM of LTX-315. When the mitochondria are dysfunctional, free oxygen radicals (ROS) may be formed, and by using fluorometric assays we demonstrated ROS formation within a few minutes after peptide treatment (FIG. 12).

In this study, we demonstrate that treatment with the LTX-315 peptide causes an increase in ROS levels in A375 melanoma cells after treatment. One explanation for these higher levels of ROS following peptide treatment could be that the peptide enters the cells and targets the mitochondria, and the dysfunctional mitochondria then releases ROS. Through an ELISA assay, we detected the release of cytochrome-C in the supernatant of peptide-treated cells after only a few minutes of treatment (FIG. 13). Cytochrome-C is a mitochondrial protein released from the intermembrane space and into the cytosol when the outer mitochondrial membrane is perturbed, and by binding to the apoptotic protease activating factor-1 (Apaf-1) it is also a part of the apoptotic cascade that eventually leads to cell death by apoptosis. However, if cytochrome-C is found in the extracellular space, it has been reported to act as a pro-inflammatory mediator, thus activating NF-kB and inducing cytokine and chemokine production. The transition of HMGB1 from the cellular compartment to the extracellular compartment was detected using a western blot (FIG. 14). When the nuclear protein HMBG1 is released into the extracellular fluid, it functions as a DAMP, and can bind to both the PRR TLRs and to the RAGE receptors; the activation of these may lead to a number of inflammatory responses such as the transcription of pro-inflammatory cytokines. We also detected ATP released in the supernatant after peptide incubation (FIG. 15), and presented extracellularly it functions as a DAMP by activating the purinerg P2RX7 receptors on the DC. This receptor not only functions as a pore that opens for small cationic and later bigger molecules after binding to ATP, its activation also causes the processing and release of the pro-inflammatory cytokine IL-1β.

In summary, our data suggests that LTX-315 induces lytic cell death in cancer cells, not only by direct attack on the plasma membrane, but also as a result of an injury to vital intracellular organelles after the internalization of the peptide at concentrations too low to cause an immediate loss of plasma membrane integrity. We demonstrate that the peptide treatment causes the release of several DAMPs such as CytC, ATP, HMGB1 and ROS. The DAMPs may affect the cellular integrity of the damaged cells in several ways, but are also associated with so-called immunogenic cell death. The release of tumor-specific antigens into the extracellular compartment, together with potent immune stimulatory molecules (DAMPs) such as ATP, CytC and HMGB1, can give a strong immune response. In turn, these factors will lead to a maturation and activation of DCs and other accessory cells of the adaptive immune system.

Example 11

The combination of LTX-315 with either an anti-programmed cell death protein 1 (PD-1) antibody or an anti-cytotoxic T-lymphocyte-associated protein 4 (CTLA-4) antibody was assayed in a mouse MCA205 sarcoma model. Seven animals were studied per group. For each study, two independent experiments were performed yielding identical results. Anova statistical analyses were performed.

The anti-PD-1 antibody used in this study was a murine IgG isotype. The anti-CTLA-4 antibody was a rat IgG isotype. Both antibodies were purchased from eBioscience.

FIGS. 17a, 18a, 19a and 20a show the timings and administration routes of LTX-315 and the antibodies in the various studies. Thus, at day-8 mice were inoculated with MCA205 cancer cells and palpable tumours were allowed to form. LTX-315 was then administered intratumorally on the days shown in the Figures and the anti-PD-1 or anti-CTLA-4 antibodies were administered i.p. on the days shown.

An adaptive immunity study using the combination of anti-CTLA-4 antibody and LTX-315 was carried out in a similar manner to that previously discussed.

The findings of these studies are discussed in the legend of FIGS. 17 to 20. As the effects of anti-PD1 antibodies occur in the local tumour microenvironment (anti-CTLA-4 works in lymphatic tissue), it is predicted that the combination of the peptidic compound with anti-PD1 antibodies would be more pronounced in a clinical setting in comparison to this single tumour model which is not representative of metastatic disease.

Example 12

The combination of LTX-315 with an anti-programmed cell death protein 1 ligand (PD-L1) antibody was assayed in a mouse EMT-6 mammary carcinoma model.

Materials and Methods

The anti-PD-L1 antibody had the following characteristics: ref: BE0101, Bioxcell; clone 10F.9G2; reactivity: mouse; isotype: Rat IgG2b. LTX-315 was prepared at a dose of 0.5 mg/50 µL in 0.9% sodium chloride solution. Anti-PD-L1 antibody was prepared at a concentration in phosphate-buffered saline and was administered at a dose of 10 mg/kg. LTX-315 was injected into the tumour grafted on the right flank of the mice, anti-PD-L1 antibody was injected into the peritoneal cavity of the mice.

The EMT-6 cell line was established from a transplantable murine mammary carcinoma that arose in a BALB/cCRGL mouse after implantation of a hyperplastic mammary alveolar nodule (VOLENEC F J., et al., J Surg Oncol. 13(1):39-44, 1980).

Cell culture conditions: EMT-6 tumor cells were grown as a monolayer at 37° C. in a humidified atmosphere (5% $CO_2$, 95% air). The culture medium was RPMI 1640 containing 2 mM L-glutamine (ref: BE12-702F, Lonza, Verviers, Belgium) supplemented with 10% fetal bovine serum (ref: 3302, Lonza). EMT-6 tumor cells are adherent to plastic flasks. For experimental use, tumor cells were detached from the culture flask by a 5-minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability were assessed by 0.25% trypan blue exclusion assay.

Use of mice: Healthy female Balb/C mice, 6-8 weeks old at reception, were obtained from CHARLES RIVER (L'Arbresles, France) and from Janvier (France). Mice were maintained in SPF health status according to the FELASA guidelines. Mouse housing and experimental procedures were realized according to the French and European Regulations (Principe d'éthique de l'expérimentation animale, Directive no 2010/63 CEE du 22 September 2010, Décret no 2013-118 du 01 février 2013) and the NRC Guide for the Care and Use of Laboratory Animals (NRC Guide for the Care and Use of Laboratory Animals). The animal facility was authorized by the French authorities (Agreement No B 21 231 011 EA). All procedures using mice were submitted to the Animal Care and Use Committee of Oncodesign (Oncomet) agreed by French authorities (CNREEA agreement No 91). Mice were individually identified with a RFID transponder and each cage was labeled with a specific code.

Housing conditions: Mice were maintained in housing rooms under controlled environmental conditions: Temperature: 22±2° C. Humidity 55±10%, Photoperiod (12 h light/12 h dark), HEPA filtered air, 15 air exchanges per hour with no recirculation. Mice enclosures provided sterile and adequate space with bedding material, food and water, environmental and social enrichment (group housing) as described: Top filter polycarbonate Eurostandard Type III or IV cages, Corn cob bedding (ref: LAB COB 12, SERLAB, France), 25 kGy Irradiated diet (Ssniff® Soest, Germany), Complete food for immunecompetent rodents—R/M-H Extrudate, Sterile, filtrated at 0.2 µm water, and Environmental enrichment (SIZZLE-dri kraft-D20004 SERLAB, France).

Induction of MET-6 tumours in mice: A first tumor was induced by subcutaneous injection of $1 \times 10^6$ of EMT-6 cells in 200 µL of RPMI 1640 into the right flank of Balb/C female mice. The day of tumor cell injection in the right flank was considered as D0. A second tumor was induced by subcutaneous injection of $1 \times 10^5$ of EMT-6 cells in 200 µL of RPMI 1640 into the left flank of Balb/C female mice. The day of tumor cell injection in the left flank was considered as D3.

Treatment schedule: Mice were randomized according to their body weight on D3 into four groups each of 5 mice (group 1) or 10 mice (groups 3, 5 and 7) using Vivo Manager® software (Biosystemes, Couternon, France). A statistical test (analysis of variance) was performed to test for homogeneity between groups. A statistical test (analysis of variance) was performed to test for homogeneity between groups.

The treatment schedule was as follows: the mice from group 1 were not treated; the mice from group 3 received a total of 3 intratumoral injections of LTX135; the mice from group 5 received a total of 6 IP injections of anti-PD-L1; and the mice from group 7 received a total of 3 intratumoral injections of LTX315 and a total of 6 IP injections of anti-PD-L1.

The treatment schedule is summarized in Table 17 below:

TABLE 17

| Group | No. Mice | Treatment | Treatment Schedule |
|---|---|---|---|
| G1 | 5 | Untreated | — |
| G3 | 10 | LTX315 | Q1Dx3 |

TABLE 17-continued

| Group | No. Mice | Treatment | Treatment Schedule |
|---|---|---|---|
| G5 | 10 | Anti-PD-L1 | Q2Dx6 |
| G7 | 10 | LTX315 | Q1Dx3 |
|   |   | Anti-PD-L1 | Q2Dx6 |

Q1Dx3 = one injection for 3 consecutive days (total of 3 injections).
Q2DX6 = one injection every 2 days (total of 6 injections).

Mouse monitoring: All study data, including mouse body weight measurements, tumour volume, clinical and mortality records, and treatment were scheduled and recorded on Vivo Manager® database (Biosystemes, Dijon, France). The viability and behaviour was recorded every day. Body weights were measured thrice a week. The length and width of the tumor was measured three times a week with calipers and the volume of the tumour was estimated by the following formula: tumour volume=(width2×length)/2 (SIMPSON-HERREN L. et al. Cancer Chemotherapy Rep., 54: 143, 1970).

Statistical Tests: All statistical analyses were performed using Vivo Manager® software (Biosystemes, Couternon, France). Statistical analyses of mean body weights, MBWC, mean tumor volumes at randomization, mean tumor volumes, mean times to reach mean tumour volumes and mean tumor doubling times were performed using ANOVA and pairwise tests were performed using the Bonferroni/Dunn correction in case of significant ANOVA results. A p value<0.05 was considered as significant.

Results

As shown in FIG. 21, 50% of the test mice survived for more than 50 days after tumour induction when administered with both LTX-315 and anti-PD-L1 antibody, compared to 40% of the test mice treated with anti-PD-L1 antibody alone, 30% of the test mice treated with LTX-315 alone and none of the untreated mice. This shows that the combination therapy is more effective at both directly treating tumours (treating the tumour in the right flank of the mouse) and inducing an adaptive immunity response (treating the tumour in the left flank of the mouse).

Details regarding the percentage of mice that show total tumour regression in the right and/or left flank are shown in Table 18 below. Mice were tested at day 52 after inoculation or when sacrificed.

TABLE 18

| Group | Flank | Proportion of Mice |
|---|---|---|
| G1 | Right | 0% |
|   | Left | 0% |
| G3 | Right | 30% |
|   | Left | 10% |
| G5 | Right | 20% |
|   | Left | 20% |
| G7 | Right | 20% |
|   | Left | 40% |

The table shows that the combination of LTX-315 and anti-PD-L1 antibody is particularly effective in inducing adaptive immunity, as 40% of the mice treated with the combination (G7) showed total regression of the tumour in the left flank, compared to 10% of mice treated with LTX-315 alone (G3), 20% of mice treated with anti-PD-L1 antibody alone (G5) and none of the untreated mice (G1).

Median and mean tumour volume for each cohort was measured and while G3 and G5 always gave significantly lower volumes than G1, G7 was always clearly the best performing cohort.

It will be appreciated that it is not intended to limit the present invention to the above specific embodiments only, numerous embodiments, modifications and improvements being readily apparent to one of ordinary skill in the art without departing from the scope of the appended claims.

SEQUENCE LISTING

```
Sequence total quantity: 43
SEQ ID NO: 1            moltype =     length =
SEQUENCE: 1
000

SEQ ID NO: 2            moltype =     length =
SEQUENCE: 2
000

SEQ ID NO: 3            moltype =     length =
SEQUENCE: 3
000

SEQ ID NO: 4            moltype =     length =
SEQUENCE: 4
000

SEQ ID NO: 5            moltype =     length =
SEQUENCE: 5
000

SEQ ID NO: 6            moltype =     length =
SEQUENCE: 6
000

SEQ ID NO: 7            moltype =     length =
SEQUENCE: 7
000

SEQ ID NO: 8            moltype =     length =
SEQUENCE: 8
```

```
000

SEQ ID NO: 9           moltype =   length =
SEQUENCE: 9
000

SEQ ID NO: 10          moltype = AA   length = 9
FEATURE                Location/Qualifiers
REGION                 1..9
                       note = Synthetic sequence
source                 1..9
                       mol_type = protein
                       organism = synthetic construct
MOD_RES                1
                       note = Diphenylalanine
SEQUENCE: 10
AKKWWKKWK                                                                  9

SEQ ID NO: 11          moltype = AA   length = 9
FEATURE                Location/Qualifiers
REGION                 1..9
                       note = Synthetic sequence
source                 1..9
                       mol_type = protein
                       organism = synthetic construct
MOD_RES                5
                       note = diphenylalanine
SEQUENCE: 11
WKKWAKKWK                                                                  9

SEQ ID NO: 12          moltype = AA   length = 9
FEATURE                Location/Qualifiers
REGION                 1..9
                       note = Synthetic sequence
source                 1..9
                       mol_type = protein
                       organism = synthetic construct
MOD_RES                8
                       note = diphenylalanine
SEQUENCE: 12
WKKWWKKAK                                                                  9

SEQ ID NO: 13          moltype = AA   length = 9
FEATURE                Location/Qualifiers
REGION                 1..9
                       note = Synthetic sequence
source                 1..9
                       mol_type = protein
                       organism = synthetic construct
MOD_RES                1
                       note = biphenylalanine
SEQUENCE: 13
AKKWWKKWK                                                                  9

SEQ ID NO: 14          moltype = AA   length = 9
FEATURE                Location/Qualifiers
REGION                 1..9
                       note = Synthetic sequence
source                 1..9
                       mol_type = protein
                       organism = synthetic construct
MOD_RES                4
                       note = biphenylalanine
SEQUENCE: 14
WKKAWKKWK                                                                  9

SEQ ID NO: 15          moltype = AA   length = 9
FEATURE                Location/Qualifiers
REGION                 1..9
                       note = Synthetic sequence
source                 1..9
                       mol_type = protein
                       organism = synthetic construct
MOD_RES                5
                       note = biphenylalanine
REGION                 1..9
                       note = D-amino acid
SEQUENCE: 15
WKKWAKKWK                                                                  9
```

```
SEQ ID NO: 16            moltype = AA   length = 9
FEATURE                  Location/Qualifiers
REGION                   1..9
                         note = Synthetic sequence
source                   1..9
                         mol_type = protein
                         organism = synthetic construct
MOD_RES                  4
                         note = diphenylalanine
SEQUENCE: 16
KKWAKKWWK                                                                 9

SEQ ID NO: 17            moltype = AA   length = 9
FEATURE                  Location/Qualifiers
REGION                   1..9
                         note = Synthetic sequence
REGION                   1..2
                         note = D-amino acid
MOD_RES                  4
                         note = diphenylalanine
REGION                   5..6
                         note = D-amino acid
SITE                     9
                         note = D-amino acid
source                   1..9
                         mol_type = protein
                         organism = synthetic construct
SEQUENCE: 17
KKWAKKWWK                                                                 9

SEQ ID NO: 18            moltype = AA   length = 9
FEATURE                  Location/Qualifiers
REGION                   1..9
                         note = Synthetic sequence
MOD_RES                  4
                         note = diphenylalanine
MOD_RES                  8
                         note = diphenylalanine
source                   1..9
                         mol_type = protein
                         organism = synthetic construct
SEQUENCE: 18
KKWAKKWAK                                                                 9

SEQ ID NO: 19            moltype = AA   length = 9
FEATURE                  Location/Qualifiers
REGION                   1..9
                         note = Synthetic sequence
MOD_RES                  4
                         note = biphenylalanine
source                   1..9
                         mol_type = protein
                         organism = synthetic construct
SEQUENCE: 19
KKWAKKWWK                                                                 9

SEQ ID NO: 20            moltype = AA   length = 9
FEATURE                  Location/Qualifiers
REGION                   1..9
                         note = Synthetic sequence
MOD_RES                  2
                         note = biphenylalanine
source                   1..9
                         mol_type = protein
                         organism = synthetic construct
SEQUENCE: 20
KAKKWWKKW                                                                 9

SEQ ID NO: 21            moltype = AA   length = 9
FEATURE                  Location/Qualifiers
REGION                   1..9
                         note = Synthetic sequence
MOD_RES                  3
                         note = biphenylalanine
source                   1..9
                         mol_type = protein
                         organism = synthetic construct
SEQUENCE: 21
```

```
KKAWKKWWK                                                                              9

SEQ ID NO: 22          moltype = AA   length = 9
FEATURE                Location/Qualifiers
REGION                 1..9
                       note = Synthetic sequence
MOD_RES                7
                       note = diphenylalanine
source                 1..9
                       mol_type = protein
                       organism = synthetic construct SEQUENCE: 22
KKWWKKAWK                                                                              9

SEQ ID NO: 23          moltype = AA   length = 9
FEATURE                Location/Qualifiers
REGION                 1..9
                       note = Synthetic sequence
MOD_RES                8
                       note = diphenylalanine
source                 1..9
                       mol_type = protein
                       organism = synthetic construct SEQUENCE: 23
KKWWKKWAK                                                                              9

SEQ ID NO: 24          moltype = AA   length = 9
FEATURE                Location/Qualifiers
REGION                 1..9
                       note = Synthetic sequence
MOD_RES                3
                       note = diphenylalanine
source                 1..9
                       mol_type = protein
                       organism = synthetic construct SEQUENCE: 24
KWAKKWWKK                                                                              9

SEQ ID NO: 25          moltype = AA   length = 9
FEATURE                Location/Qualifiers
REGION                 1..9
                       note = Synthetic sequence
MOD_RES                7
                       note = diphenylalanine
source                 1..9
                       mol_type = protein
                       organism = synthetic construct SEQUENCE: 25
KKWWKWAKK                                                                              9

SEQ ID NO: 26          moltype =     length =
SEQUENCE: 26
000

SEQ ID NO: 27          moltype =     length =
SEQUENCE: 27
000

SEQ ID NO: 28          moltype = AA   length = 9
FEATURE                Location/Qualifiers
REGION                 1..9
                       note = Synthetic sequence
MOD_RES                4
                       note = diphenylalanine
source                 1..9
                       mol_type = protein
                       organism = synthetic construct SEQUENCE: 28
RRWARRWWR                                                                              9

SEQ ID NO: 29          moltype = AA   length = 9
FEATURE                Location/Qualifiers
REGION                 1..9
                       note = Synthetic sequence
MOD_RES                6
                       note = diphenylalanine
source                 1..9
                       mol_type = protein
                       organism = synthetic construct
```

```
SEQUENCE: 29
KWWKKAWKK                                                                                9

SEQ ID NO: 30           moltype = AA  length = 9
FEATURE                 Location/Qualifiers
REGION                  1..9
                        note = Synthetic sequence
MOD_RES                 2
                        note = diphenylalanine
source                  1..9
                        mol_type = protein
                        organism = synthetic construct
SEQUENCE: 30
KAKKWWKKW                                                                                9

SEQ ID NO: 31           moltype = AA  length = 9
FEATURE                 Location/Qualifiers
REGION                  1..9
                        note = Synthetic sequence
MOD_RES                 3
                        note = diphenylalanine
source                  1..9
                        mol_type = protein
                        organism = synthetic construct
SEQUENCE: 31
KKAWKKWWK                                                                                9

SEQ ID NO: 32           moltype = AA  length = 9
FEATURE                 Location/Qualifiers
REGION                  1..9
                        note = Synthetic sequence
REGION                  1..9
                        note = D-amino acid
MOD_RES                 6
                        note = diphenylalanine
source                  1..9
                        mol_type = protein
                        organism = synthetic construct
SEQUENCE: 32
KWWKKAWKK                                                                                9

SEQ ID NO: 33           moltype = AA  length = 9
FEATURE                 Location/Qualifiers
REGION                  1..9
                        note = Synthetic sequence
MOD_RES                 3
                        note = biphenylalanine
source                  1..9
                        mol_type = protein
                        organism = synthetic construct
SEQUENCE: 33
RRAWRRWWR                                                                                9

SEQ ID NO: 34           moltype = AA  length = 9
FEATURE                 Location/Qualifiers
REGION                  1..9
                        note = Synthetic sequence
MOD_RES                 3
                        note = diphenylalanine
source                  1..9
                        mol_type = protein
                        organism = synthetic construct
SEQUENCE: 34
RRAWRRWWR                                                                                9

SEQ ID NO: 35           moltype = AA  length = 9
FEATURE                 Location/Qualifiers
REGION                  1..9
                        note = Synthetic sequence
REGION                  1..9
                        note = D-amino acid
MOD_RES                 3
                        note = biphenylalanine
source                  1..9
                        mol_type = protein
                        organism = synthetic construct
SEQUENCE: 35
KKAWKKWWK                                                                                9
```

```
SEQ ID NO: 36          moltype = AA   length = 9
FEATURE                Location/Qualifiers
REGION                 1..9
                       note = Synthetic sequence
REGION                 1..2
                       note = D-amino acid
MOD_RES                3
                       note = biphenylalanine
REGION                 4..9
                       note = D-amino acid
source                 1..9
                       mol_type = protein
                       organism = synthetic construct
SEQUENCE: 36
KKAWKKWWK                                                                 9

SEQ ID NO: 37          moltype = AA   length = 9
FEATURE                Location/Qualifiers
REGION                 1..9
                       note = Synthetic sequence
MOD_RES                3
                       note = D-biphenylalanine
source                 1..9
                       mol_type = protein
                       organism = synthetic construct
SEQUENCE: 37
KKAWKKWWK                                                                 9

SEQ ID NO: 38          moltype =    length =
SEQUENCE: 38
000

SEQ ID NO: 39          moltype = AA   length = 9
FEATURE                Location/Qualifiers
REGION                 1..9
                       note = Synthetic sequence
MOD_RES                4
                       note = 1-naphthylalanine
source                 1..9
                       mol_type = protein
                       organism = synthetic construct
SEQUENCE: 39
KKWAKKWWK                                                                 9

SEQ ID NO: 40          moltype = AA   length = 9
FEATURE                Location/Qualifiers
REGION                 1..9
                       note = Synthetic sequence
MOD_RES                4
                       note = 2-naphthylalanine
source                 1..9
                       mol_type = protein
                       organism = synthetic construct
SEQUENCE: 40
KKWAKKWWK                                                                 9

SEQ ID NO: 41          moltype = AA   length = 9
FEATURE                Location/Qualifiers
REGION                 1..9
                       note = Synthetic sequence
SITE                   4
                       note = 2-amino-3-(anthracen-9-yl)propanoic acid
source                 1..9
                       mol_type = protein
                       organism = synthetic construct
SEQUENCE: 41
KKWXKKWWK                                                                 9

SEQ ID NO: 42          moltype = AA   length = 9
FEATURE                Location/Qualifiers
REGION                 1..9
                       note = Synthetic sequence
SITE                   4
                       note = 2-amino-3-[1,1':4',1''-terphenyl-4-yl]propionic acid
source                 1..9
                       mol_type = protein
                       organism = synthetic construct
SEQUENCE: 42
KKWXKKWWK                                                                 9
```

```
SEQ ID NO: 43         moltype = AA   length = 9
FEATURE               Location/Qualifiers
REGION                1..9
                      note = Synthetic sequence
MOD_RES               4
                      note = Diphenylalanine
source                1..9
                      mol_type = protein
                      organism = synthetic construct
SEQUENCE: 43
KAQAQKQAW                                                                 9
```

The invention claimed is:

1. A method of treating a tumour in a subject in need thereof, comprising combined, sequential or separate administration to said subject of an immune checkpoint inhibitor and a compound having the following characteristics:
   a) consisting of 9 amino acids in a linear arrangement;
   b) of those 9 amino acids, 5 are cationic and 4 have a lipophilic R group; and
   c) at least one of said 9 amino acids is a non genetically coded amino acid;
   wherein the immune checkpoint inhibitor is an anti-PD-1 antibody.

2. The method of claim 1, wherein the compound is of formula:

$$CCLLCCLLC \quad (I)$$

or $$CLLCCLLCC \quad (III)$$

wherein C represents a cationic amino acid and L represents an amino acid with a lipophilic R group and in which one of the amino acids having a lipophilic R group is a non-genetically coded amino acid, said compound optionally in the form of a salt, ester or amide.

3. The method of claim 1, wherein each lipophilic R group has at least 9 non-hydrogen atoms.

4. The method of claim 1, wherein each lipophilic R group has at least one cyclic group.

5. The method of claim 1, in which 1 to 3 of the amino acids with lipophilic R groups are tryptophan.

6. The method of claim 1, wherein the compound incorporates a non-genetically coded amino acid selected from the group consisting of:

2-amino-3-(biphenyl-4-yl) propanoic acid (biphenylalanine), 2-amino-3,3-diphenylpropanoic acid (diphenylalanine), 2-amino-3-(anthracen-9-yl) propanoic acid, 2-amino-3-(naphthalen-2-yl) propanoic acid, 2-amino-3-(naphthalen-1-yl) propanoic acid, 2-amino-3-[1,1':4',1''-terphenyl-4-yl]-propionic acid, 2-amino-3-(2,5,7-tri-tert-butyl-1H-indol-3-yl) propanoic acid, 2-amino-3-[1,1': 3',1''-terphenyl-4-yl]-propionic acid, 2-amino-3-[1,1':2',1''-terphenyl-4-yl]-propionic acid, 2-amino-3-(4-naphthalen-2-yl-phenyl)-propionic acid, 2-amino-3-(4'-butylbiphenyl-4-yl) propanoic acid, 2-amino-3-[1,1': 3',1''-terphenyl-5'-yl]-propionic acid and 2-amino-3-(4-(2,2-diphenylethyl)phenyl) propanoic acid.

7. The method of claim 1, wherein the compound has the formula of SEQ ID NO: 23, or a salt, ester or amide thereof.

8. The method of claim 1, wherein the immune checkpoint inhibitor is selected from the group consisting of nivolumab, pembrolizumab and pidilizumab.

9. The method of claim 8, wherein the immune checkpoint inhibitor is pembrolizumab.

10. The method of claim 1, wherein the compound is a peptide.

11. The method of claim 1, wherein the compound has the further characteristic that lipophilic and cationic residues are arranged such that there are no more than two of either type of residue adjacent to one another.

12. The method of claim 1, wherein the compound has the further characteristic that the molecule comprises two pairs of adjacent cationic amino acids and one or two pairs of adjacent lipophilic residues.

13. The method of claim 7, wherein the immune checkpoint inhibitor is selected from the group consisting of nivolumab, pembrolizumab and pidilizumab.

14. The method of claim 7, wherein the immune checkpoint inhibitor is pembrolizumab.

* * * * *